(12) United States Patent
Chen et al.

(10) Patent No.: US 8,592,448 B2
(45) Date of Patent: *Nov. 26, 2013

(54) SUBSTITUTED PYRROLO[2,3-B]-PYRIDINES AND -PYRAZINES

(75) Inventors: Xin Chen, Commack, NY (US); Melzhong Jin, Dix Hills, NY (US); Andrew Kleinberg, East Meadow, NY (US); An-Hu Li, Commack, NY (US); Mark J. Mulvihill, Melville, NY (US); Arno G. Steinig, East Northport, NY (US); Jing Wang, Syosset, NY (US)

(73) Assignee: OSI Pharmaceuticals, LLC, Farmingdale, NY (US)

( * ) Notice: Subject to any disclaimer, the term of this patent is extended or adjusted under 35 U.S.C. 154(b) by 80 days.

This patent is subject to a terminal disclaimer.

(21) Appl. No.: 13/130,113

(22) PCT Filed: Nov. 19, 2009

(86) PCT No.: PCT/US2009/065058
§ 371 (c)(1),
(2), (4) Date: May 19, 2011

(87) PCT Pub. No.: WO2010/059771
PCT Pub. Date: May 27, 2010

(65) Prior Publication Data
US 2011/0224191 A1    Sep. 15, 2011

Related U.S. Application Data

(60) Provisional application No. 61/116,375, filed on Nov. 20, 2008.

(51) Int. Cl.
*A61K 31/437* (2006.01)
(52) U.S. Cl.
USPC .......................... 514/300; 546/113
(58) Field of Classification Search
USPC ...................................... 546/113
See application file for complete search history.

(56) References Cited

U.S. PATENT DOCUMENTS

| | | |
|---|---|---|
| 6,235,769 B1 | 5/2001 | Clary |
| 7,230,098 B2 | 6/2007 | Cui |
| 7,259,154 B2 | 8/2007 | Cox |
| 7,452,993 B2 | 11/2008 | Arnold |
| 7,585,876 B2 | 9/2009 | Bernotas |
| 2004/0116488 A1 | 6/2004 | Jennings |
| 2005/0182060 A1 | 8/2005 | Kelly |
| 2006/0046991 A1 | 3/2006 | Cui |
| 2006/0128724 A1 | 6/2006 | Cui |
| 2006/0178374 A1 | 8/2006 | Cui |
| 2007/0032519 A1 | 2/2007 | Zhang |
| 2007/0043068 A1 | 2/2007 | Arnold |
| 2007/0049615 A1 | 3/2007 | Ibrahim |
| 2007/0060633 A1 | 3/2007 | Mugge |
| 2007/0066641 A1 | 3/2007 | Ibrahim |
| 2007/0072874 A1 | 3/2007 | Cui |
| 2007/0123535 A1 | 5/2007 | Greenhouse |
| 2007/0287711 A1 | 12/2007 | Arnold |
| 2008/0167338 A1 | 7/2008 | Spevak |
| 2008/0221148 A1 | 9/2008 | Ibrahim |
| 2008/0221197 A1 | 9/2008 | Lam et al. |
| 2008/0293769 A1 | 11/2008 | Cui |
| 2009/0005356 A1 | 1/2009 | Blaney |
| 2009/0005378 A1 | 1/2009 | Arnold |
| 2009/0076046 A1 | 3/2009 | Zhang |
| 2009/0143352 A1 | 6/2009 | Arnold |
| 2010/0063031 A1 | 3/2010 | Liang |
| 2010/0256365 A1 | 10/2010 | Ibrahim |
| 2011/0281888 A1 | 11/2011 | Mulvihill |

FOREIGN PATENT DOCUMENTS

| | | |
|---|---|---|
| WO | 03082868 A1 | 10/2003 |
| WO | 2005004607 A1 | 1/2005 |
| WO | 2005010005 A1 | 2/2005 |
| WO | 2005062795 A2 | 7/2005 |
| WO | 2007002325 A1 | 1/2007 |
| WO | 2007002433 A1 | 1/2007 |
| WO | 2007062998 A1 | 6/2007 |

(Continued)

OTHER PUBLICATIONS

Database CA [online] Chemical Abstracts Service, Columbus, Ohio, US; XP002650560; Database Accession No. 143:145775 the whole document (2005).
IPRP and Written Opinion of the International Search Authority in PCT/US2009/065058 mailed Jun. 3, 2011.
International Search Report in PCT/US2009/065058, mailed Feb. 8, 2010.
International Search Report and Written Opinion of the International Search Authority in PCT/US2011/036572, mailed Jul. 14, 2011.
International Search Report and Written Opinion of the International Search Authority in PCT/US2011/036573, mailed Jul. 25, 2011.
Arteaga, (2007) Nature Medicine 13 (6) pp. 675-677.
Brabletz et al., (2005) Nature Rev., 5 pp. 744-749.
Camp et al., (2007)Cancer 109(6) pp. 1030-1039.

(Continued)

Primary Examiner — Brian McDowell
(74) Attorney, Agent, or Firm — Frank W. Forman; Astellas US LLC

(57) ABSTRACT

Compounds of Formula I, as shown below and defined herein: (I) pharmaceutically acceptable salts, synthesis, intermediates, formulations, and methods of disease treatment therewith, including cancers mediated at least in part by Ron and/or Met.

(I)

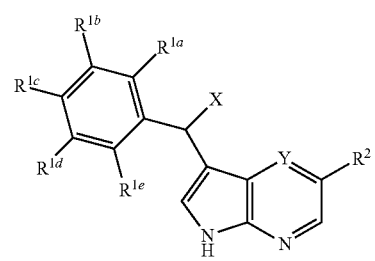

18 Claims, No Drawings

(56) References Cited

FOREIGN PATENT DOCUMENTS

| | | | |
|---|---|---|---|
| WO | 2007064797 A2 | | 6/2007 |
| WO | 2007067537 A1 | | 6/2007 |
| WO | 2007075567 A1 | | 7/2007 |
| WO | 2007132308 A1 | | 11/2007 |
| WO | 2007138472 A2 | | 12/2007 |
| WO | 2008008539 A3 | | 1/2008 |
| WO | 2008019968 A1 | | 2/2008 |
| WO | 2008031513 A1 | | 3/2008 |
| WO | 2008039457 A3 | | 4/2008 |
| WO | 2008051805 A2 | | 5/2008 |
| WO | 2008051808 A3 | | 5/2008 |
| WO | 2008053157 A1 | | 5/2008 |
| WO | 2008080015 A2 | | 7/2008 |
| WO | WO 2008/080001 | * | 7/2008 |
| WO | 2008124849 A3 | | 10/2008 |
| WO | 2009080534 A1 | | 7/2009 |
| WO | 2009094123 A1 | | 7/2009 |
| WO | 2009140549 A1 | | 11/2009 |
| WO | 2010039248 A1 | | 4/2010 |
| WO | 2010104945 A1 | | 9/2010 |
| WO | 2011143645 A1 | | 11/2011 |
| WO | 2011143646 A1 | | 11/2011 |
| WO | 2012158658 A1 | | 11/2012 |

OTHER PUBLICATIONS

Christensen et al., (2005) Cancer Letters, 225(1) pp. 1-26.
Christofori, (2006) Nature 441 pp. 444-450.
Comoglio et al., (2008) Nature Reviews Drug Disc. 7 (6) pp. 504-516.
Eng C., (2008) Nature 455 pp. 883-884.
Engelman, et al. (2007) Science 316 pp. 1039-1043.
Gentile et al., (2008) Cancer & Metastasis Reviews, 27 (1) pp. 85-94.
Giam C.S. et al. (1984) "A New Approach to the Preparation of 1, 6- and 1. 7-Naphthyridines". J. Chem. Soc. Chem. Commun., No. 5, pp. 265-266, XP002650561, Compound 4b.
Grotegut et al., (2006) EMBO J. 25 (15) pp. 3534-3545.
Gupta et al., (2006) Cell 127 pp. 679-695.
Jarvis, L. (2007) Chemical & Engineering News 85 (34), pp. 15-23.
Lawrence B. et al., (2000) Am J. Pathol., 157 (2) pp. 377-384.
McDermott U. et al., (2008) Cancer Res. 68 pp. 3389-3395.
Maggiora et al., (1997) J. Cell Physiol., 173 pp. 183-186.
Maulik et al., (2002) Cytokine & Growth Factor Reviews, 13 pp. 41-59.
Morris S.W. et al., (1994) Science 263 pp. 1281-1284.
Oft et al., (1996) Genes & Dev. 10 p. 2462-2477.
Perl et al., (1998) Nature 392 pp. 190-193.
Porter, J. et al. (2009) "Discovery of 4-azaindoles as novel inhibitors of c-Met kinase". Bioorganic & Medicinal Chemistry Letters, Pergamon, Elsevier Science, GB. vol. 19, No. 10, May 15, 2009, pp. 2780-2784, XP026085966, ISSN: 0960-894X, DOI: 10.1016/J.BMCL.2009.03.110 [retrieved on Mar. 27, 2009] compound 52.
Saucier, (2004) PNAS 101 (8) p. 2345-2350.
Smolen et al., (2006) Proc. Natl. Acad. Sci. USA 103 (7) pp. 2316-2321.
Soda M et al., (2007) Nature 448 pp. 561-566.
Sweeney, Z.K. et al. (2008) "Design of Annulated Pyrazoles as Inhibitors of HIV-1 Reverse Transcriptase". J. Med. Chem. vol. 51, pp. 7449-7458, XP002650559, compound 4.
Thiery, (2002) Nature Rev. Cancer 2 (6) 442-454.
Wan, Z-K, et al. (2001) "Dienophilicity of imidazole in inverse electron demand Diels-Alder reactions: cycloadditions with 1, 2,4,5-tetrazines and the structure of zarzissine". Tetrahedron, Elsevier Science Publishers, Amsterdam, NL. vol. 57, No. 26, Jun. 25, 2001, pp. 5497-5507, XP004247085, ISSN: 0040-4020, DIO: 10.1016/S0040-4020(01)00476-8 compound 10c.
Wang et al., (2008) J. Appl. Poly. Sci., 109 (5) pp. 3369-3375.
Wang et al., (2004) Oncogene 23 (9) pp. 1668-1680.
Zeng, et al., (2008) Cancer Letters 265 (2) pp. 258-269.
Zou et al., (2007) Cancer Res., 67 (9) p. 4408-4417.
International Search Report and Written Opinion of the International Search Authority in PCT/US2012/037866, mailed Jul. 13, 2012.
IPRP and Written Opinion of the International Search Authority in PCT/US2011/036572 mailed Nov. 29, 2012.
IPRP and Written Opinion of the International Search Authority in PCT/US2011/036573 mailed Nov. 29, 2012.
"Cancer," MedLine Plus (2009) Accessed Mar. 17, 2009 <http://www.nlm.nih.gov/medlineplus/cancer.html>.
Golub, et al., (1999) Science vol. 286, pp. 531-537.
Johnson, et al., (2001) British Journal of Cancer vol. 84 (10) pp. 1424-1431.
Sausville, et al., (2006) Cancer Res. 66 (7) pp. 3351-3354.

* cited by examiner

SUBSTITUTED PYRROLO[2,3-B]-PYRIDINES AND -PYRAZINES

This application claims priority of U.S. Application No. 61/116,375, the contents of which are fully incorporated herein by reference.

FIELD AND BACKGROUND

The present invention pertains at least in part to cancer treatment, certain chemical compounds, and methods of treating tumors and cancers with the compounds.

RON (recepteur d'origine nantais) is a receptor tyrosine kinase that is part of the MET proto-oncogene family. It is activated by binding to its natural ligand MSP and signals via the PI3K and MAPK pathways. RON can be deregulated in cancer by mechanisms such as over-expression of the receptor and/or the presence of constitutively active splice variants. Inhibition of RON has been shown to lead to a decrease in proliferation, induction of apoptosis and affects cell metastasis. RON overexpression is observed in a variety of human cancers and exhibits increased expression with progression of the disease.

MET (also known as c-Met) is a receptor tyrosine kinase that is a heterodimeric protein comprising of a 50 kDa α-subunit and a 145 kDa β-subunit (Maggiora et al., J. Cell Physiol., 173:183-186, 1997). It is activated by binding to its natural ligand HGF (hepatocyte growth factor, also known as scatter factor) and signals via the PI3K and MAPK pathways. MET can be deregulated in cancer by mechanisms such as autocrine/paracrine HGF activation, over-expression of the receptor, and/or the presence of activating mutations. Significant expression of MET has been observed in a variety of human tumors, such as colon, lung, prostate (including bone metastases), gastric, renal, HCC, ovarian, breast, ESCC, and melanoma (Maulik et al., Cytokine & Growth Factor Reviews 13:41-59, 2002). MET is also implicated in atherosclerosis and lung fibrosis. Inhibition of MET can cause a decrease in cell motility, proliferation and metastasis, as reviewed in, e.g., Chemical & Engineering News 2007, 85 (34), 15-23.

Elevated expression of cMET has been detected in numerous cancers including lung, breast, colorectal, prostate, pancreatic, head and neck, gastric, hepatocellular, ovarian, renal, glioma, melanoma, and some sarcomas (see reviews Christensen, J., 2005; Comoglio, P., 2008). cMET gene amplification and resulting overexpression has been reported in gastric and colorectal cancer (Smolen, G., 2005; Zeng Z., 2008). Taken together, the cMET proto-oncogene has a role in human cancer and its over-expression correlates with poor prognosis. Abrogation of cMET function with small molecule inhibitors, anti-cMET antibodies or anti-HGF antibodies in preclinical xenograft model systems has shown impact when cMET signaling serves as the main driver for proliferation and cell survival (Comoglio, P., 2008).

As human cancers progress to a more invasive, metastatic state, multiple signaling programs regulating cell survival and migration programs are observed depending on cell and tissue contexts (Gupta and Massague, 2006). Recent data highlight the transdifferentiation of epithelial cancer cells to a more mesenchymal-like state, a process resembling epithelial-mesenchymal transition (EMT); (Oft et al., 1996; Pert et al., 1998), to facilitate cell invasion and metastasis (Brabletz et al., 2005; Christofori, 2006). Through EMT-like transitions mesenchymal-like tumor cells are thought to gain migratory capacity at the expense of proliferative potential. A mesenchymal-epithelial transition (MET) has been postulated to regenerate a more proliferative state and allow macrometastases resembling the primary tumor to form at distant sites (Thiery, 2002). MET and RON kinases have been shown to play a role in the EMT process (Camp et al., 2007; Grotegut et al., 2006; Wang et al., 2004). It has been documented in vitro that RON and MET can form heterodimers and signal via such RON-MET dimers.

cMET and RON are known to interact and influence the activation of one another. Furthermore, co-expression of the two receptors, when compared to each receptor alone, is associated with the poorest clinical prognosis in bladder, CRC, and breast cancer patients. Since co-expression of RON and MET in cancer has been observed, such "cross-talk" may contribute to tumor growth.

The following published documents are also noted: WO08/051,808; WO08/051,805; WO08/008,539; WO08/039,457; WO07/138,472; WO07/132,308; WO07/075,567; WO07/067,537; WO07/064,797; WO05/010005; WO05/004607; U.S. Pat. No. 7,230,098; US2007/287711; US2005/182060; US2006/128724; US2007/060633; US2007/049615; US2007/043068; US2007/032519; US2007/012535; US2006/046991; Wang et al., J. Appl. Poly. Sci., 109(5), 3369-3375 (2008).

There is a need for effective therapies for use in proliferative disease, including treatments for primary cancers, prevention of metastatic disease, and targeted therapies, including tyrosine kinase inhibitors, such as MET and/or RON inhibitors, dual inhibitors, including selective inhibitors, and for potent, orally bioavailable, and efficacious inhibitors, and inhibitors that maintain sensitivity of E cells to epithelial cell directed therapies.

SUMMARY

In some aspects, the present invention concerns compounds of Formula I, as shown below and defined herein:

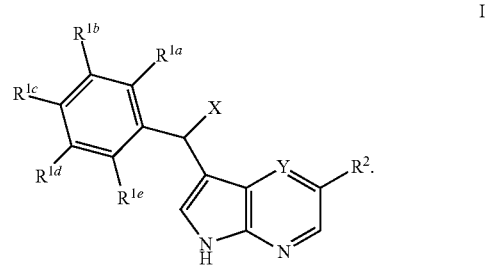

The invention includes the compounds and pharmaceutically acceptable salts thereof.

The invention includes the compounds and salts thereof, and their physical forms, preparation of the compounds, useful intermediates, and pharmaceutical compositions and formulations thereof.

In some aspects, compounds of the invention are inhibitors of kinases, including at least one of the c-MET, and RON kinases.

In some aspects, compounds of the invention are inhibitors of kinases, including at least one of c-MET, RON, Tie-2, Flt3, FGFR3, Abl, Aurora A, Aurora B, Jak2, Alk, c-Src, IGF-1R, c-MET, RON, PAK1, PAK2, and TAK1 kinases.

In some aspects, compounds of the invention are selective inhibitors of MET and/or RON. In some embodiments, the compound is a selective inhibitor of c-MET and/or RON over other kinase targets, such as KDR.

In some aspects, compounds of the invention are useful in treating proliferative disease, particularly cancers, including cancers mediated by c-MET and/or RON, alone or in combination with other agents.

DETAILED DESCRIPTION

Compounds

In some aspects, the present invention concerns compounds and salts thereof of Formula I, as shown below and defined herein:

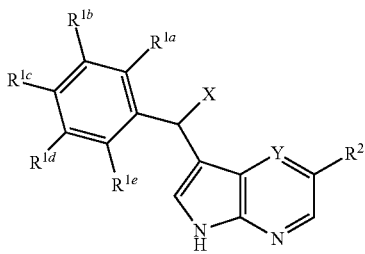

I or a pharmaceutically acceptable salt thereof, wherein:
X is selected from —OH, $C_{1-3}$alkyl, or $C_{1-3}$alkoxy;
Y is selected from CH or N;
$R^{1a}$, $R^{1b}$, $R^{1c}$, $R^{1d}$, $R^{1e}$ are each independently selected from H, halo, —CN, $C_{1-6}$ alkyl, —CF$_3$, —OCF$_3$, —OC$_{0-6}$ alkyl, —S(O)$_m$C$_{1-6}$alkyl, —SO$_2$N(C$_{0-6}$alkyl)(C$_{0-6}$alkyl), —N(C$_{0-6}$alkyl)(C$_{0-6}$alkyl), —N(C$_{0-6}$alkyl)C(=O)C$_{0-6}$alkyl, —N(C$_{0-6}$alkyl)C(=O)OC$_{0-6}$alkyl, —N(C$_{0-6}$alkyl)C(=O)N(C$_{0-6}$alkyl)(C$_{0-6}$alkyl), —C(=O)C$_{0-6}$alkyl, —C(=O)OC$_{0-6}$alkyl, —C(=O)N(C$_{0-6}$alkyl)(C$_{0-6}$alkyl), —O-heterocyclyl, —N(C$_{0-6}$alkyl)-heterocyclyl, —N(C$_{0-6}$alkyl)-heteroaryl, heterocyclyl, heteroaryl, —S-heteroaryl, or —O-heteroaryl; wherein the heterocyclyl is optionally substituted with oxo, $C_{1-6}$alkyl, C(=O)OC$_{1-6}$alkyl, C(=O)C$_{0-6}$alkyl, C(=O)N(C$_{0-6}$alkyl)(C$_{0-6}$alkyl), SO$_2$N(C$_{0-6}$alkyl)(C$_{0-6}$alkyl), or SO$_2$C$_{1-6}$alkyl; wherein the alkyl is optionally substituted with —OH, —OC$_{1-6}$alkyl, N(C$_{0-6}$alkyl)(C$_{0-6}$alkyl), C(=O)N(C$_{0-6}$alkyl)(C$_{0-6}$alkyl), C(=O)OC$_{0-6}$alkyl, C(=O)C$_{0-6}$alkyl, heterocyclyl, or heteroaryl;

$R^2$ is selected from H, halo, —CN, —CF$_3$, —NO$_2$, $C_{0-6}$alkyl, $C_{2-6}$alkenyl, $C_{2-6}$alkynyl, $C_{3-6}$cycloalkylC$_{0-6}$alkyl, $C_{3-6}$heterocycloalkylC$_{0-6}$alkyl, arylC$_{0-6}$alkyl, or heteroarylC$_{0-6}$alkyl, any of which is optionally substituted with one or more independent $G^1$ substituents;
or $R^2$ is selected from:

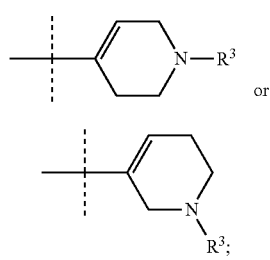

$R^3$ is selected from H, $C_{1-12}$alkyl, $R^4$O—C$_{2-12}$alkyl, $R^4R^5$N—C$_{2-12}$alkyl, $R^4$S(O)$_m$—C$_{2-12}$alkyl, $C_{3-12}$cycloalkylC$_{0-12}$alkyl, $C_{3-12}$cycloalkenylC$_{1-12}$alkyl, heterocycloalkylC$_{0-12}$alkyl, arylC$_{0-12}$alkyl, heteroarylC$_{0-12}$alkyl, $C_{1-12}$alkylC$_{3-12}$cycloalkyl, $C_{3-12}$cycloalkylC$_{3-12}$cycloalkyl, $C_{3-12}$cycloalkenylC$_{3-12}$cycloalkyl, heterocycloalkylC$_{3-12}$cycloalkyl, arylC$_{3-12}$cycloalkyl, heteroarylC$_{3-12}$cycloalkyl, $C_{1-12}$alkyl-heterocycloalkyl, $C_{3-12}$cycloalkyl-heterocycloalkyl, $C_{3-12}$cycloalkenyl-heterocycloalkyl, heterocycloalkyl-heterocycloalkyl, aryl-heterocycloalkyl, heteroaryl-heterocycloalkyl, —C(O)R$^a$, $R^4$O—C$_{0-12}$alkylC(O)—, $R^4R^5$N—C$_{0-12}$alkylC(O)—, $R^4$S(O)$_m$C$_{0-12}$alkylC(O)—, —CO$_2$R$^4$, —C(O)NR$^4$R$^5$, —S(O)$_m$R$^4$, —SO$_2$NR$^4$R$^5$ or —C(S)OR$^4$, any of which is optionally substituted with one or more independent $G^2$ substituents;

$G^1$ and $G^2$ are each independently selected from halo, —CN, —CF$_3$, —OCF$_3$, —NO$_2$, oxo, R$^6$, $C_{1-12}$alkyl, $C_{2-12}$alkenyl, $C_{2-12}$alkynyl, $C_{3-12}$cycloalkylC$_{0-12}$alkyl, heterocycloalkylC$_{0-12}$alkyl, arylC$_{0-12}$alkyl, heteroarylC$_{0-12}$alkyl, —OR$^6$, —S(O)$_m$R$^6$, —NR$^6$R$^7$, —SO$_2$NR$^6$R$^7$, —C(O)R$^b$, —C(O)NR$^6$R$^7$, —C(O)—C(O)NR$^6$R$^7$, —C(O)OR$^6$, —C(O)—C(O)OR$^6$, —OC(O)R$^b$, —NR$^6$C(O)R$^b$, —NR$^6$S(O)$_2$R$^7$, —(CR$^8$R$^9$)$_n$C(O)R$^b$, —(CR$^8$R$^9$)$_n$C(O)OR$^6$, —(CR$^8$R$^9$)$_n$C(O)NR$^6$R$^7$, —(CR$^8$R$^9$)$_n$S(O)$_2$NR$^6$R$^7$, —(CR$^8$R$^9$)$_n$NR$^6$R$^7$, —(CR$^8$R$^9$)$_n$OR$^6$, —(CR$^8$R$^9$)$_n$S(O)$_m$R$^6$, —NR$^{10}$C(O)NR$^6$R$^7$, —NR$^{10}$S(O)$_2$NR$^6$R$^7$, or —NR$^{10}$S(O)NR$^6$R$^7$, any of which is optionally substituted with one or more independent Q$^1$ substituents;

Q$^1$ is selected from halo, —CN, —NO$_2$, oxo, —CF$_3$, —OCF$_3$, $C_{1-12}$alkyl, arylC$_{0-12}$alkyl, heteroarylC$_{0-12}$alkyl, $C_{3-12}$cycloalkylC$_{0-12}$alkyl, heterocycloalkylC$_{0-12}$alkyl, arylC$_{3-12}$cycloalkyl, heteroarylC$_{3-12}$cycloalkyl, heterocycloalkylC$_{3-12}$cycloalkyl, $C_{3-12}$cycloalkylC$_{3-12}$cycloalkyl, $C_{1-12}$alkyl-heterocycloalkyl, heterocycloalkyl-heterocycloalkyl, aryl-heterocycloalkyl, heteroaryl-heterocycloalkyl, —C(O)—C(O)NR$^{11}$R$^{12}$, —C(O)—C(O)OR$^{11}$, —OC(O)R$^c$, —NR$^{11}$C(O)R$^c$, —NR$^{11}$S(O)$_2$R$^{12}$, —(CR$^{13}$R$^{14}$)$_m$C(O)R$^c$, —(CR$^{13}$R$^{14}$)$_m$C(O)OR$^{11}$, —(CR$^{13}$R$^{14}$)$_n$C(O)NR$^{11}$R$^{12}$, —(CR$^{13}$R$^{14}$)$_n$S(O)$_2$NR$^{11}$R$^{12}$, —(CR$^{13}$R$^{14}$)$_n$NR$^{11}$R$^{12}$, —(CR$^{13}$R$^{14}$)$_n$OR$^{11}$, —(CR$^{13}$R$^{14}$)$_n$S(O)$_m$R$^{11}$, —NR$^{15}$C(O)NR$^{11}$R$^{12}$, —NR$^{15}$S(O)$_2$NR$^{11}$R$^{12}$ or —NR$^{15}$S(O)NR$^{11}$R$^{12}$, any of which is optionally substituted with one or more independent Q$^2$ substituents;

Q$^2$ is selected from halo, —CN, —OH, —NH$_2$, —NO$_2$, oxo, —CF$_3$, —OCF$_3$, —CO$_2$H, —S(O)$_m$H, $C_{1-12}$alkyl, arylC$_{0-12}$alkyl, heteroarylC$_{0-12}$alkyl, $C_{3-12}$cycloalkylC$_{0-12}$alkyl, heterocycloalkylC$_{0-12}$alkyl, arylC$_{3-12}$cycloalkyl, heteroarylC$_{3-12}$cycloalkyl, heterocycloalkyl C$_{3-12}$cycloalkyl, $C_{3-12}$cycloalkylC$_{3-12}$cycloalkyl, $C_{1-12}$alkylheterocycloalkyl, heterocycloalkyl-heterocycloalkyl, aryl-heterocycloalkyl or heteroaryl-heterocycloalkyl, any of which is optionally substituted with one or more independent halo, —CN, —OH, —NH$_2$, or $C_{1-10}$alkyl which may be partially or fully halogenated, or —O—C$_{1-10}$alkyl which alkyl may be partially or fully halogenated;

each R$^4$, R$^5$, R$^6$, R$^7$, R$^8$, R$^9$, R$^{19}$, R$^{11}$, R$^{12}$, R$^{13}$, R$^{14}$, R$^{15}$, R$^a$, R$^b$, and R$^c$ is independently selected from H, $C_{1-12}$alkyl or $C_{3-12}$cycloalkyl, each optionally substituted by halo, —OCF$_3$, or by —OC$_{0-3}$alkyl, arylC$_{0-12}$alkyl, heteroarylC$_{0-12}$alkyl, $C_{3-12}$cycloalkylC$_{0-12}$alkyl, heterocycloalkylC$_{0-12}$alkyl, arylC$_{3-12}$cycloalkyl, heteroarylC$_{3-12}$cycloalkyl, heterocycloalkylC$_{3-12}$cycloalkyl, $C_{3-12}$cycloalkylC$_{3-12}$cycloalkyl, $C_{1-12}$alkyl-heterocycloalkyl, heterocycloalkyl-heterocycloalkyl, aryl-heterocycloalkyl, or heteroaryl-heterocycloalkyl;

—NR$^4$R$^5$, —NR$^6$R$^7$ and —NR$^{11}$R$^{12}$ is each independently linear structure; or R$^4$ and R$^5$, or R$^6$ and R$^7$, or R$^{11}$ and R$^{12}$, respectively, can be taken together with the nitrogen atom to which they are attached to form a 3-12 membered saturated or unsaturated ring, wherein said ring optionally includes one or more heteroatoms selected from O, N, or S(O)$_m$;

—CR$^8$R$^9$ or —CR$^{13}$R$^{14}$ is each independently linear structure; or R$^8$ and R$^9$, or R$^{13}$ and R$^{14}$, respectively, can be taken together with the carbon atom to which they are attached to form a 3-12 membered saturated or unsaturated ring, wherein said ring optionally includes one or more heteroatoms selected from O, N, or S(O)$_m$;

q=0 or 1; n=0-7; and m=0-2.

In some aspects, the present invention concerns compounds and salts thereof of Formula I, more specifically having the formula:

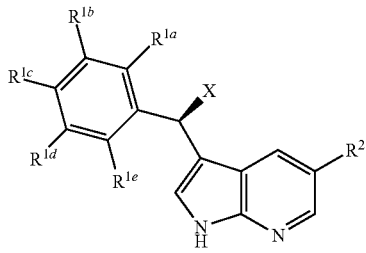

wherein X is selected from methyl, ethyl, or methoxy;

R$^{1a}$ and R$^{1e}$ are each independently selected from halo, —CN, —CF$_3$, —OCF$_3$, or —OC$_{0-6}$alkyl;

R$^{1b}$, R$^{1c}$, and R$^{1d}$ are each independently selected from H, halo, —CN, —CF$_3$, —OCF$_3$, or —OC$_{0-6}$alkyl; wherein the alkyl is optionally substituted with —OH, N(C$_{0-6}$alkyl)(C$_{0-6}$alkyl), C(=O)N(C$_{0-6}$alkyl)(C$_{0-6}$alkyl), C(=O)OC$_{0-6}$alkyl, C(=O)C$_{0-6}$alkyl, or heteroaryl;

R$^2$ is selected from halo, —CN, —CF$_3$, —NO$_2$, C$_{1-6}$alkyl, C$_{2-6}$alkenyl, C$_{2-6}$alkynyl, C$_{3-6}$cycloalkylC$_{0-6}$alkyl, C$_{3-6}$heterocycloalkylC$_{0-6}$alkyl, arylC$_{0-6}$alkyl, or heteroarylC$_{0-6}$alkyl, any of which is optionally substituted with 1-2 independent G$^1$ substituents;

or R$^2$ is selected from:

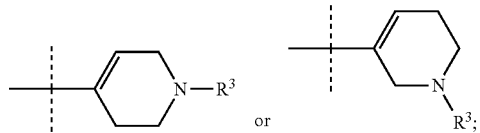

R$^3$ is selected from H, R$^4$O—C$_{2-12}$alkyl, R$^4$R$^5$N—C$_{2-12}$alkyl, R$^4$S(O)$_m$—C$_{2-12}$alkyl, C$_{3-12}$cycloalkyl C$_{0-12}$alkyl, C$_{3-12}$cycloalkenylC$_{1-12}$alkyl, C$_{3-12}$heterocycloalkylC$_{0-12}$alkyl, arylC$_{0-12}$alkyl, heteroarylC$_{0-12}$alkyl, C$_{1-12}$alkylC$_{3-12}$cycloalkyl, C$_{3-12}$cycloalkylC$_{3-12}$cycloalkyl, C$_{3-12}$cycloalkenylC$_{3-12}$cycloalkyl, C$_{3-12}$heterocycloalkyl C$_{3-12}$ cycloalkyl, arylC$_{3-12}$cycloalkyl, heteroarylC$_{3-12}$cycloalkyl, C$_{1-12}$alkylC$_{3-12}$heterocycloalkyl, C$_{3-12}$cycloalkylC$_{3-12}$heterocycloalkyl, C$_{3-12}$cycloalkenylC$_{3-12}$ heterocycloalkyl, C$_{3-12}$heterocycloalkylC$_{3-12}$ heterocycloalkyl, aryl C$_{3-12}$heterocycloalkyl, heteroarylC$_{3-12}$heterocycloalkyl, —C(O)R$^a$, R$^4$O—O$_{0-12}$alkylC(O)—, R$^4$R$^5$N—C$_{0-12}$alkylC(O)—, R$^4$S(O)$_m$C$_{0-12}$alkylC(O)—, —CO$_2$R$^4$, —C(O)NR$^4$R$^5$, —S(O)$_m$R$^4$, —SO$_2$NR$^4$R$^5$ or —C(S)OR$^4$, any of which is optionally substituted with 1-2 independent G$^2$ substituents;

each G$^1$ is independently selected from halo, —CN, —CF$_3$, —OCF$_3$, —NO$_2$, R$^6$, oxo, C$_{1-12}$alkyl, C$_{2-12}$alkenyl, C$_{2-12}$alkynyl, C$_{3-12}$cycloalkylC$_{0-12}$alkyl, C$_{3-12}$heterocycloalkylC$_{0-12}$alkyl, arylC$_{0-12}$alkyl, heteroaryl C$_{0-12}$alkyl, —OR$^6$, —S(O)$_m$R$^6$, —NR$^6$R$^7$, —SO$_2$NR$^6$R$^7$, —C(O)R$^b$, —C(O)NR$^6$R$^7$, —C(O)—C(O)NR$^6$R$^7$, —C(O)OR$^6$, —C(O)—C(O)OR$^6$, —OC(O)R$^b$, —NR$^6$C(O)R$^b$, —NR$^6$S(O)$_2$R$^7$, —(CR$^8$R$^9$)$_n$C(O)R$^b$, —(CR$^8$R$^9$)$_n$C(O)OR$^6$, —(CR$^8$R$^9$)$_n$C(O)NR$^6$R$^7$, —(CR$^8$R$^9$)$_n$S(O)$_2$NR$^6$R$^7$, —(CR$^8$R$^9$)$_n$NR$^6$R$^7$, —(CR$^8$R$^9$)$_n$OR$^6$, —(CR$^8$R$^9$)$_n$S(O)$_m$R$^6$, NR$^{10}$C(O)NR$^6$R$^7$, —NR$^{10}$S(O)$_2$NR$^6$R$^7$, or —NR$^{10}$S(O) NR$^6$R$^7$, any of which is optionally substituted with 1-2 independent Q$^1$ substituents;

each G$^2$ is independently selected from halo, —CN, —CF$_3$, —OCF$_3$, —NO$_2$, C$_{1-12}$alkyl, C$_{2-12}$alkenyl, C$_{2-12}$alkynyl, —OR$^6$, —S(O)$_m$R$^6$, —NR$^6$R$^7$, —SO$_2$NR$^6$R$^7$, —C(O) R$^b$, —C(O)NR$^6$R$^7$, —C(O)—C(O)NR$^6$R$^7$, —C(O)OR$^6$, —C(O)—C(O)OR$^6$, —OC(O)R$^b$, —NR$^6$C(O)R$^b$, —NR$^6$S (O)$_2$R$^7$, —(CR$^9$R$^9$)$_n$C(O)R$^b$, —(CR$^9$R$^9$)$_n$C(O)OR$^6$, —(CR$^9$R$^9$)$_n$C(O)NR$^6$R$^7$, —(CR$^9$R$^9$)$_n$S(O)$_2$NR$^6$R$^7$, —(CR$^9$R$^9$)$_n$NR$^6$R$^7$, —(CR$^9$R$^9$)$_n$OR$^6$, —(CR$^9$R$^9$)$_n$S(O)$_m$R$^6$, —NR$^{10}$C(O)NR$^6$R$^7$, —NR$^{10}$S(O)$_2$NR$^6$R$^7$, or —NR$^{10}$S(O) NR$^6$R$^7$, any of which is optionally substituted with 1-2 independent Q$^1$ substituents;

each Q$^1$ is selected from halo, —CN, —NO$_2$, oxo, —CF$_3$, —OCF$_3$, C$_{1-12}$alkyl, C$_{3-7}$cycloalkyl, —C(O)—C(O) NR$^{11}$R$^{12}$, —C(O)—C(O)OR$^{11}$, —OC(O)R$^c$, —NR$^{11}$C(O) R$^c$, —NR$^{11}$S(O)$_2$R$^{12}$, —(CR$^{13}$R$^{14}$)$_n$C(O)R$^c$, —(CR$^{13}$R$^{14}$)$_n$C(O)OR$^{11}$, —(CR$^{13}$R$^{14}$)$_n$C(O)NR$^{11}$R$^{12}$, —(CR$^{13}$R$^{14}$)$_n$S(O)$_2$ NR$^{11}$R$^{12}$, —(CR$^{13}$R$^{14}$)$_n$NR$^{11}$R$^{12}$, —(CR$^{13}$R$^{14}$)$_n$OR$^{11}$, —(CR$^{13}$R$^{14}$)$_n$S(O)$_m$R$^{11}$, —NR$^{15}$C(O)NR$^{11}$R$^{12}$, —NR$^{15}$S (O)$_2$NR$^{11}$R$^{12}$ or —NR$^{15}$S(O)NR$^{11}$R$^{12}$;

each R$^4$, R$^5$, R$^6$, R$^7$, R$^8$, R$^9$, R$^{19}$, R$^{11}$, R$^{12}$, R$^{13}$, R$^{14}$, R$^{15}$, R$^a$, R$^b$, and R$^c$ is independently C$_{0-12}$alkyl or C$_{3-7}$cycloalkyl, each independently optionally substituted by halo, —OCF$_3$, or —OC$_{0-3}$alkyl;

each —NR$^4$R$^5$, —NR$^6$R$^7$ and —NR$^{11}$R$^{12}$ is independently linear in structure; or R$^4$ and R$^5$, or R$^6$ and R$^7$, or R$^{11}$ and R$^{12}$, respectively, can be taken together with the nitrogen atom to which they are attached to form a 3-12 membered saturated or unsaturated ring, wherein said ring optionally includes one or more heteroatoms selected from O, N, or S(O)$_m$;

each —CR$^8$R$^9$ and —CR$^{13}$R$^{14}$ is independently linear in structure; or R$^8$ and R$^9$, or R$^{13}$ and R$^{14}$, respectively, can be taken together with the carbon atom to which they are attached to form a 3-12 membered saturated or unsaturated ring, wherein said ring optionally includes one or more heteroatoms selected from O, N, or S(O)$_m$;

q=0 or 1; n=0-4; and m=0-2.

In some aspects, the present invention concerns compounds and salts thereof of Formula I, more specifically having the formula:

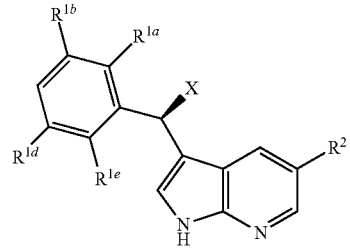

wherein X is selected from —OH, C$_{1-3}$alkyl, or C$_{1-3}$alkoxy;

R$^{1a}$ and R$^{1e}$ are each independently selected from halo, —CN, C$_{1-6}$alkyl, —CF$_3$, —OCF$_3$, or —OC$_{1-6}$alkyl;

R$^{1b}$ and R$^{1d}$ are each independently selected from H, halo, —CN, C$_{1-6}$alkyl, —CF$_3$, —OCF$_3$, or —OC$_{1-6}$alkyl;

(i) R$^2$ is phenyl or pyridinyl, each substituted by G$^1$ wherein G$^1$ is $_{4-7}$heterocycloalkyl optionally substituted with halogen, —OH, —OCH₃, or C₁₋₃alkyl, or G¹ is —C(O)NR⁶R⁷; wherein each R⁶ and R⁷ is independently C₀₋₃ alkyl; or NR⁶R⁷ defines a ₄₋₇heterocycloalkyl optionally substituted by C₁₋₆alkyl;

or (ii) R² is pyrazolo optionally substituted by G¹ wherein G¹ is ₄₋₆heterocycloalkyl optionally substituted by halo, —R⁶, oxo, —S(O)ₘR⁶, —SO₂NR⁶R⁷, —C(O)Rᵇ, —C(O)NR⁶R⁷, —C(O)—C(O)NR⁶R⁷, —C(O)OR⁶, or —C(O)—C(O)OR⁶; or G¹ is C₃₋₆cycloalkyl optionally substituted by OH, —OR⁶, oxo, —S(O)ₘR⁶, —SO₂NR⁶R⁷, —C(O)Rᵇ, —C(O)NR⁶R⁷, —C(O)—C(O)NR⁶R⁷, —C(O)OR⁶, or —C(O)—C(O)OR⁶; or —C₁₋₆alkyl which alkyl can be substituted by halo or —OC₀₋₅alkyl; or G¹ is C₁₋₆alkyl optionally substituted by —OH, —OR⁶, —R⁶, oxo, —NR⁶R⁷, —C(O)Rᵇ, —C(O)NR⁶R⁷, —C(O)—C(O)NR⁶R⁷, —C(O)OR⁶, —C(O)—C(O)OR⁶, —OC(O)Rᵇ, —NR⁶C(O)Rᵇ, —NR⁶S(O)₂R⁷, —(CR⁸R⁹)ₙC(O)Rᵇ, —(CR⁸R⁹)ₙC(O)OR⁶, —(CR⁸R⁹)ₙC(O)NR⁶R⁷, —(CR⁸R⁹)ₙS(O)₂NR⁶R⁷, —(CR⁸R⁹)ₙNR⁶R⁷, —(CR⁸R⁹)ₙOR⁶, —(CR⁸R⁹)ₙS(O)ₘR⁶, —NR¹⁹C(O)NR⁶R⁷, —NR¹⁹S(O)₂NR⁶R⁷, or —NR¹⁹S(O)NR⁶R⁷; wherein each R⁶, R⁷, R⁸, R⁹, R¹⁰, and Rᵇ is independently C₀₋₅alkyl or C₃₋₆cycloalkyl, each independently optionally substituted by halo, —OCF₃, or —OC₀₋₃alkyl; or NR⁶R⁷ defines a ₄₋₇heterocycloalkyl optionally substituted by C₁₋₆alkyl; and wherein each m is independently 0-2; each n is independently 0-2.

In some aspects, the present invention concerns compounds and salts thereof of Formula I, more specifically having the formula:

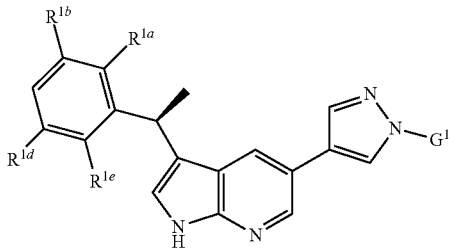

wherein R¹ᵃ and R¹ᵉ are each independently selected from halo, —CN, C₁₋₆alkyl, —CF₃, —OCF₃, or —OC₁₋₆alkyl;

R¹ᵇ and R¹ᵈ are each independently selected from H, halo, —CN, C₁₋₆alkyl, —CF₃, —OCF₃, or —OC₁₋₆alkyl;

G¹ is ₄₋₆heterocycloalkyl optionally substituted by halo, —R⁶, oxo, —S(O)ₘR⁶, —SO₂NR⁶R⁷, —C(O)Rᵇ, —C(O)NR⁶R⁷, —C(O)—C(O)NR⁶R⁷, —C(O)OR⁶, or —C(O)—C(O)OR⁶;

or G¹ is ₃₋₆cycloalkyl optionally substituted by OH, —OR⁶, oxo, —S(O)ₘR⁶, —SO₂NR⁶R⁷, —C(O)Rᵇ, —C(O)NR⁶R⁷, —C(O)—C(O)NR⁶R⁷, —C(O)OR⁶, or —C(O)—C(O)OR⁶, or —C₁₋₆alkyl which alkyl can be substituted by halo or —OC₀₋₅alkyl;

or G¹ is C₁₋₆alkyl optionally substituted by —OH, —OR⁶, —R⁶, oxo, —NR⁶R⁷, —C(O)Rᵇ, —C(O)NR⁶R⁷, —C(O)—C(O)NR⁶R⁷, —C(O)OR⁶, —C(O)—C(O)OR⁶, —OC(O)Rᵇ, —NR⁶C(O)Rᵇ, —NR⁶S(O)₂R⁷, —(CR⁸R⁹)ₙC(O)Rᵇ, —(CR⁸R⁹)ₙC(O)OR⁶, —(CR⁸R⁹)ₙC(O)NR⁶R⁷, —(CR⁸R⁹)ₙ S(O)₂NR⁶R⁷, —(CR⁸R⁹)ₙNR⁶R⁷, —(CR⁸R⁹)ₙOR⁶, —(CR⁸R⁹)ₙS(O)ₙR⁶, —NR¹⁰C(O)NR⁶R⁷, —NR¹⁰S(O)₂ NR⁶R⁷, or —NR¹⁰S(O)NR⁶R⁷;

wherein each R⁶, R⁷, R⁸, R⁹, R¹⁰, and Rᵇ is independently C₀₋₅ alkyl or C₃₋₆cycloalkyl, each independently optionally substituted by halo, —OCF₃, or —OC₀₋₃alkyl; or NR⁶R⁷ defines a ₄₋₇heterocycloalkyl optionally substituted by C₁₋₆alkyl; and each m is independently 0-2; and each n is independently 0-2.

In some aspects, the present invention concerns compounds and salts thereof of Formula I, more specifically having the formula:

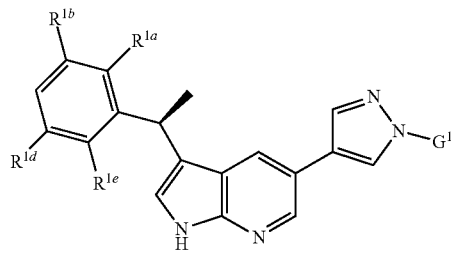

wherein R¹ᵃ and R¹ᵉ are both Cl;

each R¹ᵇ and R¹ᵈ is independently H, F, or —OCH₃;

G¹ is ₄₋₆heterocycloalkyl optionally substituted by halo, R⁶, oxo, —S(O)ₘR⁶, —SO₂NR⁶R⁷, —C(O)Rᵇ, —C(O)NR⁶R⁷, —C(O)—C(O)NR⁶R⁷, —C(O)OR⁶, or —C(O)—C(O)OR⁶;

wherein each R⁶, R⁷, and Rᵇ is independently C₀₋₅alkyl or C₃₋₆cycloalkyl, each independently optionally substituted by halo, —OCF₃, or —OC₀₋₃alkyl; or NR⁶R⁷ defines a ₄₋₇heterocycloalkyl optionally substituted by C₁₋₆alkyl; and m is 0-2.

In some aspects, the present invention concerns compounds and salts thereof of Formula I, more specifically having the formula:

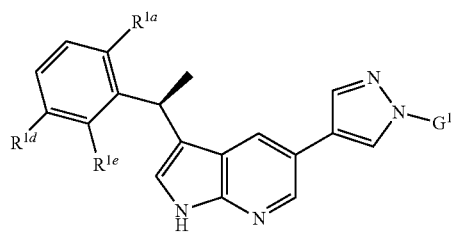

wherein R¹ᵃ and R¹ᵉ are both Cl;

R¹ᵈ is F or —OCH₃;

G¹ is ₄₋₆heterocycloalkyl optionally substituted by halo, R⁶, oxo, —S(O)ₘR⁶, —SO₂NR⁶R⁷, —C(O)Rᵇ, —C(O)NR⁶R⁷, —C(O)—C(O)NR⁶R⁷, —C(O)OR⁶, or —C(O)—C(O)OR⁶;

wherein each R⁶, R⁷, and Rᵇ is independently C₀₋₅alkyl or C₃₋₆cycloalkyl, each independently optionally substituted by halo, —OCF₃, or —OC₀₋₃alkyl; or NR⁶R⁷ defines a ₄₋₇heterocycloalkyl optionally substituted by C₁₋₆alkyl; and m is 0-2.

In some aspects, the present invention concerns compounds and salts thereof of Formula I, more specifically having the formula:

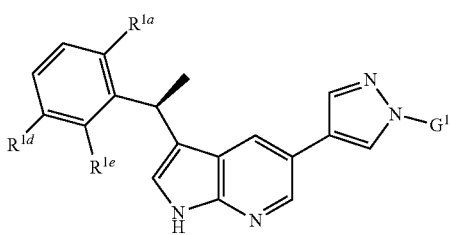

wherein $R^{1a}$ and $R^{1e}$ are both Cl;
$R^{1d}$ is F;
$G^1$ is selected from piperidine, azetidine, or pyrrolidine, each optionally substituted by halo, $R^6$, oxo, —S(O)$_m$R$^6$, —SO$_2$NR$^6$R$^7$, —C(O)R$^b$, —C(O)NR$^6$R$^7$, —C(O)—C(O)NR$^6$R$^7$, —C(O)OR$^6$, or —C(O)—C(O)OR$^6$;
wherein each $R^6$, $R^7$, and $R^b$ is independently $C_{0-5}$alkyl or $C_{3-6}$cycloalkyl, each independently optionally substituted by halo, —OCF$_3$, or —OC$_{0-3}$alkyl; or NR$^6$R$^7$ defines a $_{4-7}$heterocycloalkyl optionally substituted by $C_{1-6}$alkyl; and m is 0-2.

In some aspects, the present invention concerns compounds and salts thereof of Formula I, more specifically having the formula:

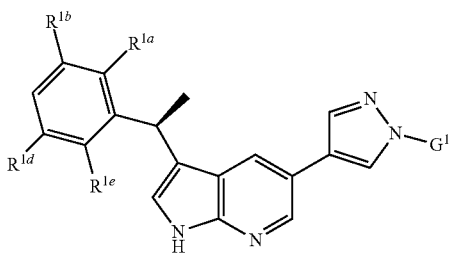

wherein $R^{1a}$ and $R^{1e}$ are both Cl;
each $R^{1b}$ and $R^{1d}$ is independently H, F, or —OCH$_3$;
$G^1$ is $_{3-6}$cycloalkyl substituted by 0-2 substituents independently selected from —OH, —OR$^6$, oxo, —S(O)$_m$R$^6$, —SO$_2$NR$^6$R$^7$, —C(O)R$^b$, —C(O)NR$^6$R$^7$, —C(O)—C(O)NR$^6$R$^7$, —C(O)OR$^6$, —C(O)—C(O)OR$^6$, or —C$_{1-3}$alkyl which alkyl can be substituted by halo or —OC$_{0-5}$alkyl;
wherein each $R^6$, $R^7$, and $R^b$ is independently $C_{0-5}$ alkyl or $C_{3-6}$cycloalkyl; or NR$^6$R$^7$ defines a $_{4-7}$heterocycloalkyl optionally substituted by $C_{1-6}$alkyl; and m is 0-2.

In some aspects, the present invention concerns compounds and salts thereof of Formula I, more specifically having the formula:

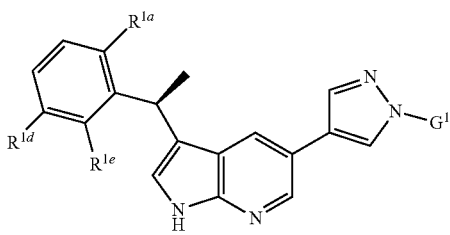

wherein $R^{1a}$ and $R^{1e}$ are both Cl;
$R^{1d}$ is F or —OCH$_3$;
$G^1$ is $_{3-6}$cycloalkyl substituted by 0-2 substituents independently selected from —OH, —OR$^6$, oxo, —S(O)$_m$R$^6$, —SO$_2$NR$^6$R$^7$, —C(O)R$^b$, —C(O)NR$^6$R$^7$, —C(O)—C(O)NR$^6$R$^7$, —C(O)OR$^6$, —C(O)—C(O)OR$^6$, or —C$_{1-3}$alkyl which alkyl can be substituted by halo or —OC$_{0-5}$alkyl;
wherein each $R^6$, $R^7$, and $R^b$ is independently $C_{0-5}$ alkyl or $C_{3-6}$cycloalkyl; or NR$^6$R$^7$ defines a $_{4-7}$heterocycloalkyl optionally substituted by $C_{1-6}$alkyl; and m is 0-2.

In some aspects, the present invention concerns compounds and salts thereof of Formula I, more specifically having the formula:

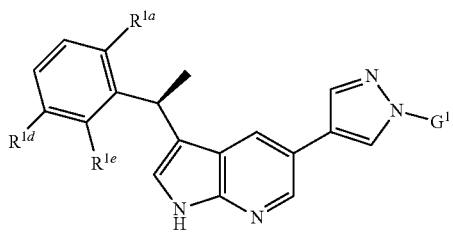

wherein $R^{1a}$ and $R^{1e}$ are both Cl;
$R^{1d}$ is F;
$G^1$ is $_{3-6}$cycloalkyl substituted by 0-2 substituents independently selected from —OH, —OR$^6$, oxo, —S(O)$_m$R$^6$, —SO$_2$NR$^6$R$^7$, —C(O)R$^b$, —C(O)NR$^6$R$^7$, —C(O)—C(O)NR$^6$R$^7$, —C(O)OR$^6$, —C(O)—C(O)OR$^6$, or —C$_{1-3}$alkyl which alkyl can be substituted by halo or —OC$_{0-3}$alkyl;
wherein each $R^6$, $R^7$, and $R^b$ is independently $C_{0-5}$alkyl or $C_{3-6}$cycloalkyl; or NR$^6$R$^7$ defines a $_{4-7}$heterocycloalkyl optionally substituted by $C_{1-6}$alkyl; and m is 0-2.

In some aspects, the present invention concerns compounds and salts thereof of Formula I, more specifically having the formula:

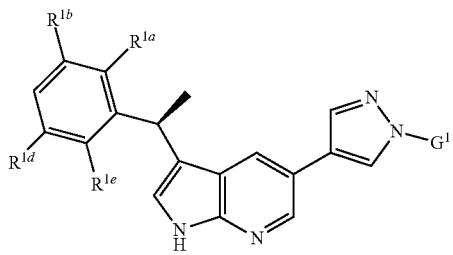

wherein $R^{1a}$ and $R^{1e}$ are both Cl;
each $R^{1b}$ and $R^{1d}$ is independently H, F, or —OCH$_3$;
$G^1$ is $C_{1-6}$alkyl substituted by 0-2 substituents independently selected from —OH, —OR$^6$, —R$^6$, oxo, —NR$^6$R$^7$, —C(O)R$^b$, —C(O)NR$^6$R$^7$, —C(O)—C(O)NR$^6$R$^7$, —C(O)OR$^6$, —C(O)—C(O)OR$^6$, —OC(O)R$^b$, —NR$^6$C(O)R$^b$, —NR$^6$S(O)$_2$R$^7$, —(CR$^8$R$^9$)$_n$C(O)R$^b$, —(CR$^8$R$^9$)$_n$C(O)OR$^6$, —(CR$^8$R$^9$)$_n$C(O)NR$^6$R$^7$, —(CR$^8$R$^9$)$_n$S(O)$_2$NR$^6$R$^7$, —(CR$^8$R$^9$)$_n$NR$^6$R$^7$, —(CR$^8$R$^9$)$_n$OR$^6$, —(CR$^8$R$^9$)$_n$S(O)$_m$R$^6$, —NR$^{10}$C(O)NR$^6$R$^7$, —NR$^{10}$S(O)$_2$NR$^6$R$^7$, —NR$^{10}$S(O)NR$^6$R$^7$, or $_{4-7}$heterocycloalkyl optionally substituted by $C_{1-6}$alkyl;
wherein each $R^6$, $R^7$, $R^8$, $R^9$, $R^{10}$, and $R^b$ is independently $C_{0-5}$ alkyl or $C_{3-6}$cycloalkyl; or NR$^6$R$^7$ defines a $_{4-7}$heterocycloalkyl optionally substituted by $C_{1-6}$alkyl;
m is 0-2; and each n is independently 0-2.

In some aspects, the present invention concerns compounds and salts thereof of Formula I, more specifically having the formula:

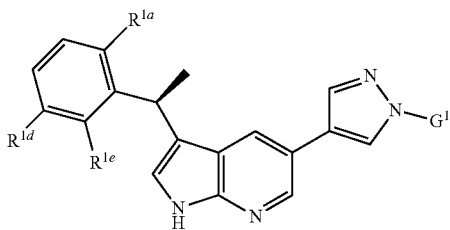

wherein $R^{1a}$ and $R^{1e}$ are both Cl;

$R^{1d}$ is F or —OCH$_3$;

G$^1$ is C$_{1-6}$alkyl substituted by 0-2 substituents independently selected from —OH, —OR$^6$, —R$^6$, oxo, —NR$^6$R$^7$, —C(O)R$^b$, —C(O)NR$^6$R$^7$, —C(O)—C(O)NR$^6$R$^7$, —C(O)OR$^6$, —C(O)—C(O)OR$^6$, —OC(O)R$^b$, —NR$^6$C(O)R$^b$, —NR$^6$S(O)$_2$R$^7$, —(CR$^8$R$^9$)$_n$C(O)R$^b$, —(CR$^8$R$^9$)$_n$C(O)OR$^6$, —(CR$^8$R$^9$)$_n$C(O)NR$^6$R$^7$, —(CR$^8$R$^9$)$_n$S(O)$_2$NR$^6$R$^7$, —(CR$^8$R$^9$)$_n$NR$^6$R$^7$, —(CR$^8$R$^9$)$_n$OR$^6$, —(CR$^8$R$^9$)$_n$S(O)$_m$R$^6$, —NR$^{10}$C(O)NR$^6$R$^7$, —NR$^{10}$S(O)$_2$NR$^6$R$^7$, —NR$^{10}$S(O)NR$^6$R$^7$, or $_{4-7}$heterocycloalkyl optionally substituted by C$_{1-6}$alkyl;

wherein each R$^6$, R$^7$, R$^8$, R$^9$, R$^{10}$, and R$^b$ is independently C$_{O5}$ alkyl or C$_{3-6}$cycloalkyl; or NR$^6$R$^7$ defines a $_{4-7}$heterocycloalkyl optionally substituted by C$_{1-6}$alkyl;

m is 0-2; and each n is independently 0-2.

In some aspects, the present invention concerns compounds and salts thereof of Formula I, more specifically having the formula:

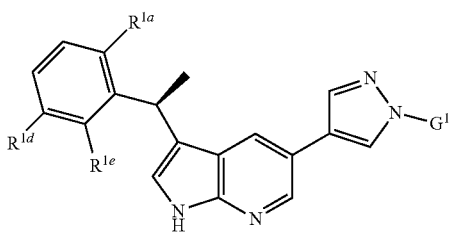

wherein $R^{1a}$ and $R^{1e}$ are both Cl;

$R^{1d}$ is F;

G$^1$ is C$_{1-6}$alkyl substituted by 0-2 substituents independently selected from —OH, —OR$^6$, —R$^6$, oxo, —NR$^6$R$^7$, —C(O)R$^b$, —C(O)NR$^6$R$^7$, —C(O)—C(O)NR$^6$R$^7$, —C(O)OR$^6$, —C(O)—C(O)OR$^6$, —OC(O)R$^b$, —NR$^6$C(O)R$^b$, —NR$^6$S(O)$_2$R$^7$, —(CR$^8$R$^9$)$_n$C(O)R$^b$, —(CR$^8$R$^9$)$_n$C(O)OR$^6$, —(CR$^8$R$^9$)$_n$C(O)NR$^6$R$^7$, —(CR$^8$R$^9$)$_n$S(O)$_2$NR$^6$R$^7$, —(CR$^8$R$^9$)$_n$NR$^6$R$^7$, —(CR$^8$R$^9$)$_n$OR$^6$, —(CR$^8$R$^9$)$_n$S(O)$_m$R$^6$, —NR$^{10}$C(O)NR$^6$R$^7$, —NR$^{10}$S(O)$_2$NR$^6$R$^7$, —NR$^{10}$S(O)NR$^6$R$^7$, or $_{4-7}$heterocycloalkyl optionally substituted by C$_{1-6}$alkyl;

wherein each R$^6$, R$^7$, R$^8$, R$^9$, R$^{10}$, and R$^b$ is independently C$_{0-3}$ alkyl or C$_{3-6}$cycloalkyl; or NR$^6$R$^7$ defines a $_{4-7}$heterocycloalkyl optionally substituted by C$_{1-6}$alkyl;

m is 0-2; and each n is independently 0-2.

In some aspects, the present invention concerns compounds and salts thereof of Formula I, more specifically having the formula:

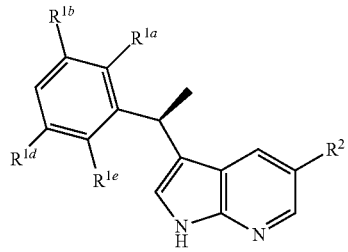

wherein $R^{1a}$ and $R^{1e}$ are each independently selected from halo, —CN, C$_{1-6}$alkyl, —CF$_3$, —OCF$_3$, or —OC$_{1-6}$alkyl;

$R^{1b}$ and $R^{1d}$ are each independently selected from H, halo, —CN, C$_{1-6}$alkyl, —CF$_3$, —OCF$_3$, or —OC$_{1-6}$alkyl;

R$^2$ is phenyl or pyridinyl, each substituted by G$^1$;

G$^1$ is $_{4-7}$heterocycloalkyl optionally substituted with halogen, —OH, —OCH$_3$, or C$_{1-3}$alkyl;

or G$^1$ is —C(O)NR$^6$R$^7$; and each R$^6$ and R$^7$ is independently C$_{0-3}$ alkyl or C$_{3-6}$cycloalkyl; or NR$^6$R$^7$ defines a $_{4-7}$heterocycloalkyl optionally substituted by C$_{1-6}$alkyl.

In some aspects, the present invention concerns compounds and salts thereof of Formula I, more specifically having the formula:

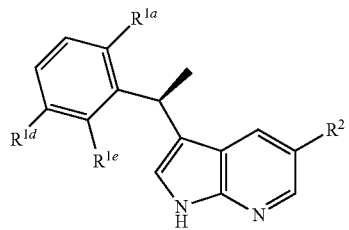

wherein $R^{1a}$ and $R^{1e}$ are both Cl;

$R^{1d}$ is F or methoxy;

R$^2$ is selected from

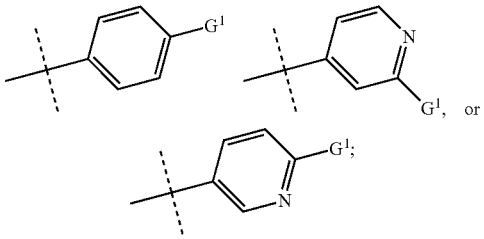

and G$^1$ is selected from piperazine, homopiperazine, morpholine, piperidine, azetidine, or pyrrolidine, each optionally substituted with halogen, —OH, —OCH$_3$, or C$_{1-3}$alkyl or C$_{3-6}$cycloalkyl.

In some aspects, the present invention concerns compounds and salts thereof of Formula I, more specifically having the formula:

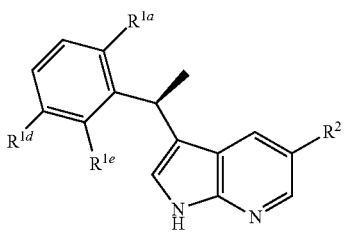

wherein $R^{1a}$ and $R^{1e}$ are both Cl;
$R^{1d}$ is F or methoxy;
$R^2$ is selected from

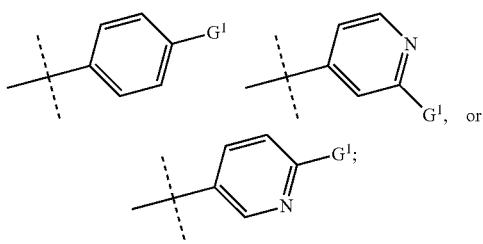

$G^1$ is $NR^6R^7$;
wherein each $R^6$ and $R^7$ is independently $C_{0-3}$ alkyl or $C_{3-6}$cycloalkyl; or $NR^6R^7$ defines a ring selected from piperazine, homopiperazine, morpholine, piperidine, azetidine, or pyrrolidine, each optionally substituted with halogen, —OH, —OCH$_3$, $C_{1-3}$alkyl, or $C_{3-6}$cycloalkyl.

In some aspects, the present invention concerns compounds and salts thereof of Formula I, more specifically having the formula:

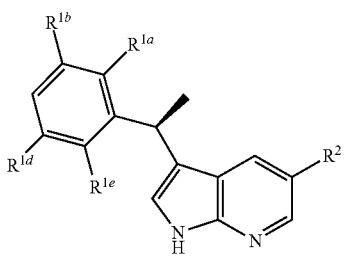

wherein $R^{1a}$ and $R^{1e}$ are each independently selected from halo, —CN, $C_{1-6}$alkyl, —CF$_3$, —OCF$_3$, or —OC$_{1-6}$alkyl;
$R^{1b}$ and $R^{1d}$ are each independently selected from H, halo, —CN, $C_{1-6}$alkyl, —CF$_3$, —OCF$_3$, or —OC$_{1-6}$alkyl;
$R^2$ is selected from

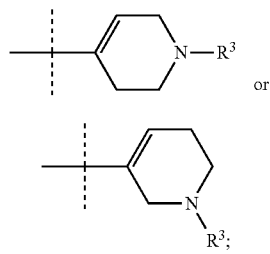

wherein $R^3$ is selected from —R$^4$, —C(O)R$^a$, R$^4$O—C$_{0-12}$alkylC(O)—, R$^4$R$^5$N—C$_{0-12}$alkylC(O)—, —CO$_2$R$^4$, —C(O)NR$^4$R$^5$, —S(O)$_m$R$^4$, —SO$_2$NR$^4$R$^5$, or —C(S)OR$^4$);
each R$^a$, R$^4$, and R$^5$ is independently C$_{0-3}$alkyl or C$_{3-6}$cycloalkyl; or NR$^4$R$^5$ defines a $_{4-7}$heterocycloalkyl optionally substituted by C$_{1-6}$alkyl;
each m is independently 0-2.

Each variable definition above includes any subset thereof and the compounds of Formula I include any combination of such variables or variable subsets.

In some aspects, the invention includes a compound of Formula I or a pharmaceutically acceptable salt thereof, in any of the above recitations, which further exhibits inhibition of c-MET in a cellular assay with an IC$_{50}$ of about 100 nM or less.

In some aspects, the invention includes a compound of Formula I or a pharmaceutically acceptable salt thereof, in any of the above recitations, which further exhibits inhibition of Ron in a cellular assay with an IC$_{50}$ of about 200 nM or less.

In some aspects, the invention includes a compound of Formula I or a pharmaceutically acceptable salt thereof, in any of the above recitations, which further exhibits inhibition of c-MET in a cellular assay with an IC$_{50}$ of about 100 nM or less and inhibition of Ron in a cellular assay with an IC$_{50}$ of about 200 nM or less.

In some aspects, the invention includes a compound of Formula I or a pharmaceutically acceptable salt thereof, in any of the above recitations, which further exhibits inhibition of c-MET in a cellular assay with an IC$_{50}$ of about 100 nM or less and inhibition of Ron in a cellular assay with an IC$_{50}$ of about 200 nM or less, and which is about 10-fold or more selective for c-MET over KDR.

In some aspects, the invention includes any of the compound examples herein and pharmaceutically acceptable salts thereof.

The invention includes the compounds and salts thereof, and their physical forms, preparation of the compounds, useful intermediates, and pharmaceutical compositions and formulations thereof.

Compounds described can contain one or more asymmetric centers and may thus give rise to stereoisomers. The present invention includes any stereoisomers, even if not specifically shown, individually as well as mixtures, geometric isomers, and pharmaceutically acceptable salts thereof. Where a compound or stereocenter is described or shown without definitive stereochemistry, it is to be taken to embrace all possible isomers and mixtures thereof. Thus, a material sample containing a mixture of stereoisomers would be embraced by a recitation of either of the stereoisomers or a recitation without definitive stereochemistry. Also contemplated are any cis/trans isomers or tautomers of the compounds described.

Further, the compounds may be amorphous or may exist or be prepared in various crystal forms or polymorphs, including solvates and hydrates. A recitation of a compound per se is taken to embrace that compound regardless of any unspecified stereochemistry, physical form and whether or not associated with solvent or water. A recitation of a compound also includes any isotopes thereof.

When a tautomer of the compound of Formula (I) exists, the compound of formula (I) of the present invention includes any possible tautomers and pharmaceutically acceptable salts thereof, and mixtures thereof, except where specifically stated otherwise.

The invention includes the intermediates and synthetic methods described herein.

General Synthesis

The compounds of the Formula I may be prepared by the methods described below, together with synthetic methods known in the art of organic chemistry, or modifications and derivatizations that are familiar to those of ordinary skill in the art. The starting materials used herein are commercially available or may be prepared by routine methods known in the art (such as those methods disclosed in standard reference books such as the COMPENDIUM OF ORGANIC SYNTHETIC METHODS, Vol. I-VI (published by Wiley-Interscience)). Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991, and T. W. Greene and P. G. M. Wuts, Protective Groups in Organic Chemistry, John Wiley & Sons, 1999, which are hereby incorporated by reference.

Compounds of Formula I, or their pharmaceutically acceptable salts, can be prepared according to the reaction Schemes discussed hereinbelow and the general skill in the art. Unless otherwise indicated, the substituents in the Schemes are defined as above. Isolation and purification of the products is accomplished by standard procedures, which are known to a chemist of ordinary skill. In the following general descriptions, $R^1$ indicates one or more substituents $R^{1a}$-$R^{1e}$.

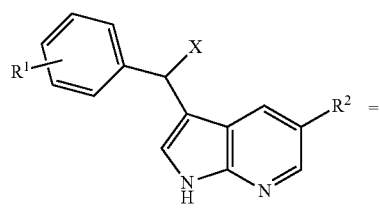

Formula I

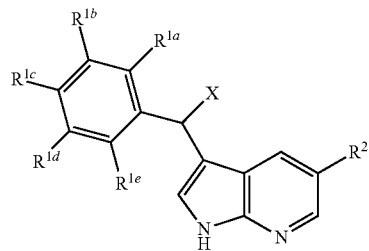

Scheme 1

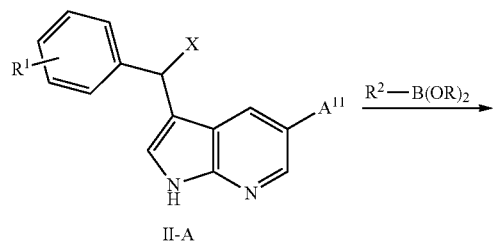

II-A

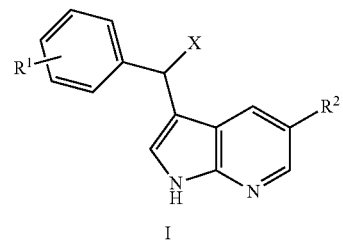

I

Compounds of Formula I can be prepared from II-A as in Scheme 1, wherein $R^1$ and $R^2$ are as defined previously and $A^{11}$ is halogen such as Cl, Br, or I and $B(OR)_2$ is a suitable boronic acid/ester. In a typical preparation of compounds of Formula I, a compound of Formula II-A is reacted with a suitable boronic acid/ester ($R^2$—$B(OR)_2$) in a suitable solvent via typical Suzuki coupling procedures. Suitable solvents for use in the above process include, but are not limited to, ethers such as THF, glyme, dioxane, dimethoxyethane, and the like; DMF; DMSO; MeCN; alcohols such as MeOH, EtOH, isopropanol, trifluoroethanol, and the like; and chlorinated solvents such as DCM or chloroform ($CHCl_3$). If desired, mixtures of these solvents can be used; however, preferred solvents are dimethoxyethane/water and dioxane/water. The above process can be carried out at temperatures between about −78° C. and about 120° C. Preferably, the reaction is carried out between 60° C. and about 100° C. The above process is preferably carried out at about atmospheric pressure although higher or lower pressures can be used. Substantially equimolar amounts of reactants are preferably used although higher or lower amounts can be used. One skilled in the art will appreciate that alternative methods may be applicable for preparing compounds of Formula I from II-A. For example, compound of Formula II-A could be reacted with a suitable organotin reagent $R^2$—$SnBu_3$ or the like in a suitable solvent via typical Stille coupling procedures.

Scheme 2

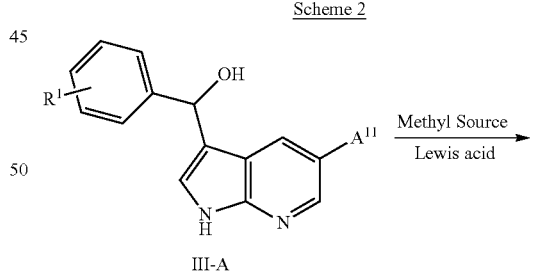

III-A

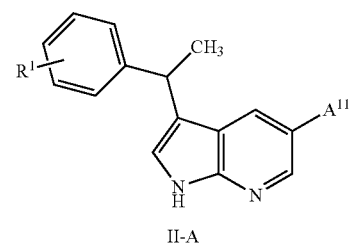

II-A

Compounds of Formula II-A can be prepared as in Scheme 2, wherein $R^1$ is as defined previously and $A^{11}$ is halogen such as Cl, Br, or I. In a typical preparation III-A can be reacted with a suitable methyl source in the presence of a Lewis acid in a suitable solvent. Suitable methyl source for use in the above process include, but are not limited to Me₃Al, Me₂Zn, Me₂AlCl, methyl Grignard reagents. A preferred methyl source is Me₂Zn. The methyl source may also be generated in situ, such as by reacting a methyl Grignard reagent with zinc chloride and using the resulting reagent without isolation for the above process. Suitable Lewis acids for use in the above process include, but are not limited to BF₃.OEt₂, AlCl₃, TiCl₄, and the like. A preferred Lewis acid is BF₃.OEt₂. Suitable solvents for use in the above process include, are not limited to, ethers such as THF, glyme, and the like; DMF; DMSO; MeCN; toluene; cyclohexane, and chlorinated solvents such as DCM or chloroform (CHCl₃). If desired, mixtures of these solvents can be used; however, a preferred solvent is THF. The above process can be carried out at temperatures between about −78° C. and about 120° C. Preferably, the reaction can be carried out between 40° C. and about 70° C. An excess amount of the methyl source and Lewis acid are preferably used.

Compounds similar to those of Formula III-A wherein the hydroxy group is replaced with an alkoxy group may also be used for the above process using the same Lewis acids and methyl source.

Compounds similar to those of Formula II-A wherein the methyl group is replaced by an alkyl group can be prepared by replacing the methyl source with an alkyl source under otherwise similar reaction conditions. For example, an ethyl group may be introduced using reagents such as Et₂Zn, and a propyl group may be introduced using reagents such as PrZnBr.

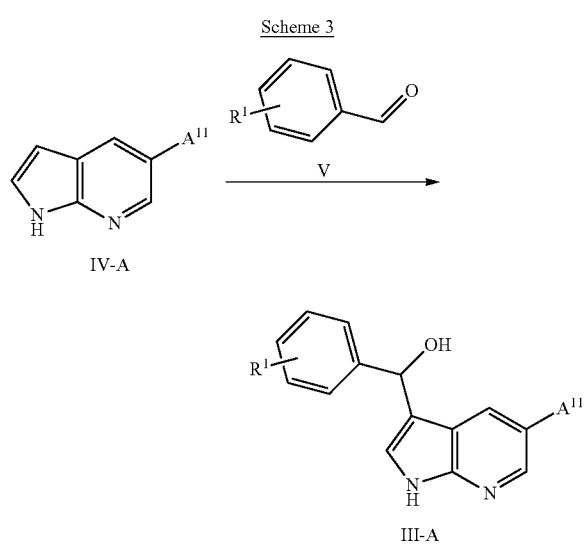

Compounds of Formula III-A can be prepared as in Scheme 3, wherein R¹ is as defined previously and A¹¹ is halogen such as Cl, Br, or I. In a typical preparation, IV-A is treated with benzaldehyde V in a suitable solvent in the presence of a suitable base at a suitable reaction temperature. Suitable solvents for use in the above process include, but are not limited to, ethers such as THF, glyme, and the like; DMF; DMSO; MeCN; chlorinated solvents such as DCM or chloroform (CHCl₃); and alcohols such as MeOH, EtOH, isopropanol, or trifluoroethanol. If desired, mixtures of these solvents can be used or no solvent can be used. A preferred solvent is MeOH. Suitable bases for use in the above process include, but are not limited to, KOH, NaOH, LiOH, KOtBu, NaOtBu and NaHMDS and the like. A preferred base is KOH. The above process can be carried out at temperatures between about −78° C. and about 120° C. Preferably, the reaction is carried out between 20° C. and about 60° C. The above process to produce compounds of the present invention is preferably carried out at about atmospheric pressure although higher or lower pressures can be used. Substantially equimolar amounts of reactants are preferably used although higher or lower amounts can be used.

When alcohols are used as solvent, analogs of compounds of Formula III-A wherein the hydroxyl group is replaced with an alkoxy group can also be obtained. For example, with MeOH as solvent one can obtain the methoxy analogs.

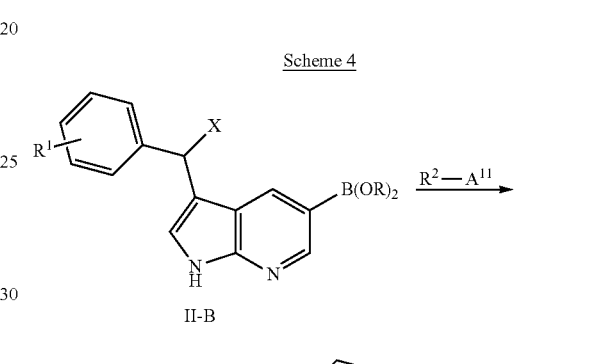

Compounds of Formula I can be prepared as in Scheme 4, wherein R¹ and R² are as defined previously, A¹¹ is halogen such as Cl, Br, or I, and B(OR)₂ is a suitable boronic acid/ester. Compound II-B can be reacted with a suitable coupling partner (R²-A¹¹)ₗₙ ₐ suitable solvent via typical Suzuki coupling procedures. Suitable solvents for use in the above process include, but are not limited to, ethers such as THF, glyme, dioxane, dimethoxyethane, and the like; DMF; DMSO; MeCN; alcohols such as MeOH, EtOH, isopropanol, trifluoroethanol, and the like; and chlorinated solvents such as DCM or chloroform (CHCl₃). If desired, mixtures of these solvents can be used, however, a preferred solvent is dimethoxyethane/water. The above process can be carried out at temperatures between about −78° C. and about 120° C. Preferably, the reaction is carried out between 60° C. and about 100° C. The above process is preferably carried out at about atmospheric pressure although higher or lower pressures can be used. Substantially, equimolar amounts of reactants are preferably used although higher or lower amounts can be used if desired.

One skilled in the art will appreciate that alternative methods may be applicable for preparing compounds of Formula I from R²-A¹¹, e.g., via typical Stille coupling procedures.

Scheme 5

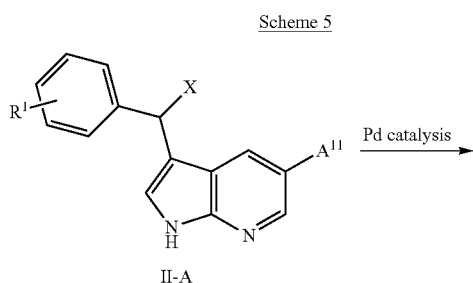

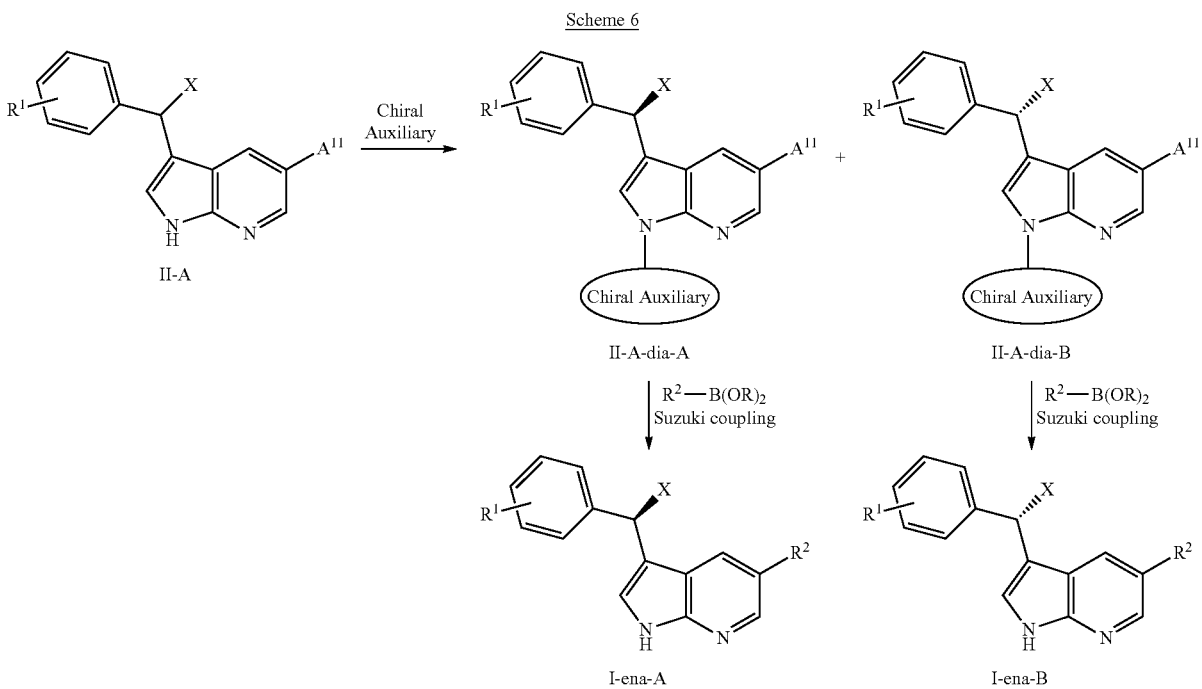

-continued

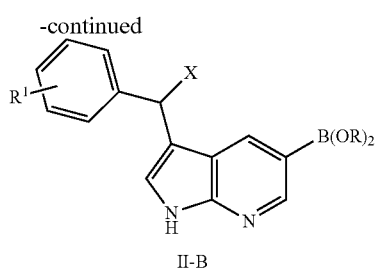

II-B

Compounds of Formula II-B can be prepared as in Scheme 5, wherein $R^1$ is as defined previously, $A^{11}$ is halogen such as Cl, Br, or I, and $B(OR)_2$ is a suitable boronic acid/ester. In a typical preparation a compound of Formula II-A can be reacted with a suitable coupling partner (Bis(pinacolato)diboron or Pinacolborane)) in a suitable solvent under Palladium catalysis. Suitable solvents for use in the above process include, but are not limited to, ethers such as THF, glyme, dioxane, dimethoxyethane, and the like; DMF; DMSO; MeCN; alcohols such as MeOH, EtOH, isopropanol, trifluoroethanol, and the like; and chlorinated solvents such as DCM or chloroform ($CHCl_3$). If desired, mixtures of these solvents can be used; however, a preferred solvent is THF or dioxane. The above process can be carried out at temperatures between about −78° C. and about 120° C. Preferably, the reaction is carried out between 60° C. and about 100° C. The above process is preferably carried out at about atmospheric pressure although higher or lower pressures can be used. Substantially equimolar amounts of reactants used although higher or lower amounts can be used if desired.

One skilled in the art will appreciate that alternative methods may be applicable for preparing compounds of Formula II-B. For example, via halogen-metal exchange (for example, halogen-Lithium exchange) and quench with borylation reagents such as tri-isopropyl borate.

Chiral resolution: Compounds of Formula I have the carbon chiral center shown in Scheme 6. The enantiomerically pure isomers I-ena-A and I-ena-B can be prepared by a chiral resolution through a chemical reaction which leads to two diastereomers II-A-dia-A and II-A-dia-B. After separation of these two diastereomers by flash chromatography or crystallization, each diastereomer can be subjected to a Suzuki coupling as shown in Scheme 6 to produce I-ena-A and I-ena-B individually.

In a typical preparation of II-A-dia-A and II-A-dia-B, a compound of Formula II-A is reacted with a chiral auxiliary in the presence of a coupling reagent to provide both II-A-dia-A and II-A-dia-B, which are separated by chromatography. Suitable chiral auxiliaries for use in the above process include, but are not limited to amino acids and their derivatives, (1S)-(+)-camphor-10-sulfonic acid, (1R)-(−)-camphor-10-sulfonic acid and the like. However, a preferred chiral auxiliary is Fmoc-L-Leucine. Suitable solvents for use in the above process included, but are not limited to, ethers such as THF, glyme, dioxane, dimethoxyethane, and the like; DMF; DMSO; MeCN; alcohols such as MeOH, EtOH, isopropanol, trifluoroethanol, and the like; and chlorinated solvents such as DCM or chloroform ($CHCl_3$). If desired, mixtures of these solvents can be used, however, a preferred solvent is DMF. The suitable coupling reagents for use in the above process include, but are not limited to DCC, EDC, TBTU, HBTU and the like. A preferred coupling reagent is TBTU. The above process can be carried out at temperatures between about −78° C. and about 120° C. Preferably, the reaction is carried out between 0° C. and about 60° C. The above process is preferably carried out at about atmospheric pressure although higher or lower pressures can be used if desired. Substantially equimolar amounts of reactants are preferably used although higher or lower amounts can be used if desired.

After purification and separation, both II-A-dia-A and II-A-dia-B are reacted separately with a suitable boronic acid/ester ($R^2$—$B(OR)_2$), to provide both I-ena-A and I-ena-B, via typical Suzuki coupling procedures as in Scheme 1.

One skilled in the art will appreciate that instead of covalently attaching a chiral auxiliary to compound II-A one may form diastereomeric salts that may be separated by crystallization. Neutralization of the separated diastereomeric salts provides the separated enantiomers of II-A. Suitable chiral auxiliaries include, but are not limited to amino acids and their derivatives, (1S)-(+)-camphor-10-sulfonic acid, (1R)-(−)-camphor-10-sulfonic acid and the like.

of a given compound. For example, Group $R^2$ can be installed on compound IV-A under conditions similar to Schemes 1, 5, and 4. The resulting compound can be treated with an appropriate benzaldehyde under conditions similar to Scheme 3, followed by introduction of a methyl group similar to Scheme 2. Moreover, in the foregoing syntheses, pyrrolo[2,3-b]pyrazine cores can be substituted for the depicted pyrrolopyridines.

A skilled artisan will realize that the reactions shown in Schemes 1, 4-7 can be conducted under similar conditions with compounds in which the methyl group shown is replaced by other alkyl or alkoxy groups within the scope defined for the variable X.

Preparations

Unless otherwise noted, all materials/reagents were obtained from commercial suppliers and used without further purification. $^1$H NMR (400 MHz or 300 MHz) and $^{13}$C NMR (100.6 MHz) spectra were recorded on Bruker or Varian instruments at ambient temperature with tetramethylsilane or the residual solvent peak as the internal standard. The line positions or multiples are given in ppm (δ) and the coupling constants (J) are given as absolute values in Hertz (Hz). The multiplicities in $^1$H NMR spectra are abbreviated as follows:

Scheme 7

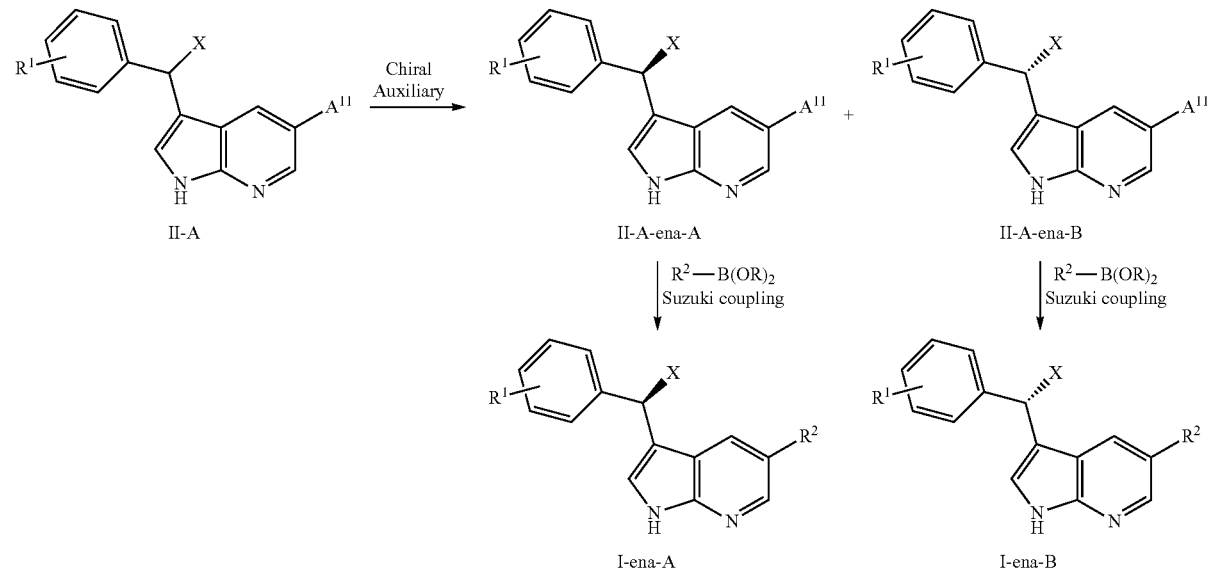

Alternatively, the enantiomerically pure isomers I-ena-A and I-ena-B can be prepared as in Scheme 7 individually from corresponding enantiomerically pure II-A-ena-A and II-A-ena-B through Suzuki coupling reactions. Enantiomerically pure II-A-ena-A and II-A-ena-B can be prepared from separation of racemic mixture II-A by a chiral chromatography as in Scheme 7.

The suitable system for separation of II-A-ena-A and II-A-ena-B by chromatography can be, but is not limited to, chiral HPLC (high performance liquid chromatography) systems, chiral SFC (supercritical fluid chromatography) systems and the like. After separation, both II-A-ena-A and II-A-ena-B can be reacted individually with a suitable boronic acid/ester ($R^2$—$B(OR)_2$), to provide both I-ena-A and I-ena-B, via typical Suzuki coupling procedures as in Scheme 1.

As will be apparent to the skilled artisan, the synthetic route/sequence can be modified as desired for the preparation s (singlet), d (doublet), t (triplet), q (quartet), quint (quintet), m (multiplet), $m_c$ (centered multiplet), br or broad (broadened), AA'BB'. The signal multiplicities in $^{13}$C NMR spectra were determined using the DEPT135 pulse sequence and are abbreviated as follows: +(CH or CH$_3$), —(CH$_2$), $C_{quart}$ (C). Reactions were monitored by thin layer chromatography (TLC) on silica gel 60 $F_{254}$ (0.2 mm) precoated aluminum foil and visualized using UV light. Flash chromatography was performed with silica gel (400–230 mesh). Preparatory TLC was performed on Whatman LK6F Silica Gel 60 Å size 20×20 cm plates with a thickness of 500 or 1000 μm. Hydromatrix (=diatomaceous earth) was purchased from Varian. Mass-directed HPLC purification of compounds was performed on a Waters system composed of the following: 2767 Sample Manager, 2525 Binary Gradient Module, 600 Controller, 2996 Diode Array Detector, Micromass ZQ2000 for ionization, Phenomenex Luna 5μ, C18(2) 100 Å 150×21.2 mm 5μ, column with mobile phases of 0.01% Formic Acid Acetonitrile (A) and 0.01% Formic Acid in HPLC water (B), a flow rate of 20 mL/min, and a run time of 13 min. LC-MS data was collected on ZQ2, ZQ3, or HPLC-ACQUITY. ZQ2 is an Agilent 1100 HPLC equipped with a Gilson 215 Liquid Handler, Gilson 819 Injection Module, and Waters Micromass ZQ2000 for ionization. ZQ3 is an Agilent 1100 HPLC equipped with an HP Series 1100 auto injector and Waters Micromass ZQ2000 for ionization. Both systems use the Xterra MS C18, 5μ, particle size, 4.6×50 mm with a mobile phase of Acetonitrile (A) and 0.01% Formic Acid in HPLC water (B). The flow rate is 1.3 mL/min, the run time is 5 min, and the gradient profiles are 0.00 min 5% A, 3.00 min 90% A, 3.50 min 90% A, 4.00 min 5% A, 5.00 min 5% A for polar_5 min and 0.00 min 25% A, 3.00 min 99% A, 3.50 min 99% A, 4.00 min 25% A, 5.00 min 25% A for nonpolar_5 min. All Waters Micromass ZQ2000 instruments utilized electrospray ionization in positive (ES+) or negative (ES−) mode. The Waters Micromass ZQ2000 instruments from ZQ2 and ZQ3 can also utilize atmospheric pressure chemical ionization in positive (AP+) or negative (AP−) mode. The Waters HPLC-ACQUITY system consists of an ACQUITY sample manager attached to ACQUITY SQ MS and ACQUITY PDA detectors. It uses an ACQUITY HPLC BEH® C18 2.1×50 mm 1.7 μm column with a mobile phase of 0.1% formic acid in water (A) and 0.1% formic acid in acetonitrile (B). The flow rate is 1.0 mL/min, run time is 2 min, and the gradient profile is 0.00 min 95% A, 1.50 min 1% A, 1.85 min 1% A, 2.0 min 95% A for analytical. UV detection is at 254 nm, and the MS utilizes electrospray ionization in positive mode (ES+). HPLC purification of compounds was performed on a Waters system consisting of a 2767 Sample Manager, 1525EF Binary Pump, and a 2487 Dual λ Absorbance Detector. The system uses Phenomenex Luna C18(2), 5μ particle size, 50×21.2 mm columns with a mobile phase of Acetonitrile/0.25% Formic Acid and HPLC water/0.25% Formic Acid. Alternatively, a Gilson system ("Gilson HPLC") consisting of a 215 Liquid Handler, 819 Injection Module, a 322 Pump, and a 155 UV/VIS dual wavelength detector set to 254 and 210 nm was used. This system uses Phenomenex Luna C18(2), 5μ particle size, 50×21.2 mm or 60×21.2 mm columns with a mobile phase of Acetonitrile and 0.1% Formic Acid in HPLC water. The flow rate is 15 mL/min and the run time is 25 min. The HPLC system for determination of enantiomeric purity consists of an Agilent 1100 HPLC and Chiralcel or Chiralpak 4.6×150 mm columns (Daicel Chemical Ind., Ltd.), eluting with acetonitrile/water mixtures. All melting points were determined with a Mel-Temp II apparatus and are uncorrected. Elemental analyses were obtained by Atlantic Microlab, Inc., Norcross, Ga.

5-Bromo-3-[1-(2,6-dichloro-3-fluorophenyl)ethyl]-1H-pyrrolo[2,3-b]pyridine (5-Bromo-1H-pyrrolo[2,3-b]pyridin-3-yl)-(2,6-dichloro-3-fluorophenyl)methanol (5.05 g, 12.9 mmol) was dissolved in anhydrous THF (100 mL). To this solution was added $BF_3 \cdot OEt_2$ (10.66 mL, 6.5 eq.) at −78° C. The resulting solution was stirred for 10 min at the same temp before a solution of $ZnMe_2$ (35.60 mL, 5.5 eq., 2 N in toluene) was added. The resulting mixture was allowed to warm up to rt in 1 h. The solution was then stirred at 65° C. for 3.5 h. Reaction was monitored by LC-MS. After achieving >95% conversion, the reaction was allowed to cool down to rt. Then it was further cooled down to −78° C. and quenched by adding sat. aq. $NH_4Cl$ solution (10 mL). The mixture was slowly warmed up to rt. Solvents were removed under reduced pressure. To the residue was added aq. $NaHCO_3$ solution and the mixture was then extracted with $CHCl_3$ (100 mL×4). The organic extracts were combined, dried ($Na_2SO_4$), and concentrated in vacuo to give a crude residue which was purified by flash chromatography (eluent: 10% ethyl acetate in hexane). $^1H$ NMR (400 MHz. DMSO-$d_6$): δ=11.85 (br. s., 1H), 8.21 (d, J=2.0 Hz, 1H), 7.49-7.59 (m, 2H), 7.41 (dd, J=8.8, 8.6 Hz, 1H), 7.30 (d, J=2.0 Hz, 1H), 5.11 (q, J=7.3 Hz, 1H), 1.80 (d, J=7.3 Hz, 3H); $^{13}C$ NMR (100.6 MHz, DMSO-$d_6$): δ 156.74 ($J_{CF}$=247.4 Hz), 146.91, 142.24, 141.02, 129.37, 127.56, 125.98, 121.73 ($J_{CF}$=19.8 Hz), 120.18, 115.98 ($J_{CF}$=23.4 Hz), 113.62, 109.99, 33.53, 15.94. MS (ES+): m/z=386.93, 388.91, 390.89 [MH$^+$]. HPLC: $t_R$=4.17 min (ZQ3, polar_5 min).

(5-Bromo-1H-pyrrolo[2,3-b]pyridin-3-yl)-(2,6-dichloro-3-fluorophenyl)methanol

To a stirred mixture of 5-bromo-1H-pyrrolo[2,3-b]pyridine (0.100 g, 0.508 mmol) and 2,6-dichloro-3-fluorobenzaldehyde (0.107 g, 0.558 mmol) in MeOH (5 mL) was added potassium hydroxide (0.199 g, 3.553 mmol) at 0° C. under nitrogen atmosphere. The resulting mixture was then stirred at r.t. overnight. The mixture was then poured into water (50 mL), acidified with 2N HCl and extracted with ethyl acetate (50 mL×3). The organics were combined, dried ($Na_2SO_4$) and concentrated under reduced pressure to give a crude residue which was then purified by chromatography (eluent: 20% ethyl acetate in hexane). MS (ES+): m/z=388.85, 390.84, 392.83 [MH$^+$]. HPLC: $t_R$=3.29 min (ZQ3, polar_5 min).

5-Bromo-3-[1-(2,6-dichlorophenyl)ethyl]-1H-pyrrolo[2,3-b]pyridine

Prepared according to the method described above for synthesis of 5-bromo-3-[1-(2,6-dichloro-3-fluorophenylethyl]-1H-pyrrolo[2,3-b]pyridine, using (5-bromo-1H-pyrrolo[2,3-b]pyridin-3-yl)-(2,6-dichlorophenyl)methanol. MS (ES+): m/z 368.89, 370.86, 372.88 [MH$^+$]. HPLC: $t_R$=3.25 min (ZQ3, polar_5 min).

(5-Bromo-1H-pyrrolo[2,3-b]pyridin-3-yl)-(2,6-dichlorophenyl)methanol

Prepared according to the method described above for synthesis of (5-bromo-1H-pyrrolo[2,3-b]pyridin-3-yl)-(2,6-dichloro-3-fluorophenyl)methanol, using 2,6-dichloro-benzaldehyde. MS (ES+): m/z 370.85, 372.85, 374.83 [MH$^+$]; HPLC: $t_R$=3.25 min (ZQ3, polar_5 min).

3-[1-(2,6-Dichloro-3-fluorophenyl)ethyl]-5-(4,4,5,5-tetramethyl[1,3,2]dioxaborolan-2-yl)-1H-pyrrolo[2,3-b]pyridine To a stirred mixture of 5-bromo-3-[1-(2,6-dichloro-3-fluorophenyl)ethyl]-1H-pyrrolo[2,3-b]pyridine (500.0 mg, 1.288 mmol), potassium acetate (379 mg, 3.86 mmol), bis(pinacolato)diboron (425.3 mg, 1.675 mmol) in 1,4-dioxane (15 mL) was added (1,1'-bis-(diphenylphosphino)ferrocene) palladium dichloride (47.10 mg, 0.0644 mmol) under Nitrogen atmosphere. The mixture was then stirred at 85° C. overnight. LC-MS indicated completion of reaction. Solvents were then removed under reduced pressure to give a residue which was then purified by flash chromatography (eluent: 25% ethyl acetate in DCM). ¹H NMR (400 MHz, CD₃OD): δ=1.20 (s, 12H), 1.86 (d, J=7.3 Hz, 3H), 5.27 (q, J=7.0 Hz, 1H), 7.17 (t, J=8.7 Hz, 1H), 7.33 (d, J=1.3 Hz, 1H), 7.40 (br. s., 1H), 7.75 (d, J=1.5 Hz, 1H), 8.43 (d, J=1.5 Hz, 1H). MS (ES+): m/z=434.02, 435.06, 437.07, 438.11 [MH⁺]. HPLC: $t_R$=4.22 min (ZQ3, polar__5 min).

3-[(S)-1-(2,6-Dichloro-3-fluorophenyl)ethyl]-5-(4,4,5,5-tetramethyl[1,3,2]dioxaborolan-2-yl)-1H-pyrrolo[2,3-b]pyridine To a stirred mixture of 5-bromo-3-[(S)-1-(2,6-dichloro-3-fluorophenyl)ethyl]-1H-pyrrolo[2,3-b]pyridine (450.0 mg, 1.160 mmol), potassium acetate (341 mg, 3.48 mmol), bis(pinacolato)diboron (412 mg, 1.62 mmol) in 1,4-dioxane (10 mL) was added (1,1'-bis-(diphenylphosphino)ferrocene) palladium dichloride (70 mg, 0.090 mmol) under Nitrogen atmosphere. The mixture was then stirred at 80° C. overnight. Solvents were removed under reduced pressure to give a residue which was then redissolved in DCM and dry-loaded onto silica gel. Column chromatography was used to purify, eluting with 30-40% EtOAc/hexanes. The fractions containing the product were concentrated in vacuo to afford the title compound as yellow gum. ¹H NMR and LCMS data match with the data for the racemic compound.

((S)-1-{5-Bromo-3-[(S)-1-(2,6-dichloro-3-fluorophenyl)ethyl]pyrrolo[2,3-b]pyridine-1-carbonyl}-3-methylbutyl)carbamic acid 9H-fluoren-9-ylmethyl ester and ((S)-1-{5-Bromo-3-[(R)-1-(2,6-dichloro-3-fluorophenyl)ethyl]pyrrolo[2,3-b]pyridine-1-carbonyl}-3-methylbutyl)carbamic acid 9H-fluoren-9-ylmethyl ester

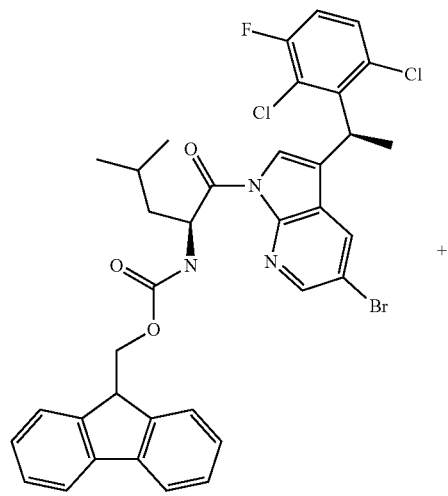

+

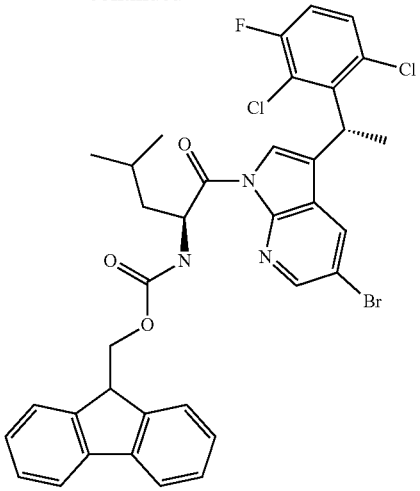

To a stirred mixture of 5-bromo-3-[1-(2,6-dichloro-3-fluorophenyl)ethyl]-1H-pyrrolo[2,3-b]pyridine (100.0 mg, 0.257 mmol), (S)-2-(9H-Fluoren-9-ylmethoxycarbonylamino)-4-methylpentanoic acid (Fmoc-L-Leucine) (136.6 mg, 0.386 mmol) in DMF (4.00 mL) were added DIPEA (0.224 mL, 1.28 mmol) and TBTU (124.1 mg, 0.386 mmol). The resulting mixture was stirred at rt for 16 h. Solvents were then removed under reduced pressure to give a residue which was purified by flash chromatography (eluent: Hexane/ethyl acetate/DCM: 100/3/25, v/v/v) to give both diastereomers as pure compounds.

More polar diastereomer: ((S)-1-{5-Bromo-3-[(S)-1-(2,6-dichloro-3-fluorophenyl)-ethyl]pyrrolo[2,3-b]pyridine-1-carbonyl}-3-methylbutyl)carbamic acid 9H-fluoren-9-ylmethyl ester. MS (ES+): m/z 722.06, 724.07, 726.03 [MH⁺], HPLC: $t_R$=3.76 min (ZQ3, very very non-polar__5 min). Less polar diastereomer: ((S)-1-{5-Bromo-3-[(R)-1-(2,6-dichloro-3-fluorophenyl)ethyl]pyrrolo[2,3-b]pyridine-1-carbonyl}-3-methylbutyl)carbamic acid 9H-fluoren-9-ylmethyl ester. MS (ES+): m/z 722.06, 724.07, 726.03 [MH⁺], HPLC: $t_R$=3.84 min (ZQ3, very very non-polar__5 min).

5-Bromo-3-[(S)-1-(2,6-dichloro-3-fluorophenyl)ethyl]-1H-pyrrolo[2,3-b]pyridine

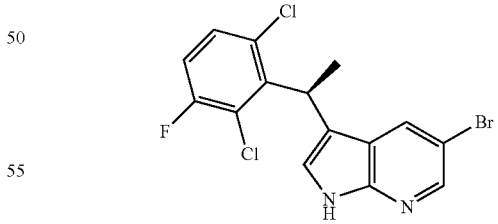

To a solution of ((S)-1-{5-Bromo-3-[(S)-1-(2,6-dichloro-3-fluorophenyl)ethyl]pyrrolo[2,3-b]pyridine-1-carbonyl}-3-methylbutyl)-carbamic acid 9H-fluoren-9-ylmethyl ester (722 mg, 1.00 mmol) in THF (20 mL) was added NaOH (5N in H₂O, 1 mL) at 0° C. with stirring. After stirring for 1 h at that temperature, solvents were removed under reduced pressure to give a residue which was then purified by flash chromatography (eluent: Hexane/ethyl acetate: 75/25, v/v) to give the title compound. ¹H NMR and LCMS data match with the data for the racemic compound. Optical rotation: $[\alpha]^{25}_D = -112.8°$ (c=1.0, MeOH); $[\alpha]^{25}_D = -152.6°$ (c=1.0, $CH_2Cl_2$). HPLC (Chiralcel OD-RH, solvent 60:40 acetonitrile/water isocratic, flow rate 0.5 mL/min, column temperature 30° C., UV detection at 220 nm): $t_R$=28.0 min. $C_{15}H_{10}BrCl_2FN_2$ (388.07): Calculated: C, 46.43; H, 2.60; Br, 20.59; Cl, 18.27; F, 4.90; N, 7.22. found C, 46.36; H, 2.49; Br, 20.38; Cl, 18.31; F, 4.79; N, 7.09. A crystal structure of Example 85, prepared using this material, bound to cMet confirmed the absolute configuration as shown.

5-Bromo-3-[(R)-1-(2,6-dichloro-3-fluorophenyl)ethyl]-1H-pyrrolo[2,3-b]pyridine

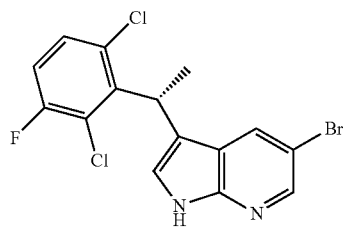 [SMILES: C[C@@H](c1c(Cl)ccc(F)c1Cl)c1c[nH]c2ncc(Br)cc12]

The procedure described above for the (S) enantiomer was followed, starting with ((S)-1-{5-Bromo-3-[(R)-1-(2,6-dichloro-3-fluorophenyl)ethyl]pyrrolo[2,3-b]pyridine-1-carbonyl}-3-methylbutyl)-carbamic acid 9H-fluoren-9-ylmethyl ester. $^1$H NMR and LCMS data match with the data for the racemic compound. Optical rotation: $[\alpha]^{25}_D = +115.7°$ (c=1.0, MeOH); $[\alpha]^{25}_D = +151.7°$ (c=1.0, $CH_2Cl_2$). HPLC (Chiralcel OD-RH, solvent 60:40 acetonitrile/water isocratic, flow rate 0.5 mL/min, column temperature 30° C., UV detection at 220 nm): $t_R$=32.1 min.

2,6-Dichloro-3-fluorobenzaldehyde

To a solution of (2,6-Dichloro-3-fluorophenyl)methanol (100 g, 0.51 mol) in dichloromethane (450 mL) was added a solution of sodium bromide (54 g, 0.53 mol, in 90 mL water). The rapidly stirred biphasic mixture was cooled to −7° C. and TEMPO (1.54 g, 0.0100 mol) was added. A solution of 0.81M sodium hypochlorite (823 mL, 0.66 mol) saturated with sodium bicarbonate (75 g) was added dropwise over a period of 1 h while maintaining the temperature below −2° C. After the addition the reaction mixture was stirred for 30 min. The two layers separated and the DCM layer was washed with aq. solution of sodium thiosulfate. The DCM layer was dried ($Na_2SO_4$) and concentrated on rotary evaporator without using vacuum (aldehyde is volatile) to give the title compound as a solid, mp. 63-65° C. $^1$H NMR ($CDCl_3$, 300 MHz): δ=7.23 (dd, 1H, J=7.8, 9.0 Hz), 7.35 (dd, 1H, J=4.5, 9.3 Hz), 10.2 (s, 1H).

Alternate preparation: To a solution of 2,4-dichloro-1-fluorobenzene (100 g, 0.606 mol) in THF (1.4 L) under nitrogen at −78° C., was added a 2.5 M solution of n-BuLi in hexanes (267 mL, 0.666 mol) dropwise over a period of 30 min, maintaining the temperature between −70 to −78° C. After 1.5 h stirring at −78° C., methyl formate (72.6 mL, 1.21 mol) was added slowly, and the reaction mixture was stirred overnight, warming up to rt. The reaction was quenched with sat. aqueous $NH_4Cl$ (200 mL) and the organic layer was separated. The organic solvents were removed by distillation at atmosphere pressure and the crude material which contained a small amount of THF was crystallized from hexanes to give the title compound.

(2,6-Dichloro-3-fluorophenyl)methanol

To a solution of 2,6-Dichloro-3-fluorobenzoic acid (125 g, 0.59 mol) in THF (200 mL) was added $BH_3$.THF (592 mL, 592 mmol, 1M solution in THF) dropwise at room temperature. The reaction mixture was heated to reflux for 12 h. The borane was quenched with methanol (200 mL) and the resulting solution was concentrated to dryness. The residue was again co-evaporated with methanol to remove most of the trimethylborate. To the residue was added aq. sodium carbonate (50 g in 500 mL). The mixture was cooled and a white fine precipitate was filtered off to give the title compound. $^1$H NMR ($CDCl_3$, 300 MHz): δ=2.10 (t, 1H, J=6.9 Hz), 4.96 (d, 2H, J=6.9 Hz), 7.09 (dd, 1H, J=8.1, 9.0 Hz), 7.29 (dd, 1H, J=4.8, 9.0 Hz).

2,6-Dichloro-3-fluorobenzoic acid

To a cooled (−5° C.) solution of sodium hydroxide (252 g, 6.3 mol) in water (800 mL) was added bromine (86 mL, 1.68 mol) dropwise. The temperature of the reaction mixture was kept below −5° C. during the addition. A solution of 1-(2,6-Dichloro-3-fluorophenyl)ethanone (100 g, 480 mmol) in dioxane (800 ml) was added to the solution of sodium hypobromide in 1 h while maintaining the temperature below 0° C. The reaction mixture was warmed to room temperature and stirred for 2 h. After the TLC showed absence of starting material, the excess sodium hypobromide was destroyed with sodium sulfite (100 g in 100 mL water). The resulting solution was heated to 90° C. for 2 h. The reaction mixture was acidified with conc. HCl with vigorous stirring. The acidic solution was concentrated to remove all the dioxane and then extracted with dichloromethane (2×500 mL). The organic layer was dried ($Na_2SO_4$) and concentrated to give an oily residue, which after trituration with hexanes gave the title compound as a white solid. $^1$H NMR ($CDCl_3$, 300 MHz): δ=7.20 (dd, 1H, J=8.7, 8.4 Hz), 7.33 (dd, 1H, J=9.3, 4.5 Hz).

EXAMPLES

Example 1

3-[1-(2,6-Dichlorophenyl)ethyl]-5-(1-piperidin-4-yl-1H-pyrazol-4-yl)-1H-pyrrolo[2,3-b]pyridine To a stirred mixture of 5-bromo-3-[1-(2,6-dichlorophenyl)ethyl]-1H-pyrrolo[2,3-b]-pyridine (10.00 mg, 0.027 mmol), 4-[4-(4,4,5,5-tetramethyl[1,3,2]dioxaborolan-2-yl)-pyrazol-1-yl]-piperidine hydrochloride (11.00 mg, 0.035 mmol), potassium carbonate (15.00 mg, 0.11 mmol) in DME (2.0 mL) and $H_2O$ (0.40 mL) was added (1,1'-bis-(diphenylphosphino)ferrocene)palladium dichloride (0.84 mg, 0.0011 mmol) under nitrogen atmosphere. The resulting mixture was refluxed at 100° C. for 90 min. The solvent was then removed under reduced pressure and the resulting residue was purified by a flash chromatography (eluent: 8% MeOH in DCM) to give desired product. $^1$H NMR (400 MHz, $CD_3OD$): δ=1.92 (d, J=7.1 Hz, 3H), 1.98-2.21 (m, 4H), 2.76-2.91 (m, 2H), 3.19-3.32 (m, 2H), 4.30-4.44 (m, 1H), 5.27-5.40 (m, 1H), 7.20-7.51 (m, 5H), 7.59 (s, 1H), 7.89 (s, 1H), 8.34 (d, J=2.0 Hz, 1H). MS (ES$^+$): m/z 440.06, 442.06 [MH$^+$]. HPLC: $t_R$=2.46 min (ZQ3, polar_5 min)

4-[4-(4,4,5,5-Tetramethyl[1,3,2]dioxaborolan-2-yl)pyrazol-1-yl]piperidine hydrochloride To a solution of 4-[4-(4,4,5,5-Tetramethyl-1,3,2-dioxaborolan-2-yl)pyrazol-1-yl]-piperidine-1-carboxylic acid tert-butyl ester (3.02 g, 8.00 mmol) in 1,4-dioxane (30 mL, 400 mmol), 4.0 M of HCl in 1,4-Dioxane (30 mL) was added and the reaction was stirred at 35° C. for 3 h. The reaction mixture was concentrated in vacuo to a white solid. The material was slightly hygroscopic. All free-flowing material was transferred to a vial and dried under vacuum for several hours. The material thus obtained was used in further reactions without purification. $^1$H NMR (400 MHz, CDCl$_3$): δ=1.33 (s, 12H), 2.49 (br s, 4H), 3.18 (br s, 2H), 3.59-3.70 (m, 2H), 4.71 (br s, 1H), 7.87 (s, 2H), 9.84 (br s, 2H). MS (ES+): m/z 278.11 (100) [MH$^+$]. HPLC: $t_R$=1.99 min (ZQ3, polar_5 min).

4-[4-(4,4,5,5-Tetramethyl-1,3,2-dioxaborolan-2-yl)pyrazol-1-yl]-piperidine-1-carboxylic acid tert-butyl ester A mixture of 4-(4,4,5,5-tetramethyl[1,3,2]dioxaborolan-2-yl)-1H-pyrazole (30.0 g, 154 mmol), 4-methanesulfonyloxypiperidine-1-carboxylic acid tert-butyl ester (52.5 g, 200 mmol) and cesium carbonate (80.1 g, 246 mmol) in anhydrous DMF (400 mL) was heated to 100° C. for 24 h. DMF was removed under high vacuum. The residue was then diluted with water (200 mL) and extracted with EtOAc (3×200 mL). The combined organic phases were washed with water (3×50 mL) and brine (100 mL), dried over anhydrous sodium sulfate, filtered and concentrated under reduced pressure. To the orange-brown oily residue was added diisopropyl ether (300 mL), and the mixture was stirred at 0° C. for 2 h. Colorless crystals separated out that were filtered off and dried in vacuo to give a 1$^{st}$ crop of the title compound. The filtrate was then concentrated in vacuo, the residue was mixed with diisopropyl ether (100 mL), a small amount of the 1$^{s1}$ crop was added as a seed, and the mixture was stirred overnight. The resulting white precipitate was filtered and dried in vacuo as 2$^{nd}$ crop of the title compound. $^1$H NMR (300 MHz, CDCl$_3$): δ=1.33 (s, 12H), 1.48 (s, 9H), 1.85-1.93 (m, 2H), 2.15-2.18 (m, 2H), 2.83-2.92 (m, 2H), 4.23-4.39 (m, 3H), 7.76 (s, 1H), 7.84 (s, 1H).

4-Methanesulfonyloxypiperidine-1-carboxylic acid tert-butylester

To a solution of 1-Boc-4-hydroxypiperidine (32.2 g, 0.160 mol) in DCM (400 mL) were added triethylamine (26.8 mL, 0.192 mol), methanesulfonyl chloride (13.6 mL, 0.176 mol) and 4-dimethylaminopyridine (0.20 g, 0.0016 mol) at 0° C. under nitrogen atmosphere. The resulting mixture was slowly warmed to rt and stirred at rt overnight. The mixture was washed with sat. aq. NaHCO$_3$ (3×80 mL), brine (2×80 mL), and dried over anhydrous sodium sulfate. The filtrate was concentrated to give the title compound as a white solid. It was used in the next step without further purification. $^1$H NMR (400 MHz, CDCl$_3$): δ=1.47 (s, 9H), 1.80-1.85 (m, 2H), 1.95-1.99 (m, 2H), 3.05 (s, 3H), 3.28-3.34 (m, 2H), 3.68-3.74 (m, 2H), 4.89 (m$_e$, 1H).

Example 2

3-[1-(2,6-Dichloro-3-fluorophenyl)ethyl]-5-(1-piperidin-4-yl-1H-pyrazol-4-yl)-1H-pyrrolo[2,3-b]pyridine Prepared from 5-bromo-3-[1-(2,6-dichloro-3-fluorophenyl)ethyl]-1H-pyrrolo[2,3-b]-pyridine according to typical Suzuki coupling procedure described for synthesis of 3-[1-(2,6-Dichlorophenyl)ethyl]-5-(1-piperidin-4-yl-1H-pyrazol-4-yl)-1H-pyrrolo[2,3-b]pyridine in example 1. MS (ES$^+$): m/z 458.01, 460.03 [MH$^+$]. HPLC: $t_R$=2.34 min (ZQ3, polar_5 min).

Examples 3-31 were synthesized according to the method described for Example 2.

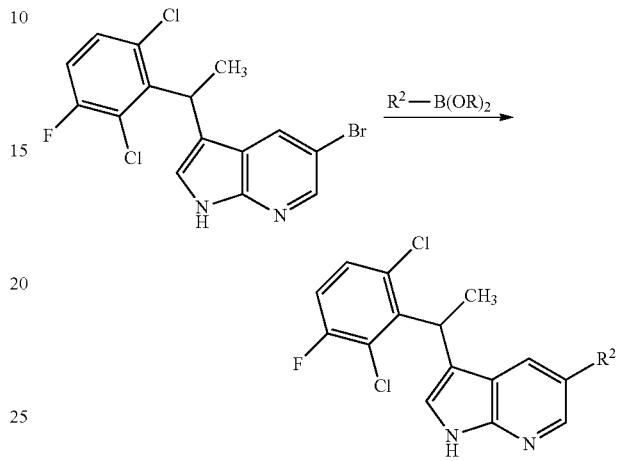

Example 3

4-{3-[1-(2,6-Dichloro-3-fluorophenyl)ethyl]-1H-pyrrolo[2,3-b]pyridin-5-yl}-N,N-dimethylbenzamide $^1$H NMR (400 MHz, CD$_3$OD): δ=8.41 (d, J=2.3 Hz, 1H), 7.47-7.54 (m, 5H), 7.34-7.47 (m, 2H), 7.18 (t, J=8.6 Hz, 1H), 5.33 (q, J=7.2 Hz, 1H), 3.12 (s, 3H), 3.05 (s, 3H), 1.90 (d, J=7.1 Hz, 3H). MS (ES+): m/z=456.32, 458.31 (100, 73) [MH$^+$]. HPLC: $t_R$=1.10 min (HPLC-ACQUITY, Purity).

Example 4

(4-{3-[1-(2,6-Dichloro-3-fluorophenyl)ethyl]-1H-pyrrolo[2,3-b]pyridin-5-yl}phenyl)pyrrolidin-1-yl-methanone MS (ES+): m/z=482.32, 484.34 (100, 67) [MH$^+$]. HPLC: $t_R$=1.15 min (HPLC-ACQUITY, Purity).

Example 5

4-{3-[1-(2,6-Dichloro-3-fluorophenyl)ethyl]-1H-pyrrolo[2,3-b]pyridin-5-yl}-N-methylbenzamide MS (ES+): m/z=442.32, 444.30 (100, 79) [MH$^+$]. HPLC: $t_R$=1.04 min (HPLC-ACQUITY, Purity).

Example 6

4-{3-[1-(2,6-Dichloro-3-fluorophenyl)ethyl]-1H-pyrrolo[2,3-b]pyridin-5-yl}-N-(2-methoxyethyl)benzamide MS (ES+): m/z=486.32, 488.30 (100, 78) [MH$^+$]. HPLC: $t_R$=1.07 min (HPLC-ACQUITY, Purity).

Example 7

4-{3-[1-(2,6-Dichloro-3-fluorophenyl)ethyl]-1H-pyrrolo[2,3-b]pyridin-5-yl}-N-(2-morpholin-4-yl-ethyl)benzamide MS (ES+): m/z=541.37, 543.36 (100, 70) [MH$^+$]. HPLC: $t_R$=0.77 min (HPLC-ACQUITY, Purity).

Example 8

4-{3-[1-(2,6-Dichloro-3-fluorophenyl)ethyl]-1H-pyrrolo[2,3-b]pyridin-5-yl}phenol MS (ES+): m/z=401.27, 403.28 (100, 72) [MH$^+$]. HPLC: $t_R$=1.06 min (HPLC-ACQUITY, Purity).

Example 9

3-[1-(2,6-Dichloro-3-fluorophenyl)ethyl]-5-thiophen-3-yl-1H-pyrrolo[2,3-b]pyridine MS (ES+): m/z=391.23, 393.24 (100, 78) [MH$^+$]. HPLC: $t_R$=1.28 min (HPLC-ACQUITY, Purity).

Example 10

N-(4-{3-[1-(2,6-Dichloro-3-fluorophenyl)ethyl]-1H-pyrrolo[2,3-b]pyridin-5-yl}phenyl)acetamide MS (ES+): m/z=442.28, 444.30 (100, 67) [MH$^+$]. HPLC: $t_R$=1.04 min (HPLC-ACQUITY, Purity).

Example 11

(4-{3-[1-(2,6-Dichloro-3-fluorophenyl)ethyl]-1H-pyrrolo[2,3-b]pyridin-5-yl}phenyl)dimethylamine MS (ES+): m/z=428.31, 430.29 (100, 73) [MH$^+$]. HPLC: $t_R$=1.22 min (HPLC-ACQUITY, Purity).

Example 12

3-[1-(2,6-Dichloro-3-fluorophenyl)ethyl]-5-pyrimidin-5-yl-1H-pyrrolo[2,3-b]pyridine MS (ES+): m/z=387.27, 389.28 (100, 73) [MH$^+$]. HPLC: $t_R$=1.03 min (HPLC-ACQUITY, Purity).

Example 13

(4-{3-[1-(2,6-Dichloro-3-fluorophenyl)ethyl]-1H-pyrrolo[2,3-b]pyridin-5-yl}phenyl)morpholin-4-ylmethanone MS (ES+): m/z=498.34, 500.33 (100, 68) [MH$^+$]. HPLC: $t_R$=1.08 min (HPLC-ACQUITY, Purity).

Example 14

4-{3-[1-(2,6-Dichloro-3-fluorophenyl)ethyl]-1H-pyrrolo[2,3-b]pyridin-5-yl}benzamide MS (ES+): m/z=428.28, 430.26 (100, 64) [MH$^+$]. HPLC: $t_R$=0.98 min (HPLC-ACQUITY, Purity).

Example 15

(4-{3-[1-(2,6-Dichloro-3-fluorophenyl)ethyl]-1H-pyrrolo[2,3-b]pyridin-5-yl}phenyl)-(4-methylpiperazin-1-yl)methanone MS (ES+): m/z=511.34, 513.37 (100, 80) [MH$^+$]. HPLC: $t_R$=0.74 min (HPLC-ACQUITY, Purity).

Example 16

3-[1-(2,6-Dichloro-3-fluorophenyl)ethyl]-5-[4-(4-methylpiperazin-1-yl)phenyl]-1H-pyrrolo[2,3-b]pyridine MS (ES+): m/z=483.26, 485.36 (100, 60) [MH$^+$]. HPLC: $t_R$=0.78 min (HPLC-ACQUITY, Purity).

Example 17

N-(4-{3-[1-(2,6-Dichloro-3-fluorophenyl)ethyl]-1H-pyrrolo[2,3-b]pyridin-5-yl}phenyl)methanesulfonamide MS (ES+): m/z=478.29, 480.24 (100, 84) [MH$^+$]. HPLC: $t_R$=1.07 min (HPLC-ACQUITY, Purity).

Example 18

4-{3-[1-(2,6-Dichloro-3-fluorophenyl)ethyl]-1H-pyrrolo[2,3-b]pyridin-5-yl}phenylamine MS (ES+): m/z=400.29, 402.28 (100, 72) [MH$^+$]. HPLC: $t_R$=0.97 min (HPLC-ACQUITY, Purity).

Example 19

3-[1-(2,6-Dichloro-3-fluorophenyl)ethyl]-5-phenyl-1H-pyrrolo[2,3-b]-pyridine

MS (ES+): m/z=385.28, 387.26 (100, 81) [MH$^+$]. HPLC: $t_R$=1.30 min (HPLC-ACQUITY, Purity).

Example 20

4-{3-[1-(2,6-Dichloro-3-fluorophenyl)ethyl]-1H-pyrrolo[2,3-b]pyridin-5-yl}-N-(2-dimethylaminoethyl)benzamide MS (ES+): m/z=499.35, 501.37 (100, 72) [MH$^+$]. HPLC: $t_R$=0.75 min (HPLC-ACQUITY, Purity).

Example 21

N-Cyclohexyl-4-{3-[1-(2,6-dichloro-3-fluorophenyl)ethyl]-1H-pyrrolo[2,3-b]pyridin-5-yl}benzamide MS (ES+): m/z=510.37, 512.35 (100, 71) [MH$^+$]. HPLC: $t_R$=1.28 min (HPLC-ACQUITY, Purity).

Example 22

4-{3-[1-(2,6-Dichloro-3-fluorophenyl)ethyl]-1H-pyrrolo[2,3-b]pyridin-5-yl}-N,N-dimethylbenzenesulfonamide MS (ES+): m/z=492.20, 494.18 (100, 73) [MH$^+$]. HPLC: $t_R$=1.21 min (HPLC-ACQUITY, Purity).

Example 23

4-{3-[1-(2,6-Dichloro-3-fluorophenyl)ethyl]-1H-pyrrolo[2,3-b]pyridin-5-yl}-N-methylbenzenesulfonamide MS (ES+): m/z=478.16, 480.18 (100, 74) [MH$^+$]. HPLC: $t_R$=1.11 min (HPLC-ACQUITY, Purity).

Example 24

4-{3-[1-(2,6-Dichloro-3-fluorophenyl)ethyl]-1H-pyrrolo[2,3-b]pyridin-5-yl}-N-(2-hydroxyethyl)benzamide MS (ES+): m/z=472.22, 474.20 (100, 72) [MH$^+$]. HPLC: $t_R$=0.96 min (HPLC-ACQUITY, Purity).

Example 25

3-[1-(2,6-Dichloro-3-fluorophenyl)ethyl]-5-(4-morpholin-4-ylphenyl)-1H-pyrrolo[2,3-b]pyridine MS (ES+): m/z=470.27, 472.25 (100, 76) [MH$^+$]. HPLC: $t_R$=1.22 min (HPLC-ACQUITY, Purity).

Example 26

3-[1-(2,6-Dichloro-3-fluorophenyl)-ethyl]-5-(1H-pyrazol-4-yl)-1H-pyrrolo[2,3-b]pyridine $^1$H NMR (400 MHz, CD$_3$OD): δ=1.89 (d, J=7.1 Hz, 3 H), 5.30 (q, J=7.3 Hz, 1 H), 7.15-7.22 (m, 1 H), 7.30-7.53 (m, 3 H), 7.72 (dd, J=5.8, 3.3 Hz, 2 H), 8.34 (d, J=2.0 Hz, 1H). MS (ES+): m/z 375.00 (100) [MH$^+$]. HPLC: $t_R$=3.29 min (ZQ3, polar_5 min).

Example 27

3-[1-(2,6-Dichloro-3-fluorophenyl)-ethyl]-5-(1-methyl-1H-pyrazol-4-yl)-1H-pyrrolo[2,3-b]pyridine $^1$H NMR (400 MHz, CD$_3$OD): δ=1.89 (d, J=7.1 Hz, 3 H), 3.92 (s, 3 H), 5.29 (q, J=7.1 Hz, 1 H), 7.20 (t, J=8.7 Hz, 1 H), 7.29-7.50 (m, 3 H), 7.56 (s, 1 H), 7.77 (s, 1 H), 8.32 (s, 1 H). MS (ES+): m/z 388.98 (100) [MH$^+$]. HPLC: $t_R$=3.52 min (ZQ3, polar_5 min).

Example 28

4-(4-{3-[1-(2,6-Dichloro-3-fluorophenyl)ethyl]-1H-pyrrolo[2,3-b]pyridin-5-yl}-pyrazol-1-yl)-piperidine-1-carboxylic acid dimethylamide $^1$H NMR (400 MHz, CD$_3$OD): δ=1.88 (d, J=7.1 Hz, 3 H), 1.97-2.16 (m, 4 H), 2.88 (s, 6 H), 2.92-3.02 (m, 2 H), 3.80 (d, J=13.4 Hz, 2 H), 4.30-4.42 (m, 1 H), 5.28 (q, J=7.3 Hz, 1H), 7.14-7.22 (m, 1H), 7.35 (d, J=1.3 Hz, 1 H), 7.40 (d, J=2.0 Hz, 1 H), 7.43 (br. s., 1 H), 7.57 (s, 1 H), 7.89 (s, 1 H), 8.31 (d, J=1.8 Hz, 1 H). MS (ES+): m/z 529.05 (100) [MH$^+$]. HPLC: $t_R$=3.51 min (ZQ3, polar_5 min).

4-[4-(4,4,5,5-Tetramethyl-[1,3,2]dioxaborolan-2-yl)-pyrazol-1-yl]-piperidine-1-carboxylic acid dimethylamide To a solution of 4-[4-(4,4,5,5-tetramethyl[1,3,2]dioxaborolan-2-yl)-pyrazol-1-yl]-piperidine hydrochloride (253.6 mg, 0.809 mmol) in DMF (6 mL), DIPEA (0.7 mL, 4 mmol) was added at rt. The solution was cooled to 0° C. and N,N-dimethylcarbamoyl chloride (107.7 mg, 1.002 mmol) in DMF (1 mL) was added. The reaction was stirred from 0° C.→rt for 30 min. MeOH was added and all organic solvent was concentrated in vacuo to dryness. The residue was dissolved in CH$_2$Cl$_2$, washed once with water and brine, dried over anhydrous Na$_2$SO$_4$, filtered, and concentrated in vacuo, giving the title compound as a waxy white solid that solidified upon drying. The material was used without further purification. $^1$H NMR (400 MHz, CDCl$_3$): δ=1.32 (s, 12H), 1.94-2.07 (m, 2H), 2.16 (dd, J=12.3, 2.4 Hz, 2H), 2.85 (s, 6H), 2.87-2.95 (m, 2H), 3.78 (d, J=13.4 Hz, 2H), 4.24-4.34 (m, 1H), 7.76 (s, 1H), 7.80 (s, 1H). MS (AP$^+$): m/z 349.13 (100) [MH$^+$]. HPLC: $t_R$=2.91 min (ZQ3, polar_5 min).

Example 29

3-[1-(2,6-Dichloro-3-fluorophenyl)ethyl]-5-{1-[1-(2,2,2-trifluoroethyl)-piperidin-4-yl]-1H-pyrazol-4-yl}-1H-pyrrolo[2,3-b]pyridine $^1$H NMR (400 MHz, CD$_3$OD): δ=1.88 (d, J=7.1 Hz, 3 H), 2.01-2.19 (m, 4 H), 2.60 (td, J=11.5, 3.3 Hz, 2 H), 3.07-3.18 (m, 4 H), 4.13-4.24 (m, 1 H), 5.29 (q, J=7.1 Hz, 1 H), 7.19 (t, J=8.6 Hz, 1 H), 7.36 (d, J=1.3 Hz, 1 H), 7.39 (d, J=2.0 Hz, 1 H), 7.43 (br. s., 1 H), 7.56 (s, 1H), 7.88 (s, 1 H), 8.31 (d, J=1.8 Hz, 1 H). MS (ES+): m/z 540.02 (100) [MH$^+$]. HPLC: $t_R$=4.01 min (ZQ3, polar_5 min).

4-[4-(4, 4,5,5-Tetramethyl-1,3,2-dioxaborolan-2-yl)-pyrazol-1-yl]-1-(2,2,2-trifluoroethyl)-piperidine The procedure for the preparation of 4-[4-(4,4,5,5-Tetramethyl-[1,3,2]dioxaborolan-2-yl)-pyrazol-1-yl]-piperidine-1-carboxylic acid dimethylamide was followed, except that 2,2,2-trifluoroethyl triflate (1.6 eq) was used in place of N,N-dimethylcarbamoyl chloride. After reacting for 3 h, EtOAc was added and a standard aqueous workup was performed. The crude was purified using a short silica gel plug [eluting with 2:1 CH$_2$Cl$_2$:EtOAc]. $^1$H NMR (400 MHz, CDCl$_3$): δ=1.33 (s, 12H), 1.58 (s, 2H), 2.00-2.11 (m, 2H), 2.11-2.19 (m, 2H), 2.59 (td, J=11.7, 2.2 Hz, 2H), 3.06-3.12 (m, 2H), 4.15 (tt, J=11.3, 4.3 Hz, 1H), 7.75 (s, 1H), 7.80 (s, 1H). MS (AP$^+$): m/z 360.14 (100) [MH$^+$]. HPLC: $t_R$=3.54 min (ZQ3, polar_5 min).

Example 30

3-[1-(2,6-Dichloro-3-fluorophenyl)ethyl]-5-(1-isopropyl-1H-pyrazol-4-yl)-1H-pyrrolo[2,3-b]pyridine $^1$H NMR (400 MHz, CD$_3$OD): δ=1.51 (d, J=6.8 Hz, 6 H), 1.88 (d, J=7.1 Hz, 3 H), 4.54 (dt, J=13.5, 6.8 Hz, 1 H), 5.29 (q, J=7.3 Hz, 1 H), 7.15-7.22 (m, 1 H), 7.35 (d, J=1.3 Hz, 1 H), 7.37-7.50 (m, 2 H), 7.55 (s, 1 H), 7.85 (s, 1 H), 8.31 (d, J=2.0

Hz, 1 H). MS (ES+): m/z 417.02 (100) [MH$^+$]. HPLC: $t_R$=3.82 min (ZQ3, polar_5 min).

1-Isopropyl-4-(4,4,5,5-tetramethyl[1,3,2]dioxaborolan-2-yl)-1H-pyrazole

In a sealed tube, to a suspension of 4-(4,4,5,5-tetramethyl [1,3,2]dioxaborolan-2-yl)-1H-pyrazole (566.9 mg, 2.922 mmol) and $Cs_2CO_3$ (1.5442 g, 4.739 mmol) in DMF (6 mL), isopropyl iodide (753.3 mg, 4.431 mmol) was added and the reaction was allowed to stir at 100° C. for 19 h. Water was added to dilute the reaction and dissolve all salts that had formed, after which EtOAc was added and the two layers were separated. The organic layer was washed twice with water and once with brine, dried over anhydrous $Na_2SO_4$, filtered, and concentrated in vacuo. The combined aqueous layers were back extracted once with EtOAc, which was combined with the other organic batch. One obtained the title material as yellow oil. It was used without further purification in the next step. $^1$H NMR (400 MHz, CDCl$_3$): δ=1.33 (s, 12H), 1.51 (d, J=6.8 Hz, 6H), 4.53 (spt, J=6.7 Hz, 1H), 7.75 (s, 1H), 7.80 (s, 1H). MS (AP$^+$): m/z 235.98 (76) [MH$^+$]. HPLC: $t_R$=3.22 min (ZQ3, polar_5 min).

Example 31

3-[1-(2,6-Dichloro-3-fluorophenyl)ethyl]-5-[1-(2-morpholin-4-ylethyl)-1H-pyrazol-4-yl]-1H-pyrrolo[2,3-b]pyridine $^1$H NMR (400 MHz, CD$_3$OD): δ=1.88 (d, J=7.1 Hz, 3 H), 2.58-2.70 (m, 4 H), 2.96 (t, J=6.3 Hz, 2 H), 3.65-3.76 (m, 4 H), 4.35 (t, J=6.3 Hz, 2 H), 5.28 (q, J=7.1 Hz, 1 H), 7.14-7.21 (m, 1 H), 7.37 (d, J=1.5 Hz, 1 H), 7.38-7.55 (m, 2 H), 7.60 (s, 1 H), 7.86 (s, 1 H), 8.31 (d, J=2.0 Hz, 1 H). MS (ES+): m/z 488.03 (100) [MH$^+$]. HPLC: $t_R$=2.60 min (ZQ3, polar_5 min).

Example 32

3-[1-(2,6-Dichloro-3-fluorophenyl)-ethyl]-5-(1,2,3,6-tetrahydropyridin-4-yl)-1H-pyrrolo[2,3-b]pyridine A mixture of 5-bromo-3-[1-(2,6-dichloro-3-fluorophenyl) ethyl]-1H-pyrrolo[2,3-b]pyridine (60.0 mg, 0.155 mmol), 4-(4,4,5,5-tetramethyl-[1,3,2]dioxaborolan-2-yl)-3,6-dihydro-2H-pyridine-1-carboxylic acid tert-butyl ester (95.6 mg, 0.309 mmol), Pd(PPh$_3$)$_4$ (40 mg, 0.03 mmol), potassium carbonate (64.1 mg, 0.464 mmol) and 4:1 dioxane/H$_2$O (10 mL) was heated to 90° C. for 2 h. The solution was loaded into an SCX cartridge, washed with MeOH (30 mL) and ejected with 2M NH$_3$ in MeOH (10 mL). The filtrate was concentrated in vacuo, redissolved in dioxane, and 4M HCl in dioxane (1 mL) was added. The solution was heated to 40° C. for 2 h. The material was loaded into an SCX cartridge, washed with MeOH (30 mL) and ejected with 2M NH$_3$ in MeOH (10 mL). The filtrate was concentrated in vacuo, redissolved in MeOH (0.5 mL) and purified via HPLC. The fractions containing the pure product were concentrated in vacuo to afford the title compound as a white solid. $^1$H NMR (400 MHz, CD$_3$OD): δ=1.88 (d, J=7.3 Hz, 3 H), 2.65-2.73 (m, 2 H), 3.45 (t, J=6.1 Hz, 2 H), 3.76-3.86 (m, 2 H), 5.28 (d, J=7.3 Hz, 1 H), 5.95 (dt, J=3.3, 1.7 Hz, 1 H), 7.19 (t, J=8.6 Hz, 1 H), 7.34 (d, J=2.3 Hz, 1 H), 7.36-7.50 (m, 2 H), 8.26 (d, J=2.0 Hz, 1 H). MS (ES+): m/z 390.00 (100) [MH$^+$]. HPLC: $t_R$=2.48 min (ZQ3, polar_5 min).

Example 33

4-{3-[1-(2,6-Dichloro-3-fluorophenyl)ethyl]-1H-pyrrolo[2,3-b]pyridin-5-yl}-3,6-dihydro-2H-pyridine-1-carboxamide A mixture of 3-[1-(2,6-dichloro-3-fluorophenyl)-ethyl]-5-(1,2,3,6-tetrahydropyridin-4-yl)-1H-pyrrolo[2,3-b]pyridine (12.0 mg, 0.0307 mmol), trimethylsilyl isocyanate (8.32 μL, 0.0615 mmol), DIPEA (26.8 μL, 0.154 mmol) and DMF (0.5 mL) was stirred at rt for 20 min. The solution was concentrated in vacuo, redissolved in MeOH (0.5 mL) and purified via HPLC. The fractions containing the pure product were concentrated in vacuo to afford the title compound as a white solid. $^1$H NMR (400 MHz, CD$_3$OD): δ=1.87 (d, J=7.1 Hz, 3 H), 2.28-2.51 (m, 2 H), 3.60 (t, J=5.8 Hz, 2 H), 4.02 (q, J=2.5 Hz, 2 H), 5.26 (q, J=7.1 Hz, 1 H), 5.88-5.94 (m, 1 H), 7.18 (t, J=8.6 Hz, 1 H), 7.29 (d, J=2.0 Hz, 1 H), 7.32-7.55 (m, 2 H), 8.23 (br. s., 1 H). MS (ES+): m/z 433.02 (100) [MH$^+$]. HPLC: $t_R$=3.15 min (ZQ3, polar_5 min).

Examples 34-37 were synthesized according to the procedure described for synthesis of Example 33

Example 34

4-{3-[1-(2,6-Dichloro-3-fluorophenyl)ethyl]-1H-pyrrolo[2,3-b]pyridin-5-yl}-3,6-dihydro-2H-pyridine-1-carboxylic acid methylamide $^1$H NMR (400 MHz, CD$_3$OD): δ=1.87 (d, J=7.1 Hz, 3 H), 2.30-2.49 (m, 2 H), 2.76 (s, 3 H), 3.59 (t, J=5.8 Hz, 2 H), 3.98 (q, J=2.5 Hz, 2 H), 5.25 (q, J=7.1 Hz, 1 H), 5.88-5.94 (m, 1 H), 7.19 (t, J=8.6 Hz, 1 H), 7.27 (d, J=2.0 Hz, 1 H), 7.38 (d, J=1.5 Hz, 2 H), 8.22 (br. s., 1 H). MS (ES+): m/z 447.03 (100) [MH$^+$]. HPLC: $t_R$=3.34 min (ZQ3, polar_5 min).

Example 35

4-{3-[1-(2,6-Dichloro-3-fluorophenyl)-ethyl]-1H-pyrrolo[2,3-b]pyridin-5-yl}-3,6-dihydro-2H-pyridine-1-carboxylic acid methyl ester $^1$H NMR (400 MHz, CD$_3$OD): δ=1.87 (d, J=7.3 Hz, 3 H), 2.28-2.49 (m, 2 H), 3.65 (t, J=5.7 Hz, 2 H), 3.72 (s, 3 H), 4.07 (br. s., 2 H), 5.26 (q, J=7.0 Hz, 1 H), 5.89 (br. s., 1 H), 7.15-7.22 (m, 1 H), 7.27 (d, J=2.0 Hz, 1 H), 7.36 (d, J=1.3 Hz, 1 H), 7.41 (br. s., 1 H), 8.21 (d, J=2.0 Hz, 1 H). MS (ES+): m/z 448.00 (100) [MH$^+$]. HPLC: $t_R$=3.86 min (ZQ3, polar_5 min).

Example 36

4-{3-[1-(2,6-Dichloro-3-fluorophenyl)-ethyl]-1H-pyrrolo[2,3-b]pyridin-5-yl}-3,6-dihydro-2H-pyridine-1-carboxylic acid dimethylamide $^1$H NMR (400 MHz, CD$_3$OD): δ=1.87 (d, J=7.1 Hz, 3 H), 2.34-2.54 (m, 2 H), 2.87 (s, 6 H), 3.45 (t, J=5.7 Hz, 2 H), 3.90 (q, J=2.6 Hz, 2 H), 5.26 (q, J=7.3 Hz, 1 H), 5.91 (dt, J=3.3, 1.7 Hz, 1 H), 7.19 (t, J=8.7 Hz, 1 H), 7.29 (d, J=2.3 Hz, 1 H), 7.36 (d, J=1.3 Hz, 1 H), 7.43 (br. s., 1 H), 8.22 (s, 1 H). MS (ES+): m/z 461.04 (100) [MH$^+$]. HPLC: $t_R$=3.66 min (ZQ3, polar_5 min).

Example 37

3-[1-(2,6-Dichloro-3-fluorophenyl)ethyl]-5-[1-(1-methanesulfonylpiperidin-4-yl)-1H-pyrazol-4-yl]-1H-pyrrolo[2,3-b]pyridine $^1$H NMR (400 MHz, CD$_3$OD): δ=1.87 (d, J=7.3 Hz, 3 H), 2.45-2.61 (m, 2 H), 2.89 (s, 3 H), 3.47 (t, J=5.8 Hz, 2 H), 3.91 (q, J=2.6 Hz, 2 H), 5.26 (q, J=7.3 Hz, 1 H), 5.94 (dt, J=3.3, 1.7 Hz, 1 H), 7.10-7.18 (m, 1H), 7.31 (d, J=2.0 Hz, 1 H), 7.35 (d, J=1.3 Hz, 1 H), 7.41 (br. s., 1 H), 8.18-8.24 (m, 1 H). MS (ES+): m/z 467.98 (100) [MH$^+$]. HPLC: t$_R$=3.63 min (ZQ3, polar__5 min).

Example 38

4-{3-[1-(2,6-Dichloro-3-fluorophenyl)ethyl]-1H-pyrrolo[2,3-b]pyridin-5-yl}-3,6-dihydro-2H-pyridine-1-carbaldehyde A mixture of 3-[1-(2,6-dichloro-3-fluorophenyl)ethyl]-5-(1,2,3,6-tetrahydropyridin-4-yl)-1H-pyrrolo[2,3-b]pyridine (12.0 mg, 0.0307 mmol), formic acid (2.3 μL, 0.0615 mmol), TBTU (19.7 mg, 0.0615 mmol), DIPEA (26.8 μL, 0.154 mmol) and DCM (1 mL) was stirred at rt for 30 min. The solution was concentrated in vacuo, redissolved in MeOH (0.5 mL) and purified via HPLC. The fractions containing the pure product were concentrated in vacuo to afford the title compound as a white solid. $^1$H NMR (400 MHz, CD$_3$OD): δ=1.87 (d, J=7.3 Hz, 3 H), 2.36-2.58 (m, 2H), 3.63-3.80 (m, 2 H), 4.05-4.15 (m, 2 H), 5.26 (q, J=7.2 Hz, 1 H), 5.86-5.97 (m, 1 H), 7.18 (t, J=8.7 Hz, 1 H), 7.24-7.31 (m, 1 H), 7.32-7.54 (m, 2 H), 8.09-8.17 (m, 1 H), 8.22 (d, J=2.0 Hz, 1 H). MS (ES+): m/z 418.04 (100) [MH$^+$]. HPLC: t$_R$=3.40 min (ZQ3, polar__5 min).

Examples 39-44 were synthesized according to the procedure described for synthesis of Example 38.

Example 39

1-(4-{3-[1-(2,6-Dichloro-3-fluorophenyl)ethyl]-1H-pyrrolo[2,3-b]pyridin-5-yl}-3,6-dihydro-2H-pyridin-1-yl)-ethanone $^1$H NMR (400 MHz, CD$_3$OD): δ=1.87 (d, J=7.3 Hz, 3 H), 2.14 (d, J=14.7 Hz, 3 H), 2.30-2.44 (m, 1 H), 2.44-2.58 (m, 1 H), 3.68-3.79 (m, 2 H), 4.10-4.21 (m, 2 H), 5.26 (q, J=7.0 Hz, 1 H), 5.86-5.96 (m, 1 H), 7.18 (t, J=8.6 Hz, 1 H), 7.29 (dd, J=6.3, 2.3 Hz, 1 H), 7.37 (d, J=1.5 Hz, 1 H), 7.42 (br. s., 1 H), 8.22 (dd, J=4.5, 2.0 Hz, 1 H). MS (ES+): m/z 432.04 (100) [MH$^+$]. HPLC: t$_R$=3.44 min (ZQ3, polar__5 min).

Example 40

(R)-1-(4-{3-[1-(2,6-Dichloro-3-fluorophenyl)ethyl]-1H-pyrrolo[2,3-b]-pyridin-5-yl}-3,6-dihydro-2H-pyridin-1-yl)-2-hydroxypropan-1-one $^1$H NMR (400 MHz, CD$_3$OD): δ=1.34 (dd, J=16.2, 6.6 Hz, 3 H), 1.87 (d, J=7.1 Hz, 3H), 2.33-2.58 (m, 2 H), 3.66-3.82 (m, 2 H), 4.12-4.23 (m, 2 H), 4.54-4.70 (m, 1 H), 5.27 (q, J=7.2 Hz, 1 H), 5.93 (br. s., 1 H), 7.19 (t, J=8.6 Hz, 1 H), 7.26-7.31 (m, 1 H), 7.37 (d, J=1.5 Hz, 1 H), 7.41 (br. s., 1 H), 8.22 (d, J=2.0 Hz, 1 H). MS (ES+): m/z 462.02 (100) [MH$^+$]. HPLC: t$_R$=3.38 min (ZQ3, polar__5 min).

Example 41

(S)-1-(4-{3-[1-(2,6-Dichloro-3-fluorophenyl)ethyl]-1H-pyrrolo[2,3-b]-pyridin-5-yl}-3,6-dihydro-2H-pyridin-1-yl)-2-hydroxypropan-1-one $^1$H NMR (400 MHz, CD$_3$OD): δ=1.34 (dd, J=16.3, 6.7 Hz, 3 H), 1.87 (d, J=7.3 Hz, 3H), 2.51 (br. s., 2 H), 3.66-3.82 (m, 2 H), 4.13-4.33 (m, 2 H), 4.54-4.68 (m, 1 H), 5.22-5.31 (m, 1 H), 5.93 (br. s., 1 H), 7.19 (t, J=8.7 Hz, 1 H), 7.26-7.31 (m, 1 H), 7.38 (d, J=1.5 Hz, 1H), 7.42 (br. s., 1 H), 8.23 (br. s., 1 H). MS (ES+): m/z 462.04 (100) [MH$^+$]. HPLC: t$_R$=3.38 min (ZQ3, polar__5 min).

Example 42

1-(4-{3-[1-(2,6-Dichloro-3-fluorophenyl)ethyl]-1H-pyrrolo[2,3-b]pyridin-5-yl}-3,6-dihydro-2H-pyridin-1-yl)-2-hydroxy-2-methylpropan-1-one $^1$H NMR (400 MHz, CD$_3$OD): δ=1.44 (s, 6 H), 1.87 (d, J=7.3 Hz, 3 H), 2.47 (d, J=4.3 Hz, 2 H), 3.81 (br. s., 2 H), 4.06-4.26 (m, 2 H), 5.26 (q, J=7.2 Hz, 1 H), 5.93 (br. s., 1 H), 7.19 (t, J=8.6 Hz, 1 H), 7.28 (s, 1 H), 7.37 (d, J=1.5 Hz, 1 H), 7.43 (br. s., 1 H), 8.25 (br. s., 1 H). MS (ES+): m/z 476.03 (100) [MH$^+$]. HPLC: t$_R$=3.52 min (ZQ3, polar__5 min).

Example 43

1-(4-{3-[1-(2,6-Dichloro-3-fluorophenyl)ethyl]-1H-pyrrolo[2,3-b]pyridin-5-yl}-3,6-dihydro-2H-pyridin-1-yl)-2-hydroxyethanone $^1$H NMR (400 MHz, CD$_3$OD): δ=1.86 (d, J=7.3 Hz, 3 H), 2.33-2.57 (m, 2 H), 3.60 (t, J=5.7 Hz, 1 H), 3.74-3.83 (m, 1 H), 4.04 (d, J=2.8 Hz, 1 H), 4.17 (d, J=2.8 Hz, 1 H), 4.24 (s, 1 H), 4.30 (s, 1 H), 5.26 (q, J=7.1 Hz, 1 H), 5.86-5.94 (m, 1 H), 7.18 (t, J=8.6 Hz, 1 H), 7.28 (dd, J=3.5, 2.0 Hz, 1 H), 7.37 (d, J=1.5 Hz, 1 H), 7.43 (br. s., 1 H), 8.22 (br. s., 1 H). MS (ES+): m/z 448.00 (100) [MH$^+$]. HPLC: t$_R$=3.30 min (ZQ3, polar__5 min).

Example 44

1-[4-(4-{3-[1-(2,6-Dichloro-3-fluorophenyl)-ethyl]-1H-pyrrolo[2,3-b]pyridin-5-yl}-pyrazol-1-yl]-piperidin-1-yl)-ethanone $^1$H NMR (400 MHz, CD$_3$OD): δ=1.87 (d, J=7.3 Hz, 3 H), 2.51 (br. s., 2 H), 3.80-3.88 (m, 2 H), 4.26 (dd, J=3.4, 2.4 Hz, 2 H), 5.04-5.15 (m, 1 H), 5.22-5.31 (m, 1 H), 5.89-5.96 (m, 1 H), 7.19 (t, J=8.6 Hz, 1 H), 7.27-7.31 (m, 1 H), 7.35-7.54 (m, 2 H), 8.23 (br. s., 1 H). MS (ES+): m/z 515.98 (100) [MH$^+$]. HPLC: t$_R$=3.70 min (ZQ3, polar__5 min).

Example 45

2-Amino-1-(4-{3-[1-(2,6-dichloro-3-fluorophenyl)ethyl]-1H-pyrrolo[2,3-b]pyridin-5-yl}-3,6-dihydro-2H-pyridin-1-yl)-2-methylpropan-1-one A mixture of 3-[1-(2,6-dichloro-3-fluorophenyl)ethyl]-5-(1,2,3,6-tetrahydropyridin-4-yl)-1H-pyrrolo[2,3-b]pyridine (12.0 mg, 0.0307 mmol), 2-aminoisobutanoic acid BOC (10.4 mg, 0.0615 mmol), TBTU (19.7 mg, 0.0615 mmol), DIPEA (26.8 μL, 0.154 mmol) and DCM (1 mL) was stirred at rt overnight. The solution was transferred to a separatory funnel, and extracted with DCM and water. The organic layer was concentrated in vacuo, redissolved in dioxane, and 4M HCl in dioxane (1 mL) was added. The solution was heated to 50° C. for 2 h. The solution was concentrated in vacuo, redissolved in MeOH (0.5 mL) and purified via HPLC. The fractions containing the pure product were concentrated in vacuo to afford the title compound as a white solid. $^1$H NMR (400 MHz, CD$_3$OD): δ=1.69 (s, 6 H), 1.86 (d, J=7.1 Hz, 3 H), 2.40-2.60 (m, 2 H), 3.85 (t, J=5.7 Hz, 2 H), 4.25 (br. s., 2 H), 5.25 (q, J=7.2 Hz, 1 H), 5.93 (br. s., 1 H), 7.12 (t, J=8.5 Hz, 1 H), 7.24-7.47 (m, 3 H), 8.21 (br. s., 1 H). MS (ES+): m/z 475.06 (100) [MH$^+$]. HPLC: t$_R$=2.52 min (ZQ3, polar_5 min).

Example 46

4-{3-[1-(2,6-Dichloro-3-fluorophenyl)ethyl]-1H-pyrrolo[2,3-b]pyridin-5-yl}-3,6-dihydro-2H-pyridine-1-sulfonic acid amide A mixture of 3-[1-(2,6-dichloro-3-fluorophenyl)ethyl]-5-(1,2,3,6-tetrahydropyridin-4-yl)-1H-pyrrolo[2,3-b]pyridine (10.0 mg, 0.0256 mmol), sulfamide (4.92 mg, 0.0512 mmol) and dioxane (2 mL) was heated to 90° C. for 16 h in a sealed tube. The solution was concentrated in vacuo, redissolved in MeOH and purified via HPLC. The fractions containing the pure product were concentrated in vacuo to afford the title compound as a white solid. $^1$H NMR (400 MHz, CD$_3$OD): δ=1.87 (d, J=7.1 Hz, 3 H), 2.40-2.60 (m, 2 H), 3.32-3.35 (m, 2 H), 3.77 (q, J=2.6 Hz, 2 H), 5.26 (q, J=7.1 Hz, 1 H), 5.90-5.96 (m, 1 H), 7.19 (t, J=8.6 Hz, 1 H), 7.29 (s, 1 H), 7.37 (d, J=1.5 Hz, 1 H), 7.42 (br. s., 1 H), 8.28 (br. s., 1 H). MS (ES+): m/z 469.00 (100) [MH$^+$]. HPLC: t$_R$=3.42 min (ZQ3, polar_5 min).

Example 47

4-(4-{3-[1-(2,6-Dichloro-3-fluorophenyl)ethyl]-1H-pyrrolo[2,3-b]pyridin-5-yl}-pyrazol-1-yl)-piperidine-1-carbaldehyde A mixture of 3-[1-(2,6-dichloro-3-fluorophenyl)ethyl]-5-(1-piperidin-4-yl-1H-pyrazol-4-yl)-1H-pyrrolo[2,3-b]pyridine (8.0 mg, 0.0174 mmol), formic acid (1.3 µL, 0.0349 mmol), TBTU (11.2 mg, 0.0349 mmol), DIPEA (20 µL, 0.09 mmol) and DCM (1 mL) was stirred at rt for 30 min. The solution was concentrated in vacuo, redissolved in MeOH (0.5 mL) and purified via HPLC. The fractions containing the pure product were concentrated in vacuo to afford the title compound as a white solid. $^1$H NMR (400 MHz, CD$_3$OD): δ=1.88 (d, J=7.1 Hz, 3 H), 1.90-2.07 (m, 2 H), 2.10-2.23 (m, 2 H), 2.90 (td, J=12.9, 2.9 Hz, 1 H), 3.32-3.37 (m, 1 H), 3.89 (ddd, J=13.5, 2.2, 2.0 Hz, 1 H), 4.41-4.56 (m, 2 H), 5.28 (q, J=7.2 Hz, 1 H), 7.18 (t, J=8.6 Hz, 1 H), 7.30-7.53 (m, 3 H), 7.58 (s, 1 H), 7.90 (s, 1 H), 8.07 (s, 1 H), 8.31 (d, J=1.8 Hz, 1H). MS (ES+): m/z 486.00 (100) [MH$^+$]. HPLC: t$_R$=3.30 min (ZQ3, polar_5 min).

Example 48 was synthesized according to the procedure described for synthesis of Example 47.

Example 48

1-[4-(4-{3-[1-(2,6-Dichloro-3-fluorophenyl)ethyl]-1H-pyrrolo[2,3-b]pyridin-5-yl}-pyrazol-1-yl)-piperidin-1-yl)-ethanone $^1$H NMR (400 MHz, CD$_3$OD): δ=1.88 (d, J=7.3 Hz, 3 H), 1.90-2.08 (m, 2 H), 2.08-2.22 (m, 5 H), 2.83 (td, J=12.9, 2.4 Hz, 1 H), 3.31-3.36 (m, 1 H), 4.01-4.12 (m, 1 H), 4.46 (tt, J=11.4, 4.3 Hz, 1 H), 4.60-4.70 (m, 1 H), 5.28 (q, J=7.1 Hz, 1 H), 7.18 (t, J=8.6 Hz, 1 H), 7.30-7.49 (m, 3 H), 7.57 (s, 1 H), 7.90 (s, 1 H), 8.32 (br. s., 1 H). MS (ES+): m/z 500.02 (100) [MH$^+$]. HPLC: t$_R$=3.34 min (ZQ3, polar_5 min).

Example 49

4-(4-{3-[1-(2,6-Dichloro-3-fluorophenyl)ethyl]-1H-pyrrolo[2,3-b]pyridin-5-yl}-pyrazol-1-yl)-piperidine-1-carboxamide A mixture of 3-[1-(2,6-dichloro-3-fluorophenyl)ethyl]-5-(1-piperidin-4-yl-1H-pyrazol-4-yl)-1H-pyrrolo[2,3-b]pyridine (8.0 mg, 0.0174 mmol), trimethylsilyl isocyanate (4.02 mg, 0.0349 mmol), DIPEA (0.02 mL, 0.09 mmol) and DCM (1 mL) was stirred at rt for 30 min. The solution was concentrated in vacuo, redissolved in MeOH and purified via HPLC. The fractions containing the pure product were concentrated in vacuo to afford the title compound as a white solid. $^1$H NMR (400 MHz, CD$_3$OD): δ=1.89 (d, J=7.1 Hz, 3 H), 1.93-2.05 (m, 2H), 2.07-2.16 (m, 2 H), 2.95-3.06 (m, 2 H), 4.17 (d, J=13.6 Hz, 2 H), 4.41 (tt, J=11.5, 4.2 Hz, 1 H), 5.25-5.34 (m, 1 H), 7.19 (t, J=8.7 Hz, 1 H), 7.36 (d, J=1.5 Hz, 1 H), 7.38-7.52 (m, 2 H), 7.58 (s, 1 H), 7.90 (s, 1 H), 8.32 (d, J=1.8 Hz, 1 H). MS (ES+): m/z 501.02 (100) [MH$^+$]. HPLC: t$_R$=3.15 min (ZQ3, polar_5 min).

Example 50

3-[1-(2,6-Dichloro-3-fluorophenyl)-ethyl]-5-[1-(1-methanesulfonyl-piperidin-4-yl)-1H-pyrazol-4-yl]-1H-pyrrolo[2,3-b]pyridine Example 50 was synthesized according to the procedure described for synthesis of Example 49, substituting trimethylsilyl isocyanate with methanesulfonyl chloride. $^1$H NMR (400 MHz, CD$_3$OD): δ=1.88 (d, J=7.3 Hz, 3 H), 2.07-2.23 (m, 4 H), 2.91 (s, 3 H), 3.00 (td, J=12.1, 2.8 Hz, 2 H), 3.87 (d, J=12.1 Hz, 2 H), 4.32-4.41 (m, 1 H), 5.28 (q, J=7.2 Hz, 1 H), 7.20 (t, J=8.6 Hz, 1 H), 7.37 (d, J=1.5 Hz, 1 H), 7.39 (d, J=2.0 Hz, 1 H), 7.42 (br. s., 1 H), 7.58 (d, J=0.8 Hz, 1 H), 7.89-7.93 (m, 1 H), 8.32 (d, J=2.0 Hz, 1 H). MS (ES+): m/z 536.02 (100) [MH$^+$]. HPLC: t$_R$=3.48 min (ZQ3, polar_5 min).

Example 51

4-(4-{3-[1-(2,6-Dichloro-3-fluorophenyl)ethyl]-1H-pyrrolo[2,3-b]pyridin-5-yl}-pyrazol-1-yl)-piperidine-1-carboxylic acid methylamide Example 51 was synthesized according to the procedure described for synthesis of Example 49, substituting trimethylsilyl isocyanate with methyl isocyanate. $^1$H NMR (400 MHz, CD$_3$OD): δ=1.87 (d, J=7.1 Hz, 3 H), 1.89-1.99 (m, 2 H), 2.06-2.15 (m, 2 H), 2.74 (s, 3 H), 2.91-3.00 (m, 2 H), 4.13 (d, J=13.6 Hz, 2 H), 4.31-4.42 (m, 1 H), 5.27 (q, J=7.2 Hz, 1 H), 7.11-7.18 (m, 1 H), 7.34 (d, J=1.3 Hz, 1 H), 7.35-7.48 (m, 2 H), 7.56 (s, 1 H), 7.82 (s, 1 H), 8.29 (br. s., 1 H). MS (ES+): m/z 515.05 (100) [MH$^+$]. HPLC: t$_R$=3.23 min (ZQ3, polar_5 min).

Example 52

4-(4-{3-[1-(2,6-Dichloro-3-fluorophenyl)ethyl]-1H-pyrrolo[2,3-b]pyridin-5-yl}-pyrazol-1-yl)-piperidine-1-sulfonic acid amide A mixture of 3-[1-(2,6-dichloro-3-fluorophenyl)ethyl]-5-(1-piperidin-4-yl-1H-pyrazol-4-yl)-1H-pyrrolo[2,3-b]pyridine (8.0 mg, 0.0174 mmol), sulfamide (3.35 mg, 0.0349 mmol) and dioxane (2 mL) was heated to 90° C. overnight in a sealed tube. The solution was concentrated in vacuo, redissolved in MeOH and purified via HPLC. The fractions containing the pure product were concentrated in vacuo to afford the title compound as a white solid. $^1$H NMR (400 MHz, CD$_3$OD): δ=1.89 (d, J=7.1 Hz, 3 H), 2.09-2.25 (m, 4 H), 2.76-2.91 (m, 2H), 3.78 (d, J=12.4 Hz, 2 H), 4.30 (dt, J=10.4, 5.3 Hz, 1 H), 5.29 (q, J=7.4 Hz, 1 H), 7.15-7.23 (m, 1 H), 7.36 (d, J=1.5 Hz, 1 H), 7.38-7.53 (m, 2 H), 7.58 (s, 1 H), 7.92 (s, 1 H), 8.32 (d, J=1.8 Hz, 1 H). MS (ES+): m/z 537.02 (100) [MH$^+$]. HPLC: $t_R$=3.36 min (ZQ3, polar__5 min).

Example 53

5-(1-Azetidin-3-yl-1H-pyrazol-4-yl)-3-[1-(2,6-dichloro-3-fluoro-phenyl)ethyl]-1H-pyrrolo[2,3-b]pyridine

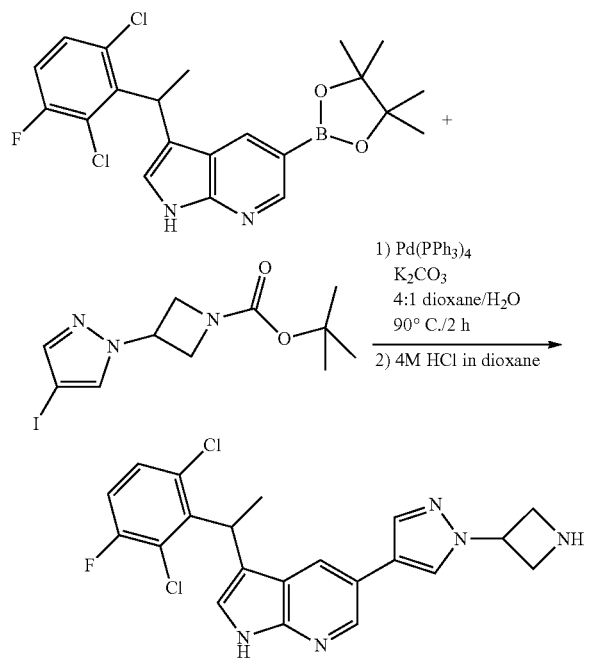

A mixture of 3-[1-(2,6-dichloro-3-fluorophenyl)ethyl]-5-(4,4,5,5-tetramethyl-[1,3,2]dioxaborolan-2-yl)-1H-pyrrolo[2,3-b]pyridine (100.0 mg, 0.230 mmol), 3-(4-iodopyrazol-1-yl)-azetidine-1-carboxylic acid tert-butyl ester (88.3 mg, 0.253 mmol), Pd(PPh$_3$)$_4$ (10 mg, 0.01 mmol), potassium carbonate (95.3 mg, 0.689 mmol) and 4:1 dioxane/H$_2$O (8 mL) was heated to 90° C. for 2 h. The organic solvent was removed in vacuo, and the material was transferred to a separatory funnel, extracting with DCM and water. The organic layer was concentrated in vacuo, redissolved in dioxane, and 4M HCl in dioxane (1 mL) was added. The solution was heated to 45° C. for 3 h. The solvents were removed on the corrosive pump, and the material was dry-loaded onto silica gel for column chromatography, eluting with 3-6% (7N NH$_3$ in MeOH)/DCM. The fractions containing the pure product were concentrated in vacuo to afford the title compound as a yellow solid. $^1$H NMR (400 MHz, CD$_3$OD): δ 1.88 (d, J=7.3 Hz, 3 H), 3.90-3.98 (m, 2 H), 4.08-4.15 (m, 2 H), 5.20-5.34 (m, 2 H), 7.18 (t, J=8.6 Hz, 1 H), 7.36 (d, J=1.3 Hz, 1 H), 7.36-7.48 (m, 2 H), 7.65 (s, 1 H), 7.95 (s, 1 H), 8.32 (d, J=2.0 Hz, 1 H). MS (ES+): m/z 430.10 (100) [MH$^+$]. HPLC: $t_R$=2.25 min (ZQ3, polar__5 min).

3-(4-Iodopyrazol-1-yl)-azetidine-1-carboxylic acid tert-butyl ester

A mixture of 3-methanesulfonyloxyazetidine-1-carboxylic acid tert-butyl ester (4.00 g, 15.9 mmol), 4-iodopyrazole (3.1 g, 15.9 mmol), potassium carbonate (2.85 g, 20.6 mmol) and 18-crown-6 (400 mg) in dry DMF (15 mL) was heated at 85° C. for 24 h. The reaction mixture was cooled to RT, poured into water and extracted with EtOAc (3×20 mL). The combined organic layers were washed with water (2×10 mL), dried over anhydrous sodium sulfate, filtered, and concentrated under reduced pressure. The residue was purified by column chromatography on silica gel eluting with hexanes/dichloromethane/ethyl acetate (8:1:1) to give the pure title compound. $^1$H NMR (300 MHz, CDCl$_3$): δ=1.47 (s, 9H), 4.29 (m, 2H), 4.36 (m, 2H), 5.05 (m, 1H), 7.59 (s, 1H), 7.60 (s, 1H).

Example 54

3-[1-(2,6-Dichloro-3-fluorophenyl)ethyl]-5-(1-methyl-1H-imidazol-4-yl)-1H-pyrrolo[2,3-b]pyridine To a stirred mixture of 3-[1-(2,6-dichloro-3-fluorophenyl)ethyl]-5-(4,4,5,5-tetramethyl[1,3,2]dioxaborolan-2-yl)-1H-pyrrolo[2,3-b]pyridine (10.0 mg, 0.0229 mmol), 4-iodo-1-methyl-1H-imidazole (7.17 mg, 0.0344 mmol), potassium carbonate (9.53 mg, 0.0689 mmol) in DME (2.0 mL) and H$_2$O (0.40 mL) was added (1,1'-bis-(diphenylphosphino)ferrocene) palladium dichloride (0.84 mg, 0.0011 mmol) under nitrogen atmosphere. The resulting mixture was refluxed at 100° C. for 90 min. The solvent was then removed under reduced pressure and the resulting residue was purified by a flash chromatography (eluent: 2% MeOH in DCM) to give desired product. $^1$H NMR (400 MHz, CD$_3$OD): δ=1.88 (d, J=7.1 Hz, 3 H), 3.75 (s, 3 H), 5.30 (q, J=6.8 Hz, 1 H), 7.12-7.18 (m, 1 H), 7.22 (d, J=1.5 Hz, 1 H), 7.33 (d, J=1.3 Hz, 1 H), 7.39 (br. s., 1 H), 7.62 (s, 1 H), 7.67 (d, J=2.0 Hz, 1 H), 8.48 (d, J=2.0 Hz, 1H). MS (ES+): m/z 389.05 [MH$^+$]. HPLC: $t_R$=2.54 min (ZQ3, polar__5 min).

Example 55

3-(4-{3-[1-(2,6-Dichloro-3-fluorophenyl)ethyl]-1H-pyrrolo[2,3-b]pyridin-5-yl}-pyrazol-1-yl)-azetidine-1-carbaldehyde A mixture of 5-(1-azetidin-3-yl-1H-pyrazol-4-yl)-3-[1-(2,6-dichloro-3-fluorophenyl)-ethyl]-1H-pyrrolo[2,3-b]pyridine (6.0 mg, 0.014 mmol) and ethyl formate (2 mL) was heated to 50° C. overnight in a sealed tube. The solution was concentrated in vacuo, redissolved in MeOH and purified via HPLC. The fractions containing the pure product were concentrated in vacuo to afford the title compound as a white solid. $^1$H NMR (400 MHz, CD$_3$OD): δ=1.89 (d, J=7.3 Hz, 3 H), 4.37 (ddd, J=6.2, 5.1, 4.9 Hz, 1 H), 4.46-4.54 (m, 1 H), 4.60 (dd, J=9.2, 5.4 Hz, 1 H), 4.71 (t, J=8.6 Hz, 1 H), 5.30 (q, J=7.3 Hz, 1 H), 5.38 (tt, J=8.2, 5.5 Hz, 1 H), 7.16-7.23 (m, 1 H), 7.38 (d, J=1.3 Hz, 1 H), 7.39-7.57 (m, 2 H), 7.72 (s, 1 H), 7.95 (s, 1 H), 8.07 (s, 1 H), 8.33 (d, J=1.8 Hz, 1 H). MS (ES+): m/z 458.06 (100) [MH$^+$]. HPLC: $t_R$=3.22 min (ZQ3, polar__5 min).

Example 56

3-(4-{3-[1-(2,6-Dichloro-3-fluorophenyl)ethyl]-1H-pyrrolo[2,3-b]pyridin-5-yl}-pyrazol-1-yl)-azetidine-1-carboxamide A mixture of 5-(1-azetidin-3-yl-1H-pyrazol-4-yl)-3-[1-(2,6-dichloro-3-fluorophenyl)ethyl]-1H-pyrrolo[2,3-b]pyridine (6.0 mg, 0.014 mmol), trimethylsilyl isocyanate (5.0 µL, 0.037 mmol), DIPEA (0.02 mL, 0.09 mmol) and DCM (2 mL) was stirred at rt for 30 min. The solution was concentrated in vacuo, redissolved in MeOH and purified via HPLC. The fractions containing the pure product were concentrated in vacuo to afford the title compound as a white solid. $^1$H NMR (400 MHz, CD$_3$OD): δ 1.89 (d, J=7.1 Hz, 3 H), 4.29-4.36 (m, 2 H), 4.42 (t, J=8.5 Hz, 2 H), 5.20-5.34 (m, 2 H), 7.14-7.23 (m, 1 H), 7.37 (d, J=1.3 Hz, 1 H), 7.39-7.52 (m, 2 H), 7.69 (s, 1 H), 7.94 (s, 1 H), 8.33 (s, 1 H). MS (ES+): m/z 473.11 (100) [MH$^+$]. HPLC: $t_R$=2.86 min (ZQ3, polar_5 min).

Example 57-58 were synthesized according to the procedure described for synthesis of Example 56.

Example 57

3-[1-(2,6-Dichloro-3-fluorophenyl)-ethyl]-5-[1-(1-methanesulfonylazetidin-3-yl)-1H-pyrazol-4-yl]-1H-pyrrolo[2,3-b]pyridine $^1$H NMR (400 MHz, CD$_3$OD): δ=1.89 (d, J=7.3 Hz, 3 H), 3.10 (s, 3 H), 4.36 (t, J=8.3 Hz, 2 H), 4.42 (ddd, J=9.2, 6.0, 3.5 Hz, 2 H), 5.22-5.34 (m, 2 H), 7.16-7.23 (m, 1 H), 7.38 (d, J=1.3 Hz, 1 H), 7.40 (d, J=2.0 Hz, 1 H), 7.44 (br. s., 1 H), 7.71 (s, 1 H), 7.92 (s, 1H), 8.33 (d, J=2.0 Hz, 1 H). MS (ES+): m/z 508.02 (100) [MH$^+$]. HPLC: $t_R$=3.51 min (ZQ3, polar_5 min).

Example 58

1-[3-(4-{3-[1-(2,6-Dichloro-3-fluorophenyl)-ethyl]-1H-pyrrolo[2,3-b]pyridin-5-yl}-pyrazol-1-yl)-azetidin-1-yl]-ethanone $^1$H NMR (400 MHz, CD$_3$OD): δ=1.89 (d, J=7.1 Hz, 3 H), 1.95 (s, 3 H), 4.33 (dd, J=10.6, 5.1 Hz, 1 H), 4.42-4.48 (m, 1 H), 4.57 (dd, J=9.3, 5.1 Hz, 1 H), 4.67 (t, J=8.7 Hz, 1 H), 5.23-5.33 (m, 2 H), 7.19 (t, J=8.6 Hz, 1 H), 7.37 (d, J=1.3 Hz, 1H), 7.38-7.49 (m, 2 H), 7.71 (s, 1 H), 7.95 (s, 1 H), 8.33 (s, 1 H). MS (ES+): m/z 472.07 (100) [MH$^+$]. HPLC: $t_R$=3.23 min (ZQ3, polar_5 min).

Example 59

3-(4-{3-[1-(2,6-Dichloro-3-fluorophenyl)ethyl]-1H-pyrrolo[2,3-b]pyridin-5-yl}-pyrazol-1-yl)-azetidine-1-carboxylic acid dimethylamide A mixture of 5-(1-azetidin-3-yl-1H-pyrazol-4-yl)-3-[1-(2,6-dichloro-3-fluorophenyl)ethyl]-1H-pyrrolo[2,3-b]pyridine (6.0 mg, 0.014 mmol), formic acid (1.4 µL, 0.037 mmol), TBTU (8.95 mg, 0.0279 mmol), DIPEA (0.02 mL, 0.09 mmol) and DMF (1 mL) was stirred at rt for 30 min. The solution was used directly for HPLC purification. The fractions containing the material were concentrated in vacuo, redissolved in THF and treated with 5M NaOH (0.1 mL) at rt for 10 min. The solution was neutralized with HCl, and loaded into an SCX cartridge. MeOH was used to wash, and the material was ejected with 2M NH$_3$ in MeOH to afford the title compound as a white solid. $^1$H NMR (400 MHz, CD$_3$OD): δ=1.89 (d, J=7.1 Hz, 3 H), 2.92 (s, 6 H), 4.33-4.40 (m, 2 H), 4.42-4.50 (m, 2 H), 5.16-5.25 (m, 1 H), 5.25-5.35 (m, 1 H), 7.15-7.22 (m, 1 H), 7.37 (d, J=1.5 Hz, 1 H), 7.38-7.53 (m, 2 H), 7.68 (s, 1 H), 7.94 (s, 1 H), 8.33 (s, 1H). MS (ES+): m/z 501.06 (100) [MH$^+$]. HPLC: $t_R$=3.35 min (ZQ3, polar_5 min).

Example 60

2-(4-{3-[1-(2,6-Dichloro-3-fluorophenyl)ethyl]-1H-pyrrolo[2,3-b]pyridin-5-yl}-pyrazol-1-yl)-2-methyl-propionic acid methyl ester Prepared from 5-bromo-3-[1-(2,6-dichloro-3-fluorophenyl)ethyl]-1H-pyrrolo[2,3-b]-pyridine and 2-methyl-2-[4-(4,4,5,5-tetramethyl[1,3,2]dioxaborolan-2-yl)pyrazol-1-yl]-propionic acid methyl ester according to the Suzuki coupling procedure described in Example 1. Purification by flash column chromatography using 0→70% EtOAc in hexanes afforded the title compound as a light yellow solid. MS (ES+): m/z 475.06/477.04 (100/68) [MH$^+$]. HPLC: $t_R$=2.51 min (ZQ3, polar_5 min).

2-Methyl-2-[4-(4,4,5,5-tetramethyl[1,3,2]dioxaborolan-2-yl)pyrazol-1-yl]propionic acid methyl ester A mixture of 4-(4,4,5,5-Tetramethyl[1,3,2]dioxaborolan-2-yl)-1H-pyrazole (5.0 g, 0.026 mol), 2-bromo-2-methylpropionic acid methyl ester (3.50 mL, 0.0270 mol), Cs$_2$CO$_3$ (12 g, 39 mmol) in DMF (200 mL) was heated at 90° C. overnight. Reaction mixture was concentrated in vacuo, water was added, and the mixture was extracted with EtOAc (3×50 mL). The organic layer was dried over Na$_2$SO$_4$ and concentrated in vacuo to afford the title compound as a light yellow solid. MS (ES$^+$): m/z 295.13, 296.16 (100, 50) [MH$^+$]. HPLC: $t_R$=3.35 min (ZQ3 polar_5 min).

Example 61

2-(4-{3-[1-(2,6-Dichloro-3-fluorophenyl)ethyl]-1H-pyrrolo[2,3-b]pyridin-5-yl}-pyrazol-1-yl)-2-methyl-propionic acid 2-(4-3-[1-(2,6-Dichloro-3-fluorophenyl)ethyl]-1H-pyrrolo[2,3-b]pyridin-5-yl pyrazol-1-yl)-2-methylpropionic acid methyl ester (80 mg, 0.0002 mol) was dissolved in EtOH (3 mL) at 0° C. and a solution of lithium hydroxide monohydrate (35 mg, 0.84 mmol) in H$_2$O (1 mL) was added. The reaction mixture was allowed to stir at 0° C. for 1 h. The pH was then adjusted to 5 by adding 2 N HCl and the organic solvent was removed in vacuo. The material was then extracting with DCM (30 mL×3). The organic layer was concentrated in vacuo to afford the title compound as a light yellow solid. MS (ES$^+$): m/z 461.03 (100) [MH$^+$]. HPLC: $t_R$=3.89 min (ZQ3 polar_5 min).

Example 62

2-(4-{3-[1-(2,6-Dichloro-3-fluorophenyl)ethyl]-1H-pyrrolo[2,3-b]pyridin-5-yl}-pyrazol-1-yl)-N-methyl-isobutyramide A mixture of 2-(4-{3-[1-(2,6-Dichloro-3-fluorophenyl)ethyl]-1H-pyrrolo[2,3-b]pyridin-5-yl}-pyrazol-1-yl)-2-methylpropionic acid (20 mg, 0.04 mmol), methylammonium chloride (14.6 mg, 0.217 mmol), TBTU (28 mg, 0.087 mmol), DIPEA (37.8 µL, 0.217 mmol) and DCM (0.6 mL, 9 mmol) was stirred at rt for 1 h. The solvent was then removed under reduced pressure and the resulting residue was purified by a flash chromatography (eluent: 2% MeOH in DCM) to give desired product. MS (ES$^+$): m/z 474.09, 476.03 (100, 90) [MH$^+$]. HPLC: t$_R$=3.45 min (ZQ3 polar_5 min). $^1$H NMR (400 MHz, CD$_3$OD): δ=1.81 (s, 6H), 1.88 (d, J=7.3 Hz, 3H), 2.71 (s, 3H), 5.29 (q, J=7.2 Hz, 1H), 7.14-7.23 (m, 1H), 7.36 (d, J=1.5 Hz, 1H), 7.43 (s, 2H), 7.65 (s, 1H), 8.00 (s, 1H), 8.39 (br. s., 1H).

Examples 63-64 were synthesized according to the procedure described for synthesis of Example 62.

Example 63

2-(4-{3-[1-(2,6-Dichloro-3-fluorophenyl)ethyl]-1H-pyrrolo[2,3-b]pyridin-5-yl}-pyrazol-1-yl)-N,N-dimethylisobutyramide MS (ES$^+$): m/z 488.10, 490.04 (100, 90) [MH$^+$]. HPLC: t$_R$=3.56 min (ZQ3 polar_5 min). $^1$H NMR (400 MHz, CD$_3$OD): δ=1.81 (s, 6H), 1.88 (d, J=7.3 Hz, 3H), 2.45 (br. s., 3H), 2.96 (br. s., 3H), 5.28 (q, J=7.2 Hz, 1H), 7.10-7.16 (m, 1H), 7.33 (d, J=1.3 Hz, 1H), 7.38 (br. s., 1H), 7.43 (d, J=2.0 Hz, 1H), 7.62 (s, 1H), 7.89 (s, 1H), 8.32 (d, J=2.0 Hz, 1H).

Example 64

2-(4-{3-[1-(2,6-Dichloro-3-fluorophenyl)ethyl]-1H-pyrrolo[2,3-b]pyridin-5-yl}-pyrazol-1-yl)-isobutyramide MS (ES$^+$): m/z 460.06, 462.03 (100, 90) [MH$^+$]. HPLC: t$_R$=3.33 min (ZQ3 polar_5 min). $^1$H NMR (400 MHz, DMSO): δ=2.53 (s, 6H), 2.65 (d, J=7.1 Hz, 3H), 5.99 (q, J=7.6 Hz, 1H), 7.61 (br. s., 1H), 7.97 (br. s., 1H), 8.14-8.25 (m, 2H), 8.43 (s, 1H), 8.94 (s, 1H), 9.26 (d, J=1.8 Hz, 1H), 12.31 (s, 1H).

Example 65

2-(4-{3-[1-(2,6-Dichloro-3-fluorophenyl)ethyl]-1H-pyrrolo[2,3-b]pyridin-5-yl}-pyrazol-1-yl)-2-methyl-propan-1-ol 2-(4-3-[1-(2,6-Dichloro-3-fluorophenyl)ethyl]-1H-pyrrolo[2,3-b]pyridin-5-yl pyrazol-1-yl)-2-methylpropionic acid methyl ester (Example 60) (20 mg, 0.04 mmol) was dissolved in THF (1.0 mL, 10 mmol). To this solution was added 2 M LiAlH$_4$ in THF (60 µL) at 0° C. The resulting mixture was stirred at rt for 1 h. The reaction mixture was concentrated in vacuo and purified by HPLC to obtain the title compound as a white solid. MS (ES$^+$): m/z 447.09, 449.04 (100, 90) [MH$^+$]. HPLC: t$_R$=3.50 min (ZQ3 polar_5 min). $^1$H NMR (400 MHz, CD$_3$OD): δ=1.57 (s, 6H), 1.88 (d, J=7.1 Hz, 3H), 3.75 (s, 2H), 5.28 (q, J=7.1 Hz, 1H), 7.18 (t, J=8.6 Hz, 1H), 7.35 (d, J=1.3 Hz, 1H), 7.36-7.47 (m, 2H), 7.58 (s, 1H), 7.91 (s, 1H), 8.34 (br.s., 1H).

Example 66

3-[(S)-1-(2,6-Dichloro-3-fluorophenyl)ethyl]-5-(1,2,5,6-tetrahydropyridin-3-yl)-1H-pyrrolo[2,3-b]pyridine A mixture of 5-(4,4,5,5-Tetramethyl-1,3,2-dioxaborolan-2-yl)-3,6-dihydro-2H-pyridine-1-carboxylic acid tert-butyl ester (0.0154 g, 0.0498 mmol), ((S)-1-{5-Bromo-3-[(S)-1-(2,6-dichloro-3-fluorophenyl)ethyl]pyrrolo[2,3-b]pyridine-1-carbonyl}-3-methyl-butyl)-carbamic acid 9H-fluoren-9-ylmethyl ester (0.020 g, 0.028 mmol), Pd(PPh$_3$)$_4$ (0.0048 g, 0.0041 mmol) and K$_2$CO$_3$ (0.0172 g, 0.124 mol) in DME (1.2 mL) and H$_2$O (0.3 mL) was stirred at 100° C. under microwave condition for 30 min. The reaction mixture was directly loaded onto Prep TLC (5% MeOH in DCM) to afford 10 mg crude product. The crude product was dissolved in DCM (2 mL) and treated with 4 M HCl in dioxane for 2 h at rt. The resulting solution was loaded onto a Prep TLC (20×20 cm plate, silica gel 500 µM, 5% 7 N NH$_3$ in MeOH in DCM) to afford the desired product. $^1$H-NMR (CD$_3$OD, 400 MHz): δ=1.86 (d, J=7.1 Hz, 3 H), 2.30 (m, 2 H), 2.99 (t, J=5.9 Hz, 2 H), 3.58 (m, 2 H), 5.26 (m, 1 H), 5.97-6.07 (m, 1 H), 7.15-7.24 (m, 2 H), 7.37 (d, J=1.3 Hz, 1 H), 8.15 (d, J=2.0 Hz, 1 H). MS (ES$^+$): m/z 390.07 (MH$^+$, $^{35}$Cl), 392.02 (MH$^+$, $^{37}$Cl), HPLC: t$_R$=2.50 min (ZQ3, polar_5 min).

5-(4,4,5,5-Tetramethyl-1,3,2-dioxaborolan-2-yl)-3,6-dihydro-2H-pyridine-1-carboxylic acid tert-butyl ester A mixture of Bis(pinacolato)diboron (0.864 g, 3.40 mmol), (1,1'-bis-(diphenyl-phosphino)ferrocene)palladium (0.29 g, 0.39 mmol), potassium acetate (0.642 g, 6.54 mmol) and 5-trifluoromethanesulfonyloxy-3,6-dihydro-2H-pyridine-1-carboxylic acid tert-butyl ester (0.600 g, 1.81 mmol) in 1,4-dioxane (20 mL) was degassed and refilled with N$_2$ three times. The resulting material was stirred at 80° C. for overnight. The reaction mixture was filtrated through a celite pad, concentrated in vacuo and purified by silica gel (Hexanes:EtOAc=9:1, v:v) to afford the desired product. $^1$H NMR (400 MHz, CDCl$_3$): δ=1.38 (s, 9 H), 2.01-2.19 (m, 2 H), 3.28-3.41 (m, 2 H), 3.89 (d, J=2.23 Hz, 2 H), 6.55 (br. s., 1 H).

5-Trifluoromethanesulfonyloxy-3,6-dihydro-2H-pyridine-1-carboxylic acid tert-butyl ester To solution of LDA (7.20 mmol) in THF (10 mL) was added a solution of 1-Boc-3-piperidone (1.20 g, 6.00 mmol) in THF (2 mL) dropwise at −78° C. The mixture was warmed up to rt and stirred for 30 min. The reaction mixture was then cooled down to −78° C. again and added a solution of N-phenylbis(trifluoromethanesulfonimide) (2.79 g, 7.80 mmol) in 13 mL THF. The resulting mixture was stirred for another 2.5 h. The resulting mixture was quenched by sat. aq. NaHCO$_3$ (20 mL), diluted with EtOAc (40 mL), washed with water again (20 mL×3) and brine (20 mL). The organic layer was dried over Na$_2$SO$_4$, concentrated in vacuo and purified by silica gel (eluent: Hexanes:EtOAc 9:1) to afford a mixture of the desired product and N-phenyl trifluoromethanesulfonimide (1:1). $^1$H NMR (400 MHz, CDCl$_3$): δ=1.48 (s, 9 H), 2.28 (m, 2 H), 3.48 (t, J=5.6 Hz, 2 H), 3.95-4.13 (m, 2 H), 5.92 (t, J=4.2 Hz, 1 H).

Example 67

5-{3-[(S)-1-(2,6-Dichloro-3-fluorophenyl)ethyl]-1H-pyrrolo[2,3-b]pyridin-5-yl}-3,6-dihydro-2H-pyridine-1-carboxamide A solution of 3-[(S)-1-(2,6-Dichloro-3-fluorophenyl)ethyl]-5-(1,2,5,6-tetrahydropyridin-3-yl)-1H-pyrrolo[2,3-b]pyridine (0.0030 g, 0.0077 mmol) in DCM (0.5 mL) was added a drop of TMS isocyanate. The reaction was stirred at 0° C. for 30 min. The solution was directly loaded onto Prep

47

TLC (20×20 cm, silica gel, 5% MeOH in DCM) to afford the desired product. $^1$H-NMR (CD$_3$OD, 400 MHz): δ=1.87 (d, J=7.1 Hz, 3 H), 2.22-2.44 (m, 2 H), 3.46-3.57 (m, 2H), 4.11-4.20 (m, 2 H), 5.27 (d, J=7.3 Hz, 1 H), 6.00 (t, J=2.0 Hz, 1 H), 7.11-7.24 (m, 1 H), 7.34 (dd, J=16.2, 1.8 Hz, 2 H), 8.19 (s, 1 H). MS (ES$^+$): m/z 433.04/434.96 [MH$^+$]. HPLC: t$_R$=3.23 min (ZQ3, polar_5 min).

Example 68

3-[(S)-1-(2,6-Dichloro-3-fluorophenyl)ethyl]-5-pyridin-4-yl-1H-pyrrolo[2,3-b]pyridine Example 68 was synthesized according to the Suzuki coupling method described above for the synthesis of example 66, using ((S)-1-{5-Bromo-3-[(S)-1-(2,6-dichloro-3-fluorophenyl)ethyl]pyrrolo[2,3-b]pyridine-1-carbonyl}-3-methyl-butyl)-carbamic acid 9H-fluoren-9-ylmethyl ester and 4-(4,4,5,5-Tetramethyl[1,3,2]dioxaborolan-2-yl)pyridine, except that the crude product was purified by HPLC. $^1$H NMR (400 MHz, CD$_3$OD): δ 8.48-8.59 (m, 3 H), 7.61 (d, J=2.0 Hz, 1H), 7.52 (dd, J=4.5, 1.5 Hz, 2H), 7.46-7.49 (m, 2 H), 7.20 (t, J=8.7 Hz, 1H), 5.34 (q, J=7.3 Hz, 1H), 1.91 (d, J=7.3 Hz, 3H). MS (ES+): m/z=386.19, 388.17 (100, 88) [MH$^+$]. HPLC: t$_R$=0.94 min (HPLC-ACQUITY, Purity).

Example 69

(4-{3-[(S)-1-(2,6-Dichloro-3-fluorophenyl)ethyl]-1H-pyrrolo[2,3-b]pyridin-5-yl}phenyl)piperazin-1-ylmethanone Example 69 was synthesized according to Suzuki coupling method described above for synthesis of example 66, using ((S)-1-{5-Bromo-3-[(S)-1-(2,6-dichloro-3-fluorophenyl)ethyl]pyrrolo[2,3-b]pyridine-1-carbonyl}-3-methylbutyl)carbamic acid 9H-fluoren-9-ylmethyl ester and 4-[4-(4,4,5,5-Tetramethyl[1,3,2]dioxaborolan-2-yl)benzoyl]piperazine-1-carboxylic acid tert-butyl ester. The crude material was purified by HPLC. MS (ES+): m/z=497.24, 499.25 (100, 69) [MH$^+$]. HPLC: t$_R$=0.72 min (HPLC-ACQUITY, Purity).

Example 70

2-(4-{3-[(S)-1-(2,6-Dichloro-3-fluorophenyl)ethyl]-1H-pyrrolo[2,3-b]-pyridin-5-yl}pyrazol-1-yl)ethanol A mixture of ((S)-1-{5-bromo-3-[(S)-1-(2,6-dichloro-3-fluorophenyl)ethyl]pyrrolo[2,3-b]pyridine-1-carbonyl}-3-methylbutyl)-carbamic acid 9H-fluoren-9-ylmethyl ester (190.0 mg, 0.262 mmol), 1-[2-(tetrahydropyran-2-yloxy)ethyl]-4-(4,4,5,5-tetramethyl-[1,3,2]dioxaborolan-2-yl)-1H-pyrazole (95.0 mg, 0.294 mol), Pd(PPh$_3$)$_4$ (20 mg, 0.010 mmol), potassium carbonate (181 mg, 1.31 mmol) in a mixed solvent of dioxane and water (v:v=4:1, dioxane:H$_2$O, 10 mL) was heated to 85° C. for 1 h. The organic solvent was removed and the material was transferred to a separatory funnel and extracted with DCM (20 mL×3). The organic layers were combined, dried (Na$_2$SO$_4$) and concentrated in vacuo to give a residue that was re-dissolved in dioxane (4 mL). 2M aq. HCl (1.0 mL) was added at rt, and the solution was allowed to stir for 1 h. The solvents were removed in vacuo, and the material was dry-loaded onto silica gel for column chromatography, eluting with 3-4% (7N NH$_3$ in MeOH)/DCM to reveal the title compound. MS (ES+): m/z=419.21, 421.19 (100, 85) [MH$^+$]. HPLC: t$_R$=0.92 min (HPLC-ACQUITY, Purity).

Example 71

4-(4-{3-[1-(2,6-Dichloro-3-fluorophenyl)ethyl]-1H-pyrrolo[2,3-b]pyridin-5-yl}-pyrazol-1-yl)-piperidine-1-carbaldehyde Example 71 was synthesized from 3-[(S)-1-(2,6-dichloro-3-fluorophenyl)ethyl]-5-(1-piperidin-4-yl-1H-pyrazol-4-yl)-1H-pyrrolo[2,3-b]pyridine (example 80) according to the method described for the synthesis of example 47. $^1$H NMR (400 MHz, CD$_3$OD): δ=1.85-2.08 (m, 5H), 2.12-2.28 (m, 2 H), 2.85-3.01 (m, 1 H), 3.33-3.41 (m, 1 H), 3.91 (d, J=10.4 Hz, 1H), 4.45 (br. s., 1 H), 4.52-4.62 (m, 1 H), 5.38 (d, J=6.8 Hz, 1 H), 7.26 (t, J=8.5 Hz, 1 H), 7.49 (br. s., 1 H), 7.72 (s, 1 H), 7.76 (s, 1 H), 8.04 (s, 1 H), 8.10 (br. s., 1 H), 8.13 (br. s., 1 H), 8.60 (br. s., 1 H). MS (ES+): m/z 486.05 (100) [MH$^+$]. HPLC: t$_R$=3.31 min (ZQ3, polar_5 min).

Example 72

4-(4-{3-[(S)-1-(2,6-Dichloro-3-fluorophenyl)ethyl]-1H-pyrrolo[2,3-b]pyridin-5-yl}-pyrazol-1-yl)-piperidine-1-carboxamide Example 72 was synthesized from 3-[(S)-1-(2,6-dichloro-3-fluorophenyl)ethyl]-5-(1-piperidin-4-yl-1H-pyrazol-4-yl)-1H-pyrrolo[2,3-b]pyridine (example 80) according to the method described for the synthesis of example 49. $^1$H NMR (400 MHz, CD$_3$OD): δ=1.95 (d, J=6.8 Hz, 3 H), 2.04 (br. s., 2 H), 2.17 (br. s., 2 H), 3.15 (br. s., 2H), 4.08-4.31 (m, 2 H), 4.53 (br. s., 1 H), 5.38 (d, J=6.8 Hz, 1 H), 7.26 (t, J=8.3 Hz, 1 H), 7.49 (br. s., 1 H), 7.72 (s, 1 H), 7.76 (s, 1 H), 8.04 (s, 1 H), 8.14 (br. s., 1 H), 8.60 (br. s., 1 H). MS (ES+): m/z 501.06 (100) [MH$^+$]. HPLC: t$_R$=3.15 min (ZQ3, polar_5 min).

Example 73

3-[(S)-1-(2,6-Dichloro-3-fluorophenyl)ethyl]-5-[1-(1-methane-sulfonylpiperidin-4-yl)-1H-pyrazol-4-yl]-1H-pyrrolo[2,3-b]pyridine Example 73 was synthesized from 3-[(S)-1-(2,6-dichloro-3-fluorophenyl)ethyl]-5-(1-piperidin-4-yl-1H-pyrazol-4-yl)-1H-pyrrolo[2,3-b]pyridine (example 80) according to the method described for the synthesis of example 50. $^1$H NMR (400 MHz, CD$_3$OD): δ=1.95 (d, J=7.1 Hz, 3 H), 2.05-2.18 (m, 2 H), 2.24 (d, J=12.1 Hz, 2 H), 2.90 (s, 3 H), 2.95-3.05 (m, 2 H), 3.88 (d, J=12.4 Hz, 2 H), 4.34-4.47 (m, 1 H), 5.34-5.42 (m, 1 H), 7.27 (t, J=8.7 Hz, 1 H), 7.50 (br. s., 1 H), 7.70 (d, J=1.3 Hz, 1 H), 7.75 (s, 1 H), 8.01 (d, J=1.3 Hz, 1 H), 8.13 (s, 1H), 8.58 (s, 1 H). MS (ES+): m/z 536.06 (100) [MH$^+$]. HPLC: t$_R$=3.52 min (ZQ3, polar_5 min).

Example 74

(4-{3-[(S)-1-(2,6-Dichloro-3-fluorophenyl)ethyl]-1H-pyrrolo[2,3-b]pyridin-5-yl}-pyrazol-1-yl)-acetic acid A mixture of N—((S)-1-{5-bromo-3-[(S)-1-(2,6-dichloro-3-fluorophenyl)ethyl]pyrrolo[2,3-b]pyridine-1-carbonyl}-3-methylbutyl)-2-(9H-fluoren-9-yl)-acetamide (150.0 mg, 0.212 mmol) and aq 5M NaOH (0.42 mL, 1.1 mmol) in THF (5 mL) was cooled to 0° C. and stirred for 1 h. The organic solvent was removed in vacuo, and the material was transferred to a separatory funnel, extracting with DCM and water. The organic layer was concentrated in vacuo, and [4-(4,4,5, 5-tetramethyl[1,3,2]dioxaborolan-2-yl)pyrazol-1-yl]-acetic acid ethyl ester (89.1 mg, 0.318 mmol), Pd(PPh$_3$)$_4$ (20 mg, 0.02 mmol), potassium fluoride (61.6 mg, 1.06 mmol) and 4:1 dioxane/H$_2$O were added, and the mixture was heated to 90° C. for 2 h. The organic solvent was removed in vacuo, and the material was transferred to a separatory funnel and extracted with DCM and water. The organic layer was dry-loaded onto silica gel, and purified via column chromatography, eluting with 2% (7N NH$_3$ in MeOH)/DCM. The fractions containing the pure product were concentrated in vacuo, redissolved in EtOH/H$_2$O (8 mL), and LiOH (44.5 mg, 1.06 mmol) was added at 0° C. and stirred for 20 min. The pH of the solution was lowered to pH 5 by addition of 2M HCl, and the organic solvent was removed in vacuo. The material was transferred to a separatory funnel and extracted with DCM and brine. The organic layer was concentrated in vacuo to afford the title compound as a yellow solid. $^1$H NMR (400 MHz, CD$_3$OD): δ=1.88 (d, J=7.1 Hz, 3 H), 4.83 (s, 2 H), 5.29 (q, J=7.1 Hz, 1 H), 7.19 (t, J=8.6 Hz, 1 H), 7.36 (d, J=1.5 Hz, 1 H), 7.39-7.53 (m, 2 H), 7.57 (s, 1 H), 7.82 (s, 1H), 8.34 (d, J=2.0 Hz, 1 H). MS (ES+): m/z 433.00 (100) [MH$^+$]. HPLC: t$_R$=3.53 min (ZQ3, polar_5 min).

Example 75

2-(4-{3-[(S)-1-(2,6-Dichloro-3-fluorophenyl)ethyl]-1H-pyrrolo[2,3-b]-pyridin-5-yl}-pyrazol-1-yl)-acetamide A mixture of (4-{3-[(S)-1-(2,6-dichloro-3-fluorophenyl)ethyl]-1H-pyrrolo[2,3-b]pyridin-5-yl}-pyrazol-1-yl)-acetic acid (10.0 mg, 0.0231 mmol), dimethylamine hydrochloride (9.41 mg, 0.115 mmol), TBTU (14.8 mg, 0.0462 mmol), DIPEA (0.021 mL, 0.115 mmol) and DCM (3 mL) was stirred at rt for 30 min. The solution was concentrated in vacuo, redissolved in MeOH and purified via HPLC. The fractions containing the pure product were concentrated in vacuo to afford the title compound as a white solid. $^1$H NMR (400 MHz, CD$_3$OD): δ=1.89 (d, J=7.1 Hz, 3 H), 2.99 (s, 3 H), 3.14 (s, 3 H), 5.16 (s, 2 H), 5.29 (q, J=7.3 Hz, 1 H), 7.13-7.23 (m, 1 H), 7.38 (d, J=1.3 Hz, 1 H), 7.39-7.52 (m, 2 H), 7.63 (s, 1 H), 7.81 (s, 1 H), 8.34 (d, J=1.8 Hz, 1 H). MS (ES+): m/z 460.02 (100) [MH$^+$]. HPLC: t$_R$=3.26 min (ZQ3, polar_5 min).

Examples 76-79 were synthesized according to the procedure described for synthesis of Example 75.

Example 76

2-(4-{3-[(S)-1-(2,6-Dichloro-3-fluorophenyl)ethyl]-1H-pyrrolo[2,3-b]-pyridin-5-yl}-pyrazol-1-yl)-N-methylacetamide $^1$H NMR (400 MHz, CD$_3$OD): δ=1.88 (d, J=7.3 Hz, 3 H), 2.77 (s, 3 H), 4.86 (s, 2 H), 5.22-5.34 (m, 1 H), 7.19 (t, J=8.7 Hz, 1 H), 7.37 (d, J=1.5 Hz, 1 H), 7.39-7.55 (m, 2 H), 7.65 (s, 1 H), 7.88 (s, 1 H), 8.34 (br. s., 1 H). MS (ES+): m/z 446.02 (100) [MH$^+$]. HPLC: t$_R$=3.18 min (ZQ3, polar_5 min).

Example 77

2-(4-{3-[(S)-1-(2,6-Dichloro-3-fluorophenyl)ethyl]-1H-pyrrolo[2,3-b]-pyridin-5-yl}-pyrazol-1-yl)-acetamide $^1$H NMR (400 MHz, CD$_3$OD): δ=1.88 (d, J=7.3 Hz, 3 H), 4.90 (s, 2 H), 5.29 (q, J=7.1 Hz, 1 H), 7.19 (t, J=8.6 Hz, 1 H), 7.37 (d, J=1.3 Hz, 1 H), 7.38-7.56 (m, 2 H), 7.64 (s, 1 H), 7.87 (s, 1 H), 8.34 (d, J=2.0 Hz, 1 H). MS (ES+): m/z 431.98 (100) [MH$^+$]. HPLC: t$_R$=3.08 min (ZQ3, polar_5 min).

Example 78

2-(4-{3-[(S)-1-(2,6-Dichloro-3-fluorophenyl)ethyl]-1H-pyrrolo[2,3-b]pyridin-5-yl}-pyrazol-1-yl)-1-morpholin-4-ylethanone $^1$H NMR (400 MHz, CD$_3$OD): δ=1.88 (d, J=7.3 Hz, 3 H), 3.58-3.63 (m, 4 H), 3.70 (ddd, J=12.0, 4.8, 4.7 Hz, 4 H), 5.16 (s, 2 H), 5.29 (q, J=7.3 Hz, 1 H), 7.14-7.22 (m, 1 H), 7.37 (d, J=1.5 Hz, 1 H), 7.38-7.55 (m, 2 H), 7.62 (s, 1 H), 7.80 (s, 1 H), 8.33 (d, J=2.0 Hz, 1H). MS (ES+): m/z 502.02 (100) [MH$^+$]. HPLC: t$_R$=3.25 min (ZQ3, polar_5 min).

Example 79

2-(4-{3-[(S)-1-(2,6-Dichloro-3-fluorophenyl)ethyl]-1H-pyrrolo[2,3-b]-pyridin-5-yl}-pyrazol-1-yl)-1-(4-methylpiperazin-1-yl)ethanone $^1$H NMR (400 MHz, CD$_3$OD): δ=1.88 (d, J=7.3 Hz, 3 H), 2.63 (s, 3 H), 2.87 (d, J=2.8 Hz, 2 H), 2.93 (br. s., 2 H), 3.76 (br. s., 4 H), 5.19 (s, 2 H), 5.29 (q, J=7.3 Hz, 1 H), 7.18 (t, J=8.6 Hz, 1 H), 7.37 (d, J=1.5 Hz, 1 H), 7.39-7.54 (m, 2 H), 7.64 (s, 1 H), 7.80 (s, 1 H), 8.33 (d, J=1.5 Hz, 1 H). MS (ES+): m/z 515.05 (100) [MH$^+$]. HPLC: t$_R$=2.50 min (ZQ3, polar_5 min).

Example 80

3-[(S)-1-(2,6-Dichloro-3-fluorophenyl)ethyl]-5-(1-piperidin-4-yl-1H-pyrazol-4-yl)-1H-pyrrolo[2,3-b]pyridine ((S)-1-{5-Bromo-3[(S)-1-(2,6-dichloro-3-fluorophenyl)ethyl]-pyrrolo[2,3-b]pyridine-1-carbonyl}-3-methylbutyl)carbamic acid 9H-fluoren-9-ylmethyl ester was treated with 4-[4-(4,4,5,5-tetramethyl-[1,3,2]dioxaborolan-2-yl)pyrazol-1-yl]piperidine hydrochloride according to typical Suzuki coupling procedure described for synthesis of 3-[1-(2,6-Dichlorophenyl)ethyl]-5-(1-piperidin-4-yl-1H-pyrazol-4-yl)-1H-pyrrolo[2,3-b]pyridine in example 1, to give the title compound. $^1$H NMR (400 MHz, DMSO-d$_6$): δ=1.70-1.80 (m, 2H), 1.83 (d, J=7.1 Hz, 3H), 1.94 (dd, J=11.6, 2.0 Hz, 2H), 2.08 (br s, 1H), 2.57 (td, J=12.3, 2.3 Hz, 2H), 3.03 (ddd, J=12.6, 2.9, 2.7 Hz, 2H), 4.17 (tt, J=11.6, 4.1 Hz, 1H), 5.16 (q, J=7.2 Hz, 1H), 7.33 (d, J=1.8 Hz, 1H), 7.36-7.44 (m, 2H), 7.48-7.65 (m, 1H), 7.56 (d, J=0.5 Hz, 1H), 8.03 (s, 1H), 8.39 (d, J=2.0 Hz, 1H), 11.51 (d, J=1.8 Hz, 1H). MS (ES+): m/z 458.07/460.05 (100/70) [MH$^+$]. HPLC: t$_R$=2.53 min (ZQ3, polar_5 min).

Example 81

3-[(R)-1-(2,6-Dichloro-3-fluorophenyl)ethyl]-5-(1-piperidin-4-yl-1H-pyrazol-4-yl)-1H-pyrrolo[2,3-b]pyridine A mixture of ((S)-1-{5-bromo-3-[(R)-1-(2,6-dichloro-3-fluorophenyl)ethyl]pyrrolo[2,3-b]pyridine-1-carbonyl}-3-methylbutyl)carbamic acid 9H-fluoren-9-ylmethyl ester (20.4 mg, 0.0283 mmol), 4-[4-(4,4,5,5-tetramethyl-[1,3,2] dioxaborolan-2-yl)-pyrazol-1-yl]-piperidine hydrochloride (17.7 mg, 0.0565 mmol), Pd(PPh$_3$)$_4$ (3 mg, 0.003 mmol), potassium carbonate (19.5 mg, 0.141 mmol) and 4:1 dioxane:

H₂O (4 mL) was heated to 85° C. for 2 h. The organic solvent was removed in vacuo, and the material was transferred to a separatory funnel, extracting with DCM. The organic layer was dry-loaded onto silica gel, and column chromatography was used to purify, eluting with 5-10% (7N NH₃ in MeOH)/DCM. The fractions containing the pure product were concentrated in vacuo to afford the title compound as a white solid. ¹H NMR (400 MHz, CD₃OD): δ=1.88 (d, J=7.3 Hz, 3 H), 1.91-2.02 (m, 2H), 2.07-2.15 (m, 2 H), 2.78 (td, J=12.6, 2.3 Hz, 2 H), 3.21 (d, J=12.9 Hz, 2 H), 4.31 (tt, J=11.7, 4.0 Hz, 1 H), 5.27 (q, J=7.2 Hz, 1 H), 7.19 (t, J=8.6 Hz, 1 H), 7.34-7.39 (m, 2 H), 7.42 (br. s., 1 H), 7.56 (s, 1 H), 7.87 (s, 1 H), 8.31 (d, J=1.8 Hz, 1 H). MS (ES+): m/z 458.05/460.03 (100/68) [MH⁺]. HPLC: $t_R$=2.52 min (ZQ3, polar__5 min).

Example 82

4-(4-{3-[(R)-1-(2,6-Dichloro-3-fluorophenyl)ethyl]-1H-pyrrolo[2,3-b]-pyridin-5-yl}-pyrazol-1-yl)-piperidine-1-carbaldehyde Example 82 was synthesized from 3-[(R)-1-(2,6-dichloro-3-fluorophenyl)ethyl]-5-(1-piperidin-4-yl-1H-pyrazol-4-yl)-1H-pyrrolo[2,3-b]pyridine (example 81) according to the method described for the synthesis of example 47. ¹H NMR (400 MHz, CD₃OD): δ=1.85-2.08 (m, 5H), 2.14-2.26 (m, 2 H), 2.92-3.00 (m, 1 H), 3.33-3.40 (m, 1 H), 3.91 (d, J=13.1 Hz, 1 H), 4.47 (d, J=12.9 Hz, 1 H), 4.56 (t, J=11.1 Hz, 1 H), 5.38 (q, J=7.1 Hz, 1 H), 7.26 (t, J=8.6 Hz, 1 H), 7.50 (br. s., 1 H), 7.72 (s, 1 H), 7.75 (s, 1 H), 8.03 (s, 1 H), 8.09 (br. s., 1 H), 8.12 (s, 1 H), 8.59 (s, 1 H). MS (ES+): m/z 486.05 (100) [MH⁺]. HPLC: $t_R$=3.31 min (ZQ3, polar__5 min).

Example 83

3-[(R)-1-(2,6-Dichloro-3-fluorophenyl)ethyl]-5-[1-(1-methane-sulfonylpiperidin-4-yl)-1H-pyrazol-4-yl]-1H-pyrrolo[2,3-b]pyridine Example 83 was synthesized from 3-[(R)-1-(2,6-dichloro-3-fluorophenyl)ethyl]-5-(1-piperidin-4-yl-1H-pyrazol-4-yl)-1H-pyrrolo[2,3-b]pyridine (example 81) according to the method described for the synthesis of example 50. ¹H NMR (400 MHz, CD₃OD): δ=1.88 (d, J=7.1 Hz, 3 H), 2.07-2.26 (m, 4 H), 2.88-2.92 (m, 3 H), 2.94-3.03 (m, 2 H), 3.87 (d, J=12.4 Hz, 2H), 4.29-4.40 (m, 1 H), 5.29 (q, J=7.0 Hz, 1 H), 7.19 (t, J=8.6 Hz, 1 H), 7.37 (d, J=1.5 Hz, 1 H), 7.38-7.51 (m, 2 H), 7.58 (s, 1 H), 7.92 (s, 1 H), 8.32 (br. s., 1 H). MS (ES+): m/z 535.99 (100) [MH⁺]. HPLC: $t_R$=3.52 min (ZQ3, polar__5 min).

Example 84

4-(4-{3-[(R)-1-(2,6-Dichloro-3-fluorophenyl)ethyl]-1H-pyrrolo[2,3-b]-pyridin-5-yl}-pyrazol-1-yl)-piperidine-1-carboxamide Example 84 was synthesized from 3-[(R)-1-(2,6-dichloro-3-fluorophenyl)ethyl]-5-(1-piperidin-4-yl-1H-pyrazol-4-yl)-1H-pyrrolo[2,3-b]pyridine (example 81) according to the method described for the synthesis of example 49. ¹H NMR (400 MHz, CD₃OD): δ=1.89 (d, J=7.1 Hz, 3 H), 1.93-2.05 (m, 2 H), 2.11 (d, J=12.4 Hz, 2 H), 3.01 (t, J=12.9 Hz, 2 H), 4.17 (d, J=12.9 Hz, 2 H), 4.41 (t, J=11.6 Hz, 1 H), 5.29 (d, J=7.1 Hz, 1 H), 7.20 (t, J=8.6 Hz, 1 H), 7.37 (s, 1 H), 7.40 (d, J=1.8 Hz, 1 H), 7.46 (br. s., 1 H), 7.58 (s, 1 H), 7.91 (s, 1 H), 8.32 (br. s., 1H). MS (ES+): m/z 501.05 (100) [MH⁺]. HPLC: $t_R$=3.16 min (ZQ3, polar__5 min).

Example 85

2-(4-{3-[(S)-1-(2,6-Dichloro-3-fluorophenyl)ethyl]-1H-pyrrolo[2,3-b]-pyridin-5-yl}-pyrazol-1-yl)-2-methylpropan-1-ol To a solution of 2-(4-{3-[(S)-1-(2,6-Dichloro-3-fluorophenyl)ethyl]-1H-pyrrolo[2,3-b]-pyridin-5-yl}-pyrazol-1-yl)-2-methylpropionic acid methyl ester (64.0 mg, 0.135 mmol) in THF (3.0 mL) was added 2 M of LiAlH₄ in THF (0.20 mL, 0.40 mmol) under N₂ at −78° C. The reaction mixture was stirred for 1 h at −78° C., quenched by adding water, warmed to rt, filtered, and concentrated in vacuo. Purification of the residue by HPLC afforded the title compound. A crystal structure of the title compound bound to cMet confirmed the absolute configuration as shown. ¹H NMR (400 MHz, CD₃OD): δ=1.58 (s, 6 H), 1.88 (d, J=7.2 Hz, 3 H), 3.75 (s, 2 H), 5.28 (q, J=7.2 Hz, 1H), 7.18 (t, J=8.6 Hz, 1 H), 7.35 (d, J=1.3 Hz, 1 H), 7.37-7.39 (m, 1H), 7.41 (brs, 1H), 7.58 (s, 1 H), 7.91 (s, 1 H), 8.32 (d, J=1.8 Hz, 1H). MS (ES⁺): m/z 447.09/449.04 (100/70) [MH⁺]. HPLC: $t_R$=3.50 min (ZQ3 polar__5 min).

The 2-(4-{3-[(S)-1-(2,6-Dichloro-3-fluorophenyl)ethyl]-1H-pyrrolo[2,3-b]pyridin-5-yl}-pyrazol-1-yl)-2-methylpropionic acid methyl ester was prepared from 5-bromo-3-[(S)-1-(2,6-dichloro-3-fluorophenyl)ethyl]-1H-pyrrolo[2,3-b]pyridine and 2-methyl-2-[4-(4,4,5,5-tetramethyl[1,3,2]dioxaborolan-2-yl)pyrazol-1-yl]propionic acid methyl ester as described in Example 60.

Example 86 trans-4-(4-{3-[(1S)-1-(2,6-dichloro-3-fluorophenyl)ethyl]-1H-pyrrolo[2,3-b]pyridin-5-yl}-1H-pyrazol-1-yl)cyclohexanol A mixture of 3-[(S)-1-(2,6-Dichloro-3-fluorophenyl)ethyl]-5-(4,4,5,5-tetramethyl-[1,3,2]dioxaborolan-2-yl)-1H-pyrrolo[2,3-b]pyridine (60.0 mg, 0.138 mmol), trans-4-(4-iodo-pyrazol-1-yl)cyclohexanol (52.4 mg, 0.179 mmol), Pd(PPh₃)₄ (8 mg, 0.007 mmol), potassium carbonate (57.2 mg, 0.414 mmol) and 4:1 dioxane:water (7 mL) was heated to 90° C. for 2 h. The organic solvent was removed in vacuo, and the material was transferred to a separatory funnel, extracting with DCM and sat. NaHCO₃ solution. The organic layer was dry-loaded onto silica gel, and column chromatography was used to purify, eluting with 3-4% (7N NH₃ in MeOH)/DCM. The resulting solid was triturated with MeOH to give the title compound. ¹H NMR (400 MHz, CD₃OD): δ=1.47-1.59 (m, 2 H), 1.88 (d, J=6.8 Hz, 3 H), 1.90-2.03 (m, 2H), 2.10-2.22 (m, 4 H), 3.66 (tt, J=10.9, 4.2 Hz, 1 H), 4.17 (tt, J=11.6, 4.0 Hz, 1 H), 5.27 (q, J=7.0 Hz, 1 H), 7.18 (dd, J=8.4, 8.8 Hz, 1 H), 7.38 (d, J=1.3 Hz, 1 H), 7.44 (d, J=2.0 Hz, 1 H), 7.46 (br. s., 1 H), 7.54 (d, J=0.8 Hz, 1 H), 7.87 (d, J=0.8 Hz, 1 H), 8.32 (d, J=2.0 Hz, 1 H). MS (ES⁺): m/z 473.01/475.04 (100/70) [MH⁺]. HPLC: $t_R$=3.36 min (ZQ3, polar__5 min). This material was redissolved in DCM. 2.0 M of HCl in Et₂O (0.8 mL) was added at rt and stirred for 20 min. The mixture was concentrated in vacuo to afford the title compound as an HCl salt.

Trans- and cis-4-(4-Iodopyrazol-1-yl)cyclohexanol

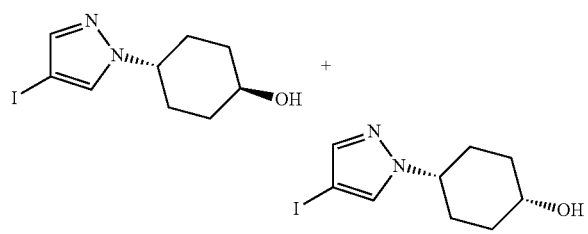

Sodium borohydride (0.29 g, 7.6 mmol) was added into the EtOH (20 mL) solution of 4-(4-iodopyrazol-1-yl)cyclohexanone (4.5 g, 15.5 mmol) at RT under an atmosphere of nitrogen. The mixture was stirred at RT for 2 h. Work-up: Solvent was evaporated and added water to the residue and extracted with EtOAc (3×60 mL). The combined organic extracts were dried over $Na_2SO_4$, filtered, and concentrated in vacuo to give an off-white solid. This material was purified by column chromatography on silica gel by eluting with 40% EtOAc/hexanes. The first (less polar) spot obtained was identified as cis isomer and the second (more polar) spot obtained was identified as trans isomer. Cis-isomer: $^1$H NMR (300 MHz, CDCl$_3$): δ=1.63-1.74 (m, 4H), 1.87-1.96 (m, 4H), 2.09-2.19 (m, 2H), 4.07-4.20 (m, 2H), 7.50 (s, 2H). Trans-isomer: colorless solid, mp. 82-86° C. $^1$H NMR (400 MHz, CDCl$_3$): δ=1.42-1.51 (m, 2 H), 1.79 (brs, 1 H), 1.77-1.99 (m, 2H), 2.09-2.22 (m, 4 H), 3.74 (br.tt, J=10.8, 4.0 Hz, 1 H), 4.13 (tt, J=11.6, 3.8 Hz. 1 H), 7.44 (d, J=0.4 Hz, 1 H), 7.50 (d, J=0.4 Hz, 1 H). MS (ES+): m/z=293.11 [MH$^+$]. HPLC: $t_R$=2.58 min (polar_5 min, ZQ3).

4-(4-Iodopyrazol-1-yl)cyclohexanone

A mixture of 1-(1,4-dioxaspiro[4.5]dec-8-yl)-4-iodo-1H-pyrazole (3.0 g, 8.9 mmol), pyridinium p-toluenesulfonate (4.5 g, 17.9 mmol), acetone (100 mL) and H$_2$O (100 mL) was heated at 60° C. overnight. Work-up: Solvent was evaporated and the residue was extracted with EtOAc (3×60 mL). The combined extracts were washed with water (3×50 mL), brine (50 mL), dried over Na$_2$SO$_4$, filtered, and concentrated in vacuo to give the title compound as white solid. It was used in the next step without further purification. $^1$H NMR (400 MHz, CDCl$_3$): δ=2.23-2.63 (m, 8 H), 4.57-4.64 (m, 1 H), 7.51 (s, 1 H), 7.54 (s, 1 H). MS (ES+): m/z=291.09 (100). HPLC: $t_R$=2.79 min (polar_5 min, ZQ3).

1-(1,4-Dioxaspiro[4.5]dec-8-yl)-4-iodo-1H-pyrazole

A mixture of 1,4-dioxaspiro[4.5]dec-8-yl 4-methylbenzenesulfonate (prepared according to U.S. Pat. No. 4,360,531) (2.0 g, 6.4 mmol), 4-iodopyrazole (1.36 g, 7.0 mmol), K$_2$CO$_3$ (1.06 g, 7.7 mmol), and 18-crown-6 (0.2 g, 0.7 mmol) in DMF (5 mL) was heated under nitrogen at 50° C. for 16 h. Water (50 mL) was added to the reaction mixture, which was then extracted with EtOAc (3×40 mL). The combined EtOAc extracts were washed with water (30 mL), dried over Na$_2$SO$_4$, filtered, and concentrated in vacuo. The residue was purified by column chromatography on silica gel using EtOAc/CH$_2$Cl$_2$ (1:9) to give the title compound. $^1$H NMR (CDCl$_3$, 400 MHz): δ=1.67-1.76 (m, 2 H), 1.84-1.91 (m, 2 H), 1.99-2.17 (m, 4 H), 3.95-3.99 (m, 4 H), 4.18-4.27 (m, 1 H). MS (ES+): m/z=334.96 (100) [MH$^+$]. HPLC: $t_R$=3.26 min (polar_5 min, ZQ3).

Example 87 cis-4-(4-{3-[(1S)-1-(2,6-dichloro-3-fluorophenyl)ethyl]-1H-pyrrolo[2,3-b]pyridin-5-yl}-1H-pyrazol-1-yl)cyclohexanol The title compound was prepared following the procedure for example 86, using cis-4-(4-Iodopyrazol-1-yl)cyclohexanol instead of the trans isomer.
$^1$H NMR (400 MHz, CD$_3$OD): δ=1.58-1.77 (m, 2 H), 1.87 (d, J=7.0 Hz, 3 H), 1.83-1.95 (m, 4 H), 2.06-2.34 (m, 2 H), 4.00 (brs, 1 H), 4.18 (tt, J=11.6, 4.0 Hz, 1 H), 5.26 (d, J=7.1 Hz, 1 H), 7.17 (t, J=8.6 Hz, 1 H), 7.35 (d, J=1.6 Hz, 1 H), 7.38 (d, J=1.6 Hz, 1 H), 7.42 (brs, 1 H), 7.55 (s, 1 H), 7.85 (s, 1 H), 8.32 (d, J=2.0 Hz, 1 H). MS (ES+): m/z 473.05/475.00 (100/71) [MH$^+$]. HPLC: $t_R$=3.45 min (ZQ3, polar_5 min).

Example 88

3-[1-(2,6-Dichloro-3-fluorophenyl)ethyl]-5-pyridin-3-yl-1H-pyrrolo[2,3-b]pyridine Example 88 was synthesized according to the method described for Example 2. MS (ES+): m/z=386.19, 388.19 (100, 82) [MH$^+$]. HPLC: $t_R$=0.91 min (HPLC-ACQUITY, Purity).

Example 89

4-(4-{3-[1-(2,6-Dichloro-3-fluorophenyl)ethyl]-1H-pyrrolo[2,3-b]pyridin-5-yl}-pyrazol-1-yl)cyclohexanone A 20 ml sealable vial was charged with 3-[1-(2,6-Dichloro-3-fluorophenyl)ethyl]-5-(4,4,5,5-tetramethyl[1,3,2]dioxaborolan-2-yl)-1H-pyrrolo[2,3-b]pyridine (80.0 mg, 0.156 mmol), 4-(4-Iodopyrazol-1-yl)cyclohexanone (52.5 mg, 0.172 mmol), Pd(PPh$_3$)$_4$ (12.0 mg, 0.0103 mmol), potassium carbonate (71.8 mg, 0.514 mmol), and 4:1 dioxane:water (5 mL). The cap was sealed and the vial was evacuated and backfilled with nitrogen (3×). After that, the vial was heated at 90° C. for 2 h. The reaction mixture was partitioned between EtOAc/H$_2$O (15 ml/10 ml). The aqueous phase was extracted with EtOAc (10 ml). The combined organic extracts were washed with water (10 ml) and brine (10 ml), dried over MgSO$_4$, filtered, and concentrated in vacuo to give a brown oil that was purified by prep. TLC eluting with 4% MeOH/DCM to give the title compound. $^1$H NMR (400 MHz, CDCl$_3$): δ=1.88 (d, J=7.2 Hz, 3H), 2.31-2.68 (m, 8 H), 4.64 (tt, J=11.8, 4.0 Hz, 1 H), 5.28 (q, J=7.2 Hz, 1 H), 7.01 (dd, J=8.0 & 8.8 Hz, 1 H), 7.30 (s, 1 H), 7.32 (brs, 1 H), 7.48 (s, 1 H), 7.60 (d, J=0.8 Hz, 1 H), 7.66 (d, J=0.8 Hz, 1 H), 8.41 (brs, 1 H), 9.77 (brs, 1 H). MS (ES+): m/z=471.16/473.11 (100/68) [MH$^+$]. HPLC: $t_R$=3.39 min (polar_5 min, ZQ3).

Example 90

(S)-3-(4-{3-[(S)-1-(2,6-Dichloro-3-fluorophenyl)ethyl]-1H-pyrrolo[2,3-b]pyridin-5-yl}-pyrazol-1-yl)-propane-1,2-diol A mixture of 5-Bromo-3-[(S)-1-(2,6-dichloro-3-fluorophenyl)-ethyl]-1H-pyrrolo[2,3-b]pyridine (45.0 mg, 0.116 mmol), 1-{[(4S)-2,2-dimethyl-1,3-dioxolan-4-yl]methyl}-4-(4,4,5,5-tetramethyl-1,3,2-dioxaborolan-2-yl)-1H-pyrazole (71.5 mg, 0.232 mmol), Pd(PPh$_3$)$_4$ (7 mg, 0.006 mmol), potassium carbonate (48.1 mg, 0.348 mmol) and 4:1 Dioxane:water (7 mL) was heated to 90° C. for 2 h. The solution was allowed to cool to rt. 2 M of HCl in water (4 mL) was added until pH 2, and the mixture was stirred at rt overnight. The solution was passed through a SCX cartridge that was washed with MeOH, and the product was eluted with 2M NH$_3$ in MeOH. The material was dry-loaded onto silica gel for column chromatography, eluting with 5% (7N NH$_3$ in MeOH)/DCM. The fractions containing the pure product were concentrated in vacuo, redissolved in DCM, and 2.0 M of HCl in Et$_2$O (0.4 mL) was added. The solution was stirred at rt for 20 min and concentrated in vacuo to afford the title compound as an HCl salt. $^1$H NMR (400 MHz, CD$_3$OD): δ=1.87 (d, J=7.1 Hz, 3 H), 3.52 (dd, J=5.3, 1.3 Hz, 2 H), 3.95-4.02 (m, 1H), 4.13 (dd, J=14.1, 7.6 Hz, 1 H), 4.31 (dd, J=14.0, 4.2 Hz, 1H), 5.27 (q, J=7.1 Hz, 1 H), 7.17 (dd, J=8.6, 8.6 Hz, 1H), 7.35 (d, J=1.3 Hz, 1 H), 7.37 (d, J=2.0 Hz, 1 H), 7.41 (br. s., 1 H), 7.59 (s, 1 H), 7.82 (s, 1 H), 8.31 (d, J=2.0 Hz, 1 H). MS (ES+): m/z=448.99/451.01 (100/68) [MH$^+$]. HPLC: t$_R$=3.05 min (polar_5 min, ZQ3).

1-{[(4S)-2,2-dimethyl-1,3-dioxolan-4-yl]methyl}-4-(4,4,5,5-tetramethyl-1,3,2-dioxaborolan-2-yl)-1H-pyrazole A solution of 4-(4,4,5,5-Tetramethyl[1,3,2]dioxaborolan-2-yl)-1H-pyrazole (9.24 g, 47.6 mmol), (R)-(−)-(2,2-Dimethyl-1,3-dioxolan-4-yl)methyl p-toluenesulfonate (15.00 g, 52.38 mmol) and CsHCO$_3$ (23.3 g, 71.4 mmol) in anhydrous DMF (236 mL) was heated to 100° C. for 16 h. The reaction mixture was allowed to cool to rt and partitioned between EtOAc and H$_2$O and separated. The aqueous was re-extracted with EtOAc (3×) and the combined organic fractions were washed with H$_2$O (2×) and brine (2×), dried over Na$_2$SO$_4$, filtered and concentrated in vacuo resulting in the title compound as an orange oil. It was used in the next step without further purification. $^1$H NMR (400 MHz, CDCl$_3$): δ=1.31 (s, 12H), 1.33 (s, 3H), 1.39 (s, 3H), 3.78 (dd, J=8.8, 5.9 Hz, 1H), 4.07 (dd, J=8.8, 6.2 Hz, 1H), 4.23-4.35 (m, 2H), 4.47 (quint, J=5.8 Hz, 1H), 7.78 (s, 1H), 7.81 (s, 1H).

Biological Properties

In some aspects, compounds of the invention are inhibitors of kinases, including at least one of the c-MET, and RON kinases.

In some aspects, compounds of the invention are inhibitors of kinases, including at least one of c-MET, RON, Tie-2, Flt3, FGFR3, Abl, Aurora A, Aurora B, Jak2, Alk, c-Src, IGF-1R, c-MET, RON, PAK1, PAK2, and TAK1 kinases.

In some aspects, compounds of the invention are selective inhibitors of c-MET and/or RON. In some embodiments, the compound is a selective inhibitor c-MET and/or RON over other kinase targets, such as KDR.

In some aspects, compounds of the invention inhibit epithelial to mesenchymal transition.

The activities of exemplary compounds of the present invention against Ron and c-Met determined at Invitrogen using the Z'-LYTE™ kinase assay platform are shown in Table 1: A, IC$_{50}$≤0.1 μM; B, 0.1 μM<IC$_{50}$≤1 μM; C, 1 μM<IC$_{50}$≤10 μM; D, IC$_{50}$>10 μM. The assays were conducted at an ATP concentration of 100 μM. The Example # of Table 1 corresponds to the compound example number as illustrated in the Examples section.

TABLE 1

IC$_{50}$ values of examples in c-Met and Ron kinase assays

| Example | c-Met IC$_{50}$ | Ron IC$_{50}$ |
|---------|-----------------|---------------|
| 1       | A               | A             |
| 2       | A               | A             |
| 70      | A               | C             |
| 71      | A               | B             |

The effect of inhibitors on the proliferation of MKN45 cells was determined using the following protocol. MKN45 cells were plated in Corning 3917 96-well white tissue culture treated plates in growth medium (RPMI, 10% FCS) at a density of 5000 cells/well in a total volume of 135 μL and incubated at 37° C., 5% CO$_2$, 95% humidity overnight. The following day, one-tenth volume of a 10× concentration of compounds was added to the wells in an 8-point dilution series. The dilution series was composed of an initial 1:5 dilution of a 10 mM stock of compound in DMSO, followed by serial 1:4 dilutions in DMSO, then a 1:20 dilution in growth medium prior to the 1:10 dilution into the cell plate. Final DMSO concentration on the cells was 0.1%, there were control wells treated with both 0.1% DMSO and no DMSO. The typical dilution range is 10 μM to 0.6 nM. Once the compound was added to the cells, plates were incubated for 3 days at 37° C., 5% CO$_2$ at 95% humidity. On the third day, after allowing all cells and reagents to come to room temperature, 25 μL of CellTiter-Glo reagent (Promega # G7573) was added to the wells. Plates were shaken on a platform for 10 minutes prior to reading luminescence for 0.1 seconds. The signal of the control wells was taken as 100% growth and growth inhibition was expressed as percent of control. IC$_{50}$ values were determined from the percent of control data using a standard four-parameter model.

The IC$_{50}$ values of exemplary compounds of the present invention determined in a cell proliferation assay using the MKN45 cell line according to the procedures described herein in at least duplicate experiments are abbreviated as follows and are shown in Table 2: A, IC$_{50}$≤0.1 μM; B, 0.1 μM<IC$_{50}$≤1 μM; C, 1 μM<IC$_{50}$≤10 μM; D, IC$_{50}$>10 μM; ND, not determined. The Example # of Table 2 corresponds to the compound example number as illustrated in the Examples section.

TABLE 2

IC$_{50}$ values of examples in MKN45 cell proliferation assay

| | Example | | | | | | | | |
|---|---|---|---|---|---|---|---|---|---|
| | 1 | 2 | 3 | 4 | 5 | 6 | 7 | 8 | 9 | 10 |
| Prolif.IC$_{50}$ | B | A | B | B | B | C | B | C | C | C |

| | Example | | | | | | | | |
|---|---|---|---|---|---|---|---|---|---|
| | 11 | 12 | 13 | 14 | 15 | 16 | 17 | 18 | 19 | 20 |
| Prolif.IC$_{50}$ | C | C | B | C | B | B | C | B | D | B |

| | Example | | | | | | | | |
|---|---|---|---|---|---|---|---|---|---|
| | 21 | 22 | 23 | 24 | 25 | 26 | 27 | 28 | 29 | 30 |
| Prolif.IC$_{50}$ | C | C | C | B | B | B | B | A | B | B |

| | Example | | | | | | | | |
|---|---|---|---|---|---|---|---|---|---|
| | 31 | 32 | 33 | 34 | 35 | 36 | 37 | 38 | 39 | 40 |

TABLE 2-continued

IC$_{50}$ values of examples in MKN45 cell proliferation assay

| Prolif.IC$_{50}$ | A | B | B | ND | ND | B | ND | B | B | B |
|---|---|---|---|---|---|---|---|---|---|---|

| Example | | | | | | | | | | |
|---|---|---|---|---|---|---|---|---|---|---|
| | 41 | 42 | 43 | 44 | 45 | 46 | 47 | 48 | 49 | 50 |
| Prolif.IC$_{50}$ | B | B | A | ND | A | B | A | A | A | B |

| Example | | | | | | | | | | |
|---|---|---|---|---|---|---|---|---|---|---|
| | 51 | 52 | 53 | 54 | 55 | 56 | 57 | 58 | 59 | 60 |
| Prolif.IC$_{50}$ | A | ND | B | ND | A | B | B | B | B | ND |

| Example | | | | | | | | | | |
|---|---|---|---|---|---|---|---|---|---|---|
| | 61 | 62 | 63 | 64 | 65 | 66 | 67 | 68 | 69 | 70 |
| Prolif.IC$_{50}$ | C | B | B | B | B | ND | B | ND | B | A |

| Example | | | | | | | | | | |
|---|---|---|---|---|---|---|---|---|---|---|
| | 71 | 72 | 73 | 74 | 75 | 76 | 77 | 78 | 79 | 80 |
| Prolif.IC$_{50}$ | A | A | A | ND | B | A | A | A | A | A |

| Example | | | | | | | | | | |
|---|---|---|---|---|---|---|---|---|---|---|
| | 81 | 82 | 83 | 84 | 85 | 86 | 87 | 88 | 89 | 90 |
| Prolif.IC$_{50}$ | B | ND | ND | ND | B | ND | ND | B | A | A |

The cellular activity of the compounds of the present invention may be determined by the following procedure. MKN45 cells were plated in Falcon 3072 96-well plates in growth media (RPMI, 10% FBS, 1% L-glutamine) at a density of 5000 cells/well and incubated at 37° C., 5% CO$_2$ overnight. The following day, one-tenth volume of a 10× concentration of compounds was added to the wells in a 6-point dilution series. The dilutions series was composed of an initial 1:5 dilution in DMSO, followed by a 1:10 dilution in growth media, for a final DMSO concentration on cells of 0.5%. Control wells were treated with 0.5% DMSO. The typical range of dilution was 10 μM to 3 nM. Once compound was added to the cells, plates were incubated for four hours at 37° C., 5% CO$_2$. Plates were then washed in PBS, and lysed in triton-based lysis buffer. Lysates were transferred to a pre-coated capture plate made by Biosource (Cat # KH00281). The phosphorylated c-MET levels were measured by incubating with a rabbit polyclonal antibody against phosphorylated c-MET ([pYpYpY1230/1234/1235]) followed by an anti-rabbit antibody conjugated to HRP. Signal was measured on a Wallac Victor plate reader at 450 nm. The DMSO signal of the control wells was defined as 100% and the percent of inhibition of phosphorylated c-Met was expressed as percent of control. IC$_{50}$ values were determined from the percent of control data using a standard four-parameter model.

The IC$_{50}$ values of exemplary compounds of the present invention determined in a c-MET cell mechanistic assay using the MKN45 cell line according to the procedures described herein in at least duplicate experiments are abbreviated as follows and are shown in Table 3: A, IC$_{50}$≤0.1 μM; B, 0.1 μM<IC$_{50}$≤1 μM; C, 1 μM<IC$_{50}$≤10 μM; D, IC$_{50}$>10 μM; ND, not determined. The Example # of Table 3 corresponds to the compound example number as illustrated in the Examples section.

TABLE 3

IC$_{50}$ values of examples in c-Met cell mechanistic assay (MKN45)

| Example | | | | | | | | | | |
|---|---|---|---|---|---|---|---|---|---|---|
| | 1 | 2 | 3 | 4 | 5 | 6 | 7 | 8 | 9 | 10 |
| Met mech IC$_{50}$ | A | A | B | B | B | B | B | ND | ND | ND |

| Example | | | | | | | | | | |
|---|---|---|---|---|---|---|---|---|---|---|
| | 11 | 12 | 13 | 14 | 15 | 16 | 17 | 18 | 19 | 20 |
| Met mech IC$_{50}$ | ND | ND | B | ND | A | ND | ND | B | C | B |

| Example | | | | | | | | | | |
|---|---|---|---|---|---|---|---|---|---|---|
| | 21 | 22 | 23 | 24 | 25 | 26 | 27 | 28 | 29 | 30 |
| Met mech IC$_{50}$ | ND | C | B | B | ND | B | A | A | B | A |

| Example | | | | | | | | | | |
|---|---|---|---|---|---|---|---|---|---|---|
| | 31 | 32 | 33 | 34 | 35 | 36 | 37 | 38 | 39 | 40 |
| Met mech IC$_{50}$ | A | B | A | B | B | B | B | B | B | A |

| Example | | | | | | | | | | |
|---|---|---|---|---|---|---|---|---|---|---|
| | 41 | 42 | 43 | 44 | 45 | 46 | 47 | 48 | 49 | 50 |
| Met mech IC$_{50}$ | A | B | A | B | A | B | A | A | B | A |

| Example | | | | | | | | | | |
|---|---|---|---|---|---|---|---|---|---|---|
| | 51 | 52 | 53 | 54 | 55 | 56 | 57 | 58 | 59 | 60 |
| Met mech IC$_{50}$ | A | B | A | B | A | A | A | A | B | ND |

| Example | | | | | | | | | | |
|---|---|---|---|---|---|---|---|---|---|---|
| | 61 | 62 | 63 | 64 | 65 | 66 | 67 | 68 | 69 | 70 |
| Met mech IC$_{50}$ | C | A | A | A | B | A | B | A | A | A |

| Example | | | | | | | | | | |
|---|---|---|---|---|---|---|---|---|---|---|
| | 71 | 72 | 73 | 74 | 75 | 76 | 77 | 78 | 79 | 80 |
| Met mech IC$_{50}$ | A | A | A | B | A | A | A | A | A | A |

| Example | | | | | | | | | | |
|---|---|---|---|---|---|---|---|---|---|---|
| | 81 | 82 | 83 | 84 | 85 | 86 | 87 | 88 | 89 | 90 |
| Met mech IC$_{50}$ | B | B | C | C | A | A | A | B | A | A |

Methods of Use

The compounds of Formula I inhibit the activity of tyrosine kinase enzymes in animals, including humans, and they are useful in the treatment and/or prevention of various diseases and conditions. In particular, compounds disclosed herein are inhibitors of kinases, in particular, but not limited to, Abl, Aurora-A, Aurora B, Alk, Jak2, Blk, c-Raf, cSRC, Src, PRK2, FGFR3, Flt3, Lck, Mek1, PDK-1, GSK3β, EGFR, p70S6K, BMX, SGK, CaMKII, Tie-2, IGF-1R, Ron, c-Met, KDR, PAK1, PAK2, and TAK1, and can be used in the treatment of proliferative diseases, such as, but not limited to, cancer.

In some aspects, the invention includes a method of treating cancer comprising administering to a mammal in need thereof a therapeutically effective amount of a compound or salt of the invention.

In some aspects, the invention includes a method of treating cancer comprising administering to a mammal in need thereof a therapeutically effective amount of a compound or salt of the invention, wherein at least one additional active anti-cancer agent is used as part of the method. In some aspects, the additional agent(s) is an EGFR inhibitor and/or an IGF-1R inhibitor.

The compounds of Formula I of the present invention are useful in the treatment of a variety of cancers, including, but not limited to, solid tumor, sarcoma, fibrosarcoma, osteoma, melanoma, retinoblastoma, rhabdomyosarcoma, glioblastoma, neuroblastoma, teratocarcinoma, hematopoietic malignancy, and malignant ascites. More specifically, the cancers include, but not limited to, lung cancer, bladder cancer, pancreatic cancer, kidney cancer, gastric cancer, breast cancer, colon cancer, prostate cancer (including bone metastases), hepatocellular carcinoma, ovarian cancer, esophageal squamous cell carcinoma, melanoma, an anaplastic large cell lymphoma, an inflammatory myofibroblastic tumor, and a glioblastoma.

In some aspects, the above methods are used to treat one or more of bladder, colorectal, nonsmall cell lung, breast, or pancreatic cancer. In some aspects, the above methods are used to treat one or more of ovarian, gastric, head and neck, prostate, hepatocellular, renal, glioma, glioma, or sarcoma cancer.

In some aspects, the invention includes a method of treating a cancer, such as those above, which is mediated at least in part by c-MET and/or RON comprising administering to a mammal in need thereof a therapeutically effective amount of a compound or salt of the invention. In some aspects thereof, the cancer is mediated at least in part by amplified c-MET. In some aspects thereof, the compound is a dual RON and c-MET inhibitor, and can be a selective inhibitor.

In some aspects, the invention includes a method, including the above methods, wherein the compound is used to inhibit EMT.

Generally, dosage levels on the order of from about 0.01 mg/kg to about 150 mg/kg of body weight per day are useful in the treatment of the above-indicated conditions, or alternatively about 0.5 mg to about 7 g per patient per day. For example, inflammation, cancer, psoriasis, allergy/asthma, disease and conditions of the immune system, disease and conditions of the central nervous system (CNS), may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

Compositions

In some aspects, the invention provides a pharmaceutical composition comprising a compound or pharmaceutically acceptable salt thereof of the invention, which is formulated with or without one or more pharmaceutical carriers.

The pharmaceutical compositions of the present invention comprise a compound represented by Formula I (or a pharmaceutically acceptable salt thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or prodrugs, metabolites, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, a pharmaceutical composition of this invention may include a pharmaceutically acceptable carrier and a compound, or a pharmaceutically acceptable salt, of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

DEFINITIONS AND ABBREVIATIONS

Unless otherwise stated, the connections of compound name moieties are at the rightmost recited moiety. That is, the substituent name starts with a terminal moiety, continues with any bridging moieties, and ends with the connecting moiety. For example, hetarylthio$C_{1-4}$alkyl has a heteroaryl group connected through a thio sulfur to a $C_{1-4}$ alkyl that connects to the chemical species bearing the substituent.

As used herein, for example, "$C_{0-12}$alkyl" is used to mean an alkyl having 0-12 carbons—that is, 0, 1, 2, 3, 4, 5, 6, 7, 8, 9, 10, 11, or 12 carbons in a straight or branched configuration. $C_0$alkyl means a single covalent chemical bond if $C_0$alkyl is a connecting moiety, and a hydrogen if $C_0$alkyl is a terminal moiety.

In all embodiments of this invention, the term "alkyl" includes both branched and straight chain alkyl groups. Typical alkyl groups are methyl, ethyl, n-propyl, isopropyl, n-butyl, sec-butyl, isobutyl, tert-butyl, n-pentyl, isopentyl, n-hexyl, n-heptyl, isooctyl, nonyl, decyl, undecyl, dodecyl, tetradecyl, hexadecyl, octadecyl, eicosyl, and the like.

The term "halo" refers to fluoro, chloro, bromo, or iodo.

Unless otherwise specified, the term "cycloalkyl" refers to a 3-12 carbon mono-cyclic, bicyclic, or polycyclic aliphatic ring structure, optionally substituted with for example, alkyl, hydroxy, oxo, and halo, such as cyclopropyl, methylcyclopropyl, cyclobutyl, cyclopentyl, 2-hydroxycyclopentyl, cyclohexyl, 4-chlorocyclohexyl, cycloheptyl, cyclooctyl, and the like. Cycloalkyl can be bicycloalkyl, polycycloalkyl or spiroalkyl.

The term "bicycloalkyl" and "polycycloalkyl" refer to a structure consisting of two or more cycloalkyl moieties that have two or more atoms in common. If the cycloalkyl moieties have exactly two atoms in common they are said to be "fused". Examples include, but are not limited to, bicyclo[3.1.0]hexyl, perhydronaphthyl, and the like. If the cycloalkyl moieties have more than two atoms in common they are said to be "bridged". Examples include, but are not limited to, bicyclo[2.2.1]heptyl ("norbornyl"), bicyclo[2.2.2]octyl, and the like.

The term "spiroalkyl" refers to a structure consisting of two cycloalkyl moieties that have exactly one atom in common. Examples include, but are not limited to, spiro[4.5]decyl, spiro[2.3]hexyl, and the like.

The term "heterobicycloalkyl" refers to a bicycloalkyl structure in which at least one carbon atom is replaced with a heteroatom independently selected from oxygen, nitrogen, and sulfur.

The term "heterospiroalkyl" refers to a spiroalkyl structure in which at least one carbon atom is replaced with a heteroatom independently selected from oxygen, nitrogen, and sulfur.

The term "alkenyl" refers to an ethylenically unsaturated hydrocarbon group, straight or branched chain, having 1 or 2 ethylenic bonds, for example vinyl, allyl, 1-butenyl, 2-butenyl, isopropenyl, 2-pentenyl, and the like.

Unless otherwise specified, the term "cycloalkenyl" refers to a cyclic aliphatic 3 to 12 ring structure, optionally substituted with alkyl, hydroxy and halo, having 1 or 2 ethylenic bonds such as methylcyclopropenyl, trifluoromethylcyclopropenyl, cyclopentenyl, cyclohexenyl, 1,4-cyclohexadienyl, and the like.

The term "alkynyl" refers to an unsaturated hydrocarbon group, straight or branched, having at least one acetylenic bond, for example ethynyl, propargyl, and the like.

The term "aryl" refers to an all-carbon monocyclic, bicyclic, or polycyclic groups of 6 to 12 carbon atoms having a completely conjugated pi-electron system, which may be optionally substituted. Examples of aryl include, but are not limited to, phenyl, 4-chlorophenyl, 4-fluorophenyl, 4-bromophenyl, 3-nitrophenyl, 2-methoxyphenyl, 2-methylphenyl, 3-methylphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl)phenyl, and 2-iodo-4-methylphenyl.

The terms "heteroaryl" refer to a substituted or unsubstituted monocyclic, bicyclic, or polycyclic group of 5 to 12 ring atoms containing one or more ring heteroatoms selected from N, O, and S, the remaining ring atoms being C, and, in addition, having a completely conjugated pi-electron system. Examples of such heteroaryl rings include, but are not limited to, furyl, thienyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridyl, pyridazinyl, pyrimidinyl, pyrazinyl, and triazinyl. The terms "heteroaryl" also include heteroaryl rings with fused carbocyclic ring systems that are partially or fully unsaturated, such as a benzene ring, to form a benzofused heteroaryl. For example, benzimidazole, benzoxazole, benzothiazole, benzofuran, quinoline, isoquinoline, quinoxaline, and the like. Furthermore, the terms "heteroaryl" include fused 5-6, 5-5, 6-6 ring systems, optionally possessing one nitrogen atom at a ring junction. Examples of such hetaryl rings include, but are not limited to, pyrrolopyrimidinyl, imidazo[1,2-a]pyridinyl, imidazo[2,1-b]thiazolyl, imidazo[4,5-b]pyridine, pyrrolo[2,1-f][1,2,4]triazinyl, and the like. Heteroaryl groups may be attached to other groups through their carbon atoms or the heteroatom(s), if applicable. For example, pyrrole may be connected at the nitrogen atom or at any of the carbon atoms.

The term "heterocycloalkyl" refers to a substituted or unsubstituted monocyclic, bicyclic, or polycyclic ring group having in the ring(s) of 3 to 12 ring atoms, in which one or more ring atoms are heteroatoms selected from N, O, and S, the remaining ring atoms being C. The rings may also have one or more double bonds. However, the rings do not have a completely conjugated pi-electron system. Examples of heterocycloalkyl rings include azetidine, oxetane, tetrahydrofuran, tetrahydropyran, oxepane, oxocane, thietane, thiazolidine, oxazolidine, oxazetidine, pyrazolidine, isoxazolidine, isothiazolidine, tetrahydrothiophene, tetrahydrothiopyran, thiepane, thiocane, azetidine, pyrrolidine, piperidine, N-methylpiperidine, azepane, 1,4-diazapane, azocane, [1,3]dioxane, oxazolidine, piperazine, homopiperazine, morpholine, thiomorpholine, 1,2,3,6-tetrahydropyridine and the like. Other examples of heterocycloalkyl rings include the oxidized forms of the sulfur-containing rings. Thus, tetrahydrothiophene-1-oxide, tetrahydrothiophene-1,1-dioxide, thiomorpholine-1-oxide, thiomorpholine-1,1-dioxide, tetrahydrothiopyran-1-oxide, tetrahydrothiopyran-1,1-dioxide, thiazolidine-1-oxide, and thiazolidine-1,1-dioxide are also considered to be heterocycloalkyl rings. The term "heterocycloalkyl" also includes fused ring systems and can include a carbocyclic ring that is partially or fully unsaturated, such as a benzene ring, to form benzofused heterocycloalkyl rings. For example, 3,4-dihydro-1,4-benzodioxine, tetrahydroquinoline, tetrahydroisoquinoline and the like. The term "heterocycloalkyl" also includes heterobicycloalkyl, heteropolycycloalkyl, or heterospiroalkyl, which are bicycloalkyl, polycycloalkyl, or spiroalkyl, in which one or more carbon atom(s) are replaced by one or more heteroatoms selected from O, N, and S. For example, 2-oxa-spiro[3.3]heptane, 2,7-diaza-spiro[4.5]decane, 6-oxa-2-thia-spiro[3.4]octane, octahydropyrrolo[1,2-a]pyrazine, 7-aza-bicyclo[2.2.1]heptane, 2-oxa-bicyclo[2.2.2]octane, and the like, are such heterocycloalkyls.

The convention "$_{x-y}$" indicates a moiety containing from x to y atoms, e.g., $_{5-6}$heterocycloalkyl means a heterocycloalkyl having five or six ring members.

The term "alkoxy" includes both branched and straight chain terminal alkyl groups attached to a bridging oxygen atom. Typical alkoxy groups include methoxy, ethoxy, n-propoxy, isopropoxy, tert-butoxy and the like.

One in the art understands that an "oxo" requires a second bond from the atom to which the oxo is attached. Accordingly, it is understood that oxo cannot be subststituted onto an aryl or heteroaryl ring.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium slats. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, formic, hydrochloric, maleic, phosphoric, sulfuric and tartaric acids. Particularly preferred are formic and hydrochloric acid.

Since the compounds of Formula (I) are intended for pharmaceutical use they are preferably provided in substantially pure form, for example at least 60% pure, more suitably at least 75% pure especially at least 98% pure (')/0 are on a weight for weight basis).

NMR Nuclear magnetic resonance
MDP(S) Mass-directed HPLC purification (system)
LC/MS Liquid chromatography mass spectrometry
LDA Lithium diisopropylamide
DCM Dichloromethane
THF Tetrahydrofuran EtOAc Ethyl acetate
MeCN Acetonitrile
DMSO Dimethylsulfoxide
Boc tert-Butyloxycarbonyl
DME 1,2-Dimethoxyethane
DMF N,N-Dimethylformamide
DIPEA Diisopropylethylamine
PS-DIEA Polymer-supported diisopropylethylamine
PS—PPh$_3$-Pd Polymer-supported Pd(PPh$_3$)$_4$
EDC 1-(3-Dimethylaminopropyl)-3-ethylcarbodiimide
HOBt 1-Hydroxybenzotnazole
DMAP 4-Dimethylaminopyridine
TBTU O-(Benzotriazol-1-yl)-N,N,N',N'-tetramethyluronium tetrafluoroborate
TEMPO 2,2,6,6-Tetramethylpiperidine-1-oxyl
TFA Trifluoroacetic acid
TLC Thin layer chromatography
Min Minute(s)
h Hour(s)
d Day(s)
RT or rt Room temperature
$t_R$ Retention time

The invention claimed is:

1. A compound of Formula I:

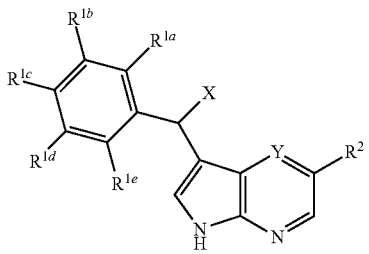

I or a pharmaceutically acceptable salt thereof, wherein:

X is $C_{1-3}$alkyl;
Y is CH;
$R^{1a}$, $R^{1b}$, $R^{1c}$, $R^{1d}$, $R^{1e}$ are each independently selected from H, halo, —CN, $C_{1-6}$ alkyl, —CF$_3$, —OCF$_3$, —OC$_{0-6}$alkyl, —S(O)$_m$C$_{1-6}$alkyl, —SO$_2$N(C$_{0-6}$alkyl)(C$_{0-6}$alkyl), —N(C$_{0-6}$alkyl)(C$_{0-6}$alkyl), —N(C$_{0-6}$alkyl)C(=O)C$_{0-6}$alkyl, —N(C$_{0-6}$alkyl)C(=O)OC$_{0-6}$alkyl, —N(C$_{0-6}$alkyl)C(=O)N(C$_{0-6}$alkyl)(C$_{0-6}$alkyl), —C(=O)C$_{0-6}$alkyl, —C(=O)OC$_{0-6}$alkyl, —C(=O)N(C$_{0-6}$alkyl)(C$_{0-6}$alkyl), —O-heterocyclyl, —N(C$_{0-6}$alkyl)-heterocyclyl, —N(C$_{0-6}$alkyl)-heteroaryl, heterocyclyl, heteroaryl, —S-heteroaryl, or —O-heteroaryl; wherein the heterocyclyl is optionally substituted with oxo, $C_{1-6}$alkyl, C(=O)OC$_{1-6}$alkyl, C(=O)C$_{0-6}$alkyl, C(=O)N(C$_{0-6}$alkyl)(C$_{0-6}$alkyl), SO$_2$N(C$_{0-6}$alkyl)(C$_{0-6}$alkyl), or SO$_2$C$_{1-6}$alkyl; wherein the alkyl is optionally substituted with —OH, —OC$_{1-6}$ alkyl, N(C$_{0-6}$alkyl)(C$_{0-6}$ alkyl), C(=O)N(C$_{0-6}$alkyl)(C$_{0-6}$alkyl), C(=O)OC$_{0-6}$alkyl, C(=O)C$_{0-6}$alkyl, heterocyclyl, or heteroaryl;
$R^2$ is selected from H, halo, —CN, —CF$_3$, —NO$_2$, $C_{1-6}$alkyl, $C_{2-6}$alkenyl, $C_{2-6}$alkynyl, $C_{3-6}$cycloalkylC$_{0-6}$alkyl, $C_{3-6}$heterocycloalkylC$_{0-6}$alkyl, arylC$_{0-6}$alkyl, or heteroarylC$_{0-6}$alkyl, any of which is optionally substituted with one or more independent $G^1$ substituents;

or $R^2$ is selected from:

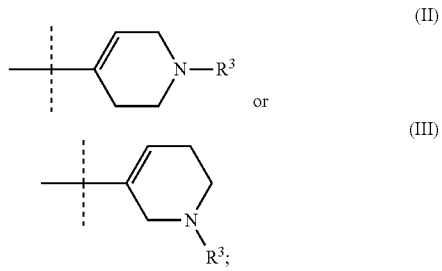

$R^3$ is selected from H, $C_{1-12}$alkyl, $R^4O$—$C_{2-12}$alkyl-, $R^4R^5N$—$C_{2-12}$alkyl-, $R^4S(O)_m$—$C_{2-12}$alkyl, $C_{3-12}$cycloalkylC$_{0-12}$alkyl, $C_{3-12}$cycloalkenylC$_{1-12}$alkyl, heterocycloalkylC$_{0-12}$alkyl, arylC$_{0-12}$alkyl, heteroarylC$_{0-12}$alkyl, $C_{1-12}$alkylC$_{3-12}$cycloalkyl, $C_{3-12}$cycloalkylC$_{3-12}$cycloalkyl, $C_{3-12}$cycloalkenylC$_{3-12}$cycloalkyl, heterocycloalkylC$_{3-12}$cycloalkyl, arylC$_{3-12}$cycloalkyl, heteroarylC$_{3-12}$ cycloalkyl, $C_{1-12}$alkyl-heterocycloalkyl, $C_{3-12}$cycloalkyl-heterocycloalkyl, $C_{3-12}$cycloalkenyl-heterocycloalkyl, heterocycloalkyl-heterocycloalkyl, aryl-heterocycloalkyl, heteroaryl-heterocycloalkyl, —C(O)R$^a$, $R^4O$—C$_{0-12}$alkylC(O)—, $R^4R^5N$—C$_{0-12}$alkylC(O)—, $R^4S(O)_m$C$_{0-12}$alkylC(O)—, —CO$_2$R$^4$, —C(O)NR$^4$R$^5$, —S(O)$_m$R$^4$, —SO$_2$NR$^4$R$^5$ or —C(S)OR$^4$, any of which is optionally substituted with one or more independent $G^2$ substituents;
$G^1$ and $G^2$ are each independently selected from halo, —CN, —CF$_3$, —OCF$_3$, —NO$_2$, oxo, R$^6$, $C_{1-12}$alkyl, $C_{2-12}$alkenyl, $C_{2-12}$alkynyl, $C_{3-12}$cycloalkylC$_{0-12}$alkyl, heterocycloalkylC$_{0-12}$alkyl, arylC$_{0-12}$alkyl, heteroarylC$_{0-12}$alkyl, —OR$^6$, —S(O)$_m$R$^6$, —NR$^6$R$^7$, —SO$_2$NR$^6$R$^7$, —C(O)R$^b$, —C(O)NR$^6$R$^7$, —C(O)—C(O)NR$^6$R$^7$, —C(O)OR$^6$, —C(O)—C(O)OR$^6$, —OC(O)R$^b$, —NR$^6$C(O)R$^b$, —NR$^6$S(O)$_2$R$^7$, —(CR$^8$R$^9$)$_n$C(O)R$^b$, —(CR$^8$R$^9$)$_n$C(O)OR$^6$, —(CR$^8$R$^9$)$_n$C(O)NR$^6$R$^7$, —(CR$^8$R$^9$)$_n$S(O)$_2$NR$^6$R$^7$, —(CR$^8$R$^9$)$_n$NR$^6$R$^7$, —(CR$^8$R$^9$)$_n$OR$^6$, —(CR$^8$R$^9$)$_n$S(O)$_m$R$^6$, —NR$^{10}$C(O)NR$^6$R$^7$, —NR$^{10}$S(O)$_2$NR$^6$R$^7$, or —NR$^{10}$S(O)NR$^6$R$^7$, any of which is optionally substituted with one or more independent $Q^1$ substituents;
$Q^1$ is selected from halo, —CN, —NO$_2$, oxo, —CF$_3$, —OCF$_3$, $C_{1-12}$alkyl, arylC$_{0-12}$alkyl, heteroarylC$_{0-12}$alkyl, $C_{3-12}$cycloalkylC$_{0-12}$alkyl, heterocycloalkylC$_{0-12}$alkyl, arylC$_{3-12}$cycloalkyl, heteroarylC$_{3-12}$cycloalkyl, heterocycloalkylC$_{3-12}$cycloalkyl, $C_{3-12}$cycloalkylC$_{3-12}$cycloalkyl, $C_{1-12}$alkyl-heterocycloalkyl, heterocycloalkyl-heterocycloalkyl, aryl-heterocycloalkyl, heteroaryl-heterocycloalkyl, —C(O)—C(O)NR$^{11}$R$^{12}$, —C(O)—C(O)OR$^{11}$, —OC(O)R$^c$, —NR$^{11}$C(O)R$^c$, —NR$^{11}$S(O)$_2$R$^{12}$, —(CR$^{13}$R$^{14}$)$_n$C(O)R$^c$, —(CR$^{13}$R$^{14}$)$_n$C(O)OR$^{11}$, —(CR$^{13}$R$^{14}$)$_n$C(O)NR$^{11}$R$^{12}$, —(CR$^{13}$R$^{14}$)$_n$S(O)$_2$NR$^{11}$R$^{12}$, —(CR$^{13}$R$^{14}$)$_n$NR$^{11}$R$^{12}$, —(CR$^{13}$R$^{14}$)$_n$OR$^{11}$, —(CR$^{13}$R$^{14}$)$_n$S(O)$_m$R$^{11}$, —NR$^{15}$C(O)NR$^{11}$R$^{12}$, —NR$^{15}$S(O)$_2$NR$^{11}$R$^{12}$ or —NR$^{15}$S(O)NR$^{11}$R$^{12}$, any of which is optionally substituted with one or more independent $Q^2$ substituents;
$Q^2$ is selected from halo, —CN, —OH, —NH$_2$, —NO$_2$, oxo, —CF$_3$, —OCF$_3$, —CO$_2$H, —S(O)$_m$H, $C_{1-12}$alkyl, arylC$_{0-12}$alkyl, heteroarylC$_{0-12}$alkyl, $C_{3-12}$cycloalkylC$_{0-12}$alkyl, heterocycloalkylC$_{0-12}$alkyl, aryl $C_{3-12}$cycloalkyl, heteroarylC$_{3-12}$cycloalkyl, heterocycloalkyl $C_{3-12}$cycloalkyl, $C_{3-12}$cycloalkylC$_{3-12}$cycloalkyl, $C_{1-12}$alkylheterocycloalkyl, heterocycloalkyl-heterocycloalkyl, aryl-heterocycloalkyl or heteroaryl-heterocycloalkyl, any of which is optionally substituted with one or more independent halo, —CN, —OH, —NH$_2$, or C$_{1-10}$alkyl which may be partially or fully halogenated, or —O—C$_{1-10}$alkyl which alkyl may be partially or fully halogenated;

each R$^4$, R$^5$, R$^6$, R$^7$, R$^8$, R$^9$, R$^{19}$, R$^{11}$, R$^{12}$, R$^{13}$, R$^{14}$, R$^{15}$, R$^a$, R$^b$, and R$^c$ is independently selected from H, C$_{1-12}$alkyl or C$_{3-12}$cycloalkyl, each optionally substituted by halo, —OCF$_3$, or by —OC$_{0-3}$alkyl, aryl C$_{0-12}$alkyl, heteroarylC$_{0-12}$alkyl, C$_{3-12}$cycloalkyl C$_{0-12}$alkyl, heterocycloalkylC$_{0-12}$alkyl, arylC$_{3-12}$cycloalkyl, heteroarylC$_{3-12}$cycloalkyl, heterocycloalkylC$_{3-12}$cycloalkyl, C$_{3-12}$cycloalkylC$_{3-12}$cycloalkyl, C$_{1-12}$alkyl-heterocycloalkyl, heterocycloalkyl-heterocycloalkyl, aryl-heterocycloalkyl, or heteroaryl-heterocycloalkyl;

—NR$^4$R$^5$, —NR$^6$R$^7$ and —NR$^{11}$R$^{12}$ is each independently linear structure; or R$^4$ and R$^5$, or R$^6$ and R$^7$, or R$^{11}$ and R$^{12}$, respectively, can be taken together with the nitrogen atom to which they are attached to form a 3-12 membered saturated or unsaturated ring, wherein said ring optionally includes one or more heteroatoms selected from O, N, or S(O)$_m$;

—CR$^8$R$^9$ or —CR$^{13}$R$^{14}$ is each independently linear structure; or R$^8$ and R$^9$, or R$^{13}$ and R$^{14}$, respectively, can be taken together with the carbon atom to which they are attached to form a 3-12 membered saturated or unsaturated ring, wherein said ring optionally includes one or more heteroatoms selected from O, N, or S(O)$_m$;

n=0-7; and m=0-2.

2. A compound or salt of claim 1, having the formula:

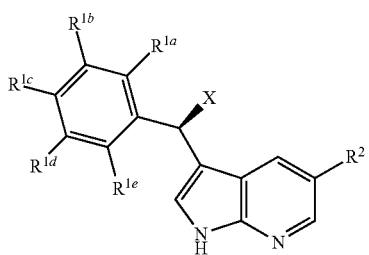

wherein X is methyl or ethyl;

R$^{1a}$ and R$^{1e}$ are each independently selected from halo, —CN, C$_{1-6}$alkyl, —CF$_3$, —OCF$_3$, or —OC$_{0-6}$alkyl;

R$^{1b}$, R$^{1c}$, and R$^{1d}$ are each independently selected from H, halo, —CN, C$_{1-6}$alkyl, —CF$_3$, —OCF$_3$, or —OC$_{0-6}$ alkyl; wherein the alkyl is optionally substituted with —OH, —OC$_{1-6}$alkyl, N(C$_{0-6}$alkyl)(C$_{0-6}$alkyl), C(=O)N(C$_{0-6}$alkyl)(C$_{0-6}$alkyl), C(=O)OC$_{0-6}$alkyl, C(=O)C$_{0-6}$alkyl, or heteroaryl;

R$^2$ is selected from halo, —CN, —CF$_3$, —NO$_2$, C$_{1-6}$alkyl, C$_{2-6}$alkenyl, C$_{2-6}$alkynyl, C$_{3-6}$cycloalkylC$_{0-6}$alkyl, C$_{3-6}$heterocycloalkylC$_{0-6}$alkyl, arylC$_{0-6}$alkyl, or heteroarylC$_{0-6}$alkyl, any of which is optionally substituted with 1-2 independent G$^1$ substituents;

or R$^2$ is selected from:

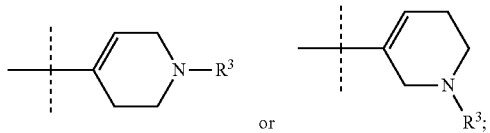

R$^3$ is selected from H, C$_{1-12}$alkyl, R$^4$O—C$_{2-12}$alkyl-, R$^4$R$^5$N—C$_{2-12}$alkyl-, R$^4$S(O)$_m$—C$_{2-12}$alkyl-, C$_{3-12}$cycloalkylC$_{0-12}$alkyl, C$_{3-12}$cycloalkenylC$_{1-12}$alkyl, C$_{3-12}$heterocycloalkylC$_{0-12}$alkyl, arylC$_{0-12}$alkyl, heteroarylC$_{0-12}$alkyl, C$_{1-12}$alkylC$_{3-12}$cycloalkyl, C$_{3-12}$cycloalkylC$_{3-12}$cycloalkyl, C$_{3-12}$cycloalkenylC$_{3-12}$cycloalkyl, C$_{3-12}$heterocycloalkylC$_{3-12}$cycloalkyl, aryl C$_{3-12}$cycloalkyl, heteroarylC$_{3-12}$cycloalkyl, C$_{1-12}$alkylC$_{3-12}$heterocycloalkyl, C$_{3-12}$cycloalkylC$_{3-12}$heterocycloalkyl, C$_{3-12}$cycloalkenylC$_{3-12}$heterocycloalkyl, C$_{3-12}$heterocycloalkylC$_{3-12}$heterocycloalkyl, arylC$_{3-12}$heterocycloalkyl, heteroarylC$_{3-12}$heterocycloalkyl, —C(O)R$^a$, R$^4$O—C$_{0-12}$alkylC(O)—, R$^4$R$^5$N—C$_{0-12}$alkylC(O)—, R$^4$S(O)$_m$C$_{0-12}$alkylC(O)—, —CO$_2$R$^4$, —C(O)NR$^4$R$^5$, —S(O)$_m$R$^4$, —SO$_2$NR$^4$R$^5$ or —C(S)OR$^4$, any of which is optionally substituted with 1-2 independent G$^2$ substituents;

each G$^1$ is independently selected from halo, —CN, —CF$_3$, —OCF$_3$, —NO$_2$, R$^6$, oxo, C$_{1-12}$alkyl, C$_{2-12}$alkenyl, C$_{2-12}$alkynyl, C$_{3-12}$cycloalkylC$_{0-12}$alkyl, C$_{3-12}$heterocycloalkylC$_{0-12}$alkyl, arylC$_{0-12}$alkyl, heteroaryl C$_{0-12}$alkyl, —OR$^6$, —S(O)$_m$R$^6$, —NR$^6$R$^7$, —SO$_2$NR$^6$R$^7$, —C(O)R$^b$, —C(O)NR$^6$R$^7$, —C(O)—C(O)NR$^6$R$^7$, —C(O)OR$^6$, —C(O)—C(O)OR$^6$, —OC(O)R$^b$, —NR$^6$C(O)R$^b$, —NR$^6$S(O)$_2$R$^7$, —(CR$^8$R$^9$)$_n$C(O)R$^b$, —(CR$^8$R$^9$)$_n$C(O)OR$^6$, —(CR$^8$R$^9$)$_n$C(O)NR$^6$R$^7$, —(CR$^8$R$^9$)$_n$S(O)$_2$NR$^6$R$^7$, —(CR$^8$R$^9$)$_n$NR$^6$R$^7$, —(CR$^8$R$^9$)$_n$OR$^6$, —(CR$^8$R$^9$)$_n$S(O)$_m$R$^6$, —NR$^{10}$C(O)NR$^6$R$^7$, —NR$^{10}$S(O)$_2$NR$^6$R$^7$, or —NR$^{10}$S(O)NR$^6$R$^7$, any of which is optionally substituted with 1-2 independent Q$^1$ substituents;

each G$^2$ is independently selected from halo, —CN, —CF$_3$, —OCF$_3$, —NO$_2$, C$_{1-12}$alkyl, C$_{2-12}$alkenyl, C$_{2-12}$alkynyl, —OR$^6$, —S(O)$_m$R$^6$, —NR$^6$R$^7$, —SO$_2$NR$^6$R$^7$, —C(O)R$^b$, —C(O)NR$^6$R$^7$, —C(O)—C(O)NR$^6$R$^7$, —C(O)OR$^6$, —C(O)—C(O)OR$^6$, —OC(O)R$^b$, —NR$^6$C(O)R$^b$, —NR$^6$S(O)$_2$R$^7$, —(CR$^8$R$^9$)$_n$C(O)R$^b$, —(CR$^8$R$^9$)$_n$C(O)OR$^6$, —(CR$^8$R$^9$)$_n$C(O)NR$^6$R$^7$, —(CR$^8$R$^9$)$_n$S(O)$_2$NR$^6$R$^7$, —(CR$^8$R$^9$)$_n$NR$^6$R$^7$, —(CR$^8$R$^9$)$_n$OR$^6$, —(CR$^8$R$^9$)$_n$S(O)$_m$R$^6$, —NR$^{19}$C(O)NR$^6$R$^7$, —NR$^{10}$S(O)$_2$NR$^6$R$^7$, or —NR$^{10}$S(O)NR$^6$R$^7$, any of which is optionally substituted with 1-2 independent Q$^1$ substituents;

each Q$^1$ is selected from halo, —CN, —NO$_2$, oxo, —CF$_3$, —OCF$_3$, C$_{1-12}$alkyl, C$_{3-7}$cycloalkyl, —C(O)—C(O)NR$^{11}$R$^{12}$, —C(O)—C(O)OR$^{11}$, —OC(O)R$^c$, —NR$^{11}$C(O)R$^c$, —NR$^{11}$S(O)$_2$R$^{12}$, —(CR$^{13}$R$^{14}$)$_n$C(O)R$^c$, —(CR$^{13}$R$^{14}$)$_n$C(O)OR$^{11}$, —(CR$^{13}$R$^{14}$)$_n$C(O)NR$^{11}$R$^{12}$, —(CR$^{13}$R$^{14}$)$_n$S(O)$_2$NR$^{11}$R$^{12}$, —(CR$^{13}$R$^{14}$)$_n$NR$^{11}$R$^{12}$, —(CR$^{13}$R$^{14}$)$_n$OR$^{11}$, —(CR$^{13}$R$^{14}$)$_n$S(O)$_m$R$^{11}$, —NR$^{15}$C(O)NR$^{11}$R$^{12}$, —NR$^{15}$S(O)$_2$NR$^{11}$R$^{12}$ or —NR$^{15}$S(O)NR$^{11}$R$^{12}$;

each R$^4$, R$^5$, R$^6$, R$^7$, R$^8$, R$^9$, R$^{19}$, R$^{11}$, R$^{12}$, R$^{13}$, R$^{14}$, R$^{15}$, R$^a$, R$^b$, and R$^c$ is independently C$_{0-12}$alkyl or C$_{3-7}$cycloalkyl, each independently optionally substituted by halo, —OCF$_3$, or —OC$_{0-3}$alkyl;

each —NR$^4$R$^5$, —NR$^6$R$^7$ and —NR$^{11}$R$^{12}$ is independently linear in structure; or R$^4$ and R$^5$, or R$^6$ and R$^7$, or R$^{11}$ and $R^{12}$, respectively, can be taken together with the nitrogen atom to which they are attached to form a 3-12 membered saturated or unsaturated ring, wherein said ring optionally includes one or more heteroatoms selected from O, N, or $S(O)_m$;

each $-CR^9R^9$ and $-CR^{13}R^{14}$ is independently linear in structure; or $R^8$ and $R^9$, or $R^{13}$ and $R^{14}$, respectively, can be taken together with the carbon atom to which they are attached to form a 3-12 membered saturated or unsaturated ring, wherein said ring optionally includes one or more heteroatoms selected from O, N, or $S(O)_m$;

n=0-4; and m=0-2.

3. The compound or salt of claim 1, having the formula:

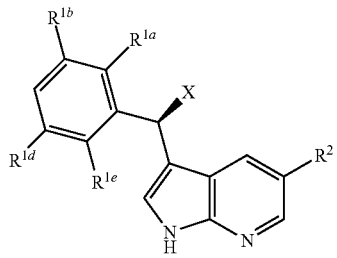

$R^{1a}$ and $R^{1e}$ are each independently selected from halo, —CN, $C_{1-6}$alkyl, —CF$_3$, —OCF$_3$, or —OC$_{1-6}$alkyl;

$R^{1b}$ and $R^{1d}$ are each independently selected from H, halo, —CN, $C_{1-6}$alkyl, —CF$_3$, —OCF$_3$, or —OC$_{1-6}$alkyl;

(i) $R^2$ is phenyl or pyridinyl, each substituted by $G^1$ wherein $G^1$ is $_{4-7}$heterocycloalkyl optionally substituted with halogen, —OH, —OCH$_3$, or $C_{1-3}$alkyl, or $G^1$ is —C(O)NR$^6$R$^7$; wherein each $R^6$ and $R^7$ is independently $C_{0-3}$ alkyl; or NR$^6$R$^7$ defines a $_{4-7}$heterocycloalkyl optionally substituted by $C_{1-6}$alkyl;

or (ii) $R^2$ is pyrazolo optionally substituted by $G^1$ wherein $G^1$ is $_{4-6}$heterocycloalkyl optionally substituted by halo, —R$^6$, oxo, —S(O)$_m$R$^6$, —SO$_2$NR$^6$R$^7$, —C(O)R$^b$, —C(O)NR$^6$R$^7$, —C(O)—C(O)NR$^6$R$^7$, —C(O)OR$^6$, or —C(O)—C(O)OR$^6$; or $G^1$ is $C_{3-6}$cycloalkyl optionally substituted by OH, —OR$^6$, OXO, —S(O)$_m$R$^6$, —SO$_2$NR$^6$R$^7$, —C(O)R$^b$, —C(O)NR$^6$R$^7$, —C(O)—C(O)NR$^6$R$^7$, —C(O)OR$^6$, or —C(O)—C(O)OR$^6$; or —C$_{1-6}$alkyl which alkyl can be substituted by halo or —OC$_{0-5}$alkyl; or $G^1$ is $C_{1-6}$alkyl optionally substituted by —OH, —OR$^6$, —R$^6$, oxo, —NR$^6$R$^7$, —C(O)R$^b$, —C(O)NR$^6$R$^7$, —C(O)—C(O)NR$^6$R$^7$, —C(O)OR$^6$, —C(O)—C(O)OR$^6$, —OC(O)R$^b$, —NR$^6$C(O)R$^b$, —NR$^6$S(O)$_2$R$^7$, —(CR$^8$R$^9$)$_n$C(O)R$^b$, —(CR$^8$R$^9$)$_n$C(O)OR$^6$, —(CR$^8$R$^9$)$_n$C(O)NR$^6$R$^7$, —(CR$^8$R$^9$)$_n$S(O)$_2$NR$^6$R$^7$, —(CR$^8$R$^9$)$_n$NR$^6$R$^7$, —(CR$^8$R$^9$)$_n$OR$^6$, —(CR$^8$R$^9$)$_n$S(O)$_m$R$^6$, —NR$^{10}$C(O)NR$^6$R$^7$, —NR$^{10}$S(O)$_2$NR$^6$R$^7$, or —NR$^{10}$S(O)NR$^6$R$^7$; wherein each $R^6$, $R^7$, $R^8$, $R^9$, $R^{10}$, and $R^b$ is independently $C_{0-5}$alkyl or $C_{3-6}$cycloalkyl, each independently optionally substituted by halo, —OCF$_3$, or —OC$_{0-3}$alkyl; or NR$^6$R$^7$ defines a $_{4-7}$heterocycloalkyl optionally substituted by $C_{1-6}$alkyl; and wherein each m is independently 0-2; each n is independently 0-2.

4. The compound or salt of claim 1, having the formula:

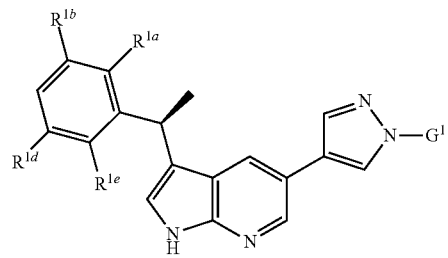

wherein $R^{1a}$ and $R^{1e}$ are each independently selected from halo, —CN, $C_{1-6}$alkyl, —CF$_3$, —OCF$_3$, or —OC$_{1-6}$alkyl;

$R^{1b}$ and $R^{1d}$ are each independently selected from H, halo, —CN, $C_{1-6}$alkyl, —CF$_3$, —OCF$_3$, or —OC$_{1-6}$alkyl;

$G^1$ is $_{4-6}$heterocycloalkyl optionally substituted by halo, —R$^6$, oxo, —S(O)$_m$R$^6$, —SO$_2$NR$^6$R$^7$, —C(O)R$^b$, —C(O)NR$^6$R$^7$, —C(O)—C(O)NR$^6$R$^7$, —C(O)OR$^6$, or —C(O)—C(O)OR$^6$;

or $G^1$ is $_{3-6}$cycloalkyl optionally substituted by OH, —OR$^6$, oxo, —S(O)$_m$R$^6$, —SO$_2$NR$^6$R$^7$, —C(O)R$^b$, —C(O)NR$^6$R$^7$, —C(O)—C(O)NR$^6$R$^7$, —C(O)OR$^6$, or —C(O)—C(O)OR$^6$, or —C$_{1-6}$alkyl which alkyl can be substituted by halo or —OC$_{0-5}$alkyl;

or $G^1$ is $C_{1-6}$alkyl optionally substituted by —OH, —OR$^6$, —R$^6$, oxo, —NR$^6$R$^7$, —C(O)R$^b$, —C(O)NR$^6$R$^7$, —C(O)—C(O)NR$^6$R$^7$, —C(O)OR$^6$, —C(O)—C(O)OR$^6$, —OC(O)R$^b$, —NR$^6$C(O)R$^b$, —NR$^6$S(O)$_2$R$^7$, —(CR$^8$R$^9$)$_n$C(O)R$^b$, —(CR$^8$R$^9$)$_n$C(O)OR$^6$, —(CR$^8$R$^9$)$_n$C(O)NR$^6$R$^7$, —(CR$^8$R$^9$)$_n$S(O)$_2$NR$^6$R$^7$, —(CR$^8$R$^9$)$_n$NR$^6$R$^7$, —(CR$^8$R$^9$)$_n$OR$^6$, —(CR$^8$R$^9$)$_n$S(O)$_m$R$^6$, —NR$^{10}$C(O)NR$^6$R$^7$, —NR$^{10}$S(O)$_2$NR$^6$R$^7$, or —NR$^{10}$S(O)NR$^6$R$^7$;

wherein each $R^6$, $R^7$, $R^8$, $R^9$, $R^{10}$, and $R^b$ is independently $C_{0-5}$ alkyl or $C_{3-6}$cycloalkyl, each independently optionally substituted by halo, —OCF$_3$, or —OC$_{0-3}$alkyl; or NR$^6$R$^7$ defines a $_{4-7}$heterocycloalkyl optionally substituted by $C_{1-6}$alkyl; and each m is independently 0-2; and each n is independently 0-2.

5. The compound or salt of claim 1, having the formula:

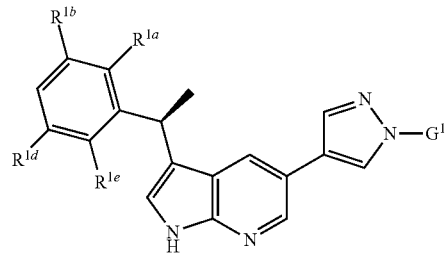

wherein $R^{1a}$ and $R^{1e}$ are both Cl;

each $R^{1b}$ and $R^{1d}$ is independently H, F, or —OCH$_3$;

$G^1$ is $_{3-6}$cycloalkyl substituted by 0-2 substituents independently selected from —OH, —OR$^6$, oxo, —S(O)$_m$R$^6$, —SO$_2$NR$^6$R$^7$, —C(O)R$^b$, —C(O)NR$^6$R$^7$, —C(O)—C(O)NR$^6$R$^7$, —C(O)OR$^6$, —C(O)—C(O)OR$^6$, or —C$_{1-3}$ alkyl which alkyl can be substituted by halo or —OC$_{0-5}$ alkyl;

wherein each $R^6$, $R^7$, and $R^b$ is independently $C_{0-5}$ alkyl or $C_{3-6}$cycloalkyl; or NR$^6$R$^7$ defines a $_{4-7}$heterocycloalkyl optionally substituted by $C_{1-6}$alkyl; and m is 0-2.

6. The compound or salt of claim 1, having the formula:

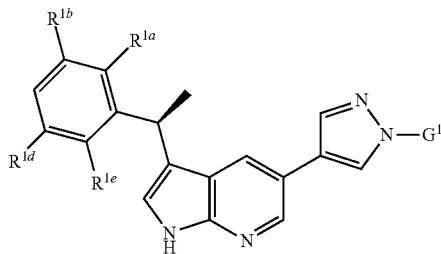

wherein $R^{1a}$ and $R^{1e}$ are both Cl;

each $R^{1b}$ and $R^{1d}$ is independently H, F, or —OCH$_3$;

$G^1$ is $C_{1-6}$alkyl substituted by 0-2 substituents independently selected from —OH, —OR$^6$, —R$^6$, oxo, —NR$^6$R$^7$, —C(O)R$^b$, —C(O)NR$^6$R$^7$, —C(O)—C(O)NR$^6$R$^7$, —C(O)OR$^6$, —C(O)—C(O)OR$^6$, —OC(O)R$^b$, —NR$^6$C(O)R$^b$, —NR$^6$S(O)$_2$R$^7$, —(CR$^8$R$^9$)—C(O)R$^b$, —(CR$^8$R$^9$)—C(O)OR$^6$, —(CR$^8$R$^9$)—C(O)NR$^6$R$^7$, —(CR$^8$R$^9$)—S(O)$_2$NR$^6$R$^7$, —(CR$^8$R$^9$)—NR$^6$R$^7$, —(CR$^8$R$^9$)—OR$^6$, —(CR$^8$R$^9$)—S(O)$_m$R$^6$, —NR$^{19}$C(O)NR$^6$R$^7$, —NR$^{19}$S(O)$_2$NR$^6$R$^7$, —NR$^{19}$S(O)NR$^6$R$^7$, or $_{4-7}$heterocycloalkyl optionally substituted by $C_{1-6}$alkyl;

wherein each R$^6$, R$^7$, R$^8$, R$^9$, R$^{10}$, and R$^b$ is independently $C_{0-5}$ alkyl or $C_{3-6}$cycloalkyl; or NR$^6$R$^7$ defines a $_{4-7}$heterocycloalkyl optionally substituted by $C_{1-6}$alkyl;

m is 0-2; and each n is independently 0-2.

7. The compound or salt of claim 1, having the formula:

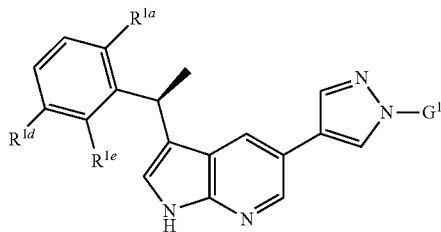

wherein $R^{1a}$ and $R^{1e}$ are both Cl;

$R^{1d}$ is F or —OCH$_3$;

$G^1$ is $C_{1-6}$alkyl substituted by 0-2 substituents independently selected from —OH, —OR$^6$, —R$^6$, oxo, —NR$^6$R$^7$, —C(O)R$^b$, —C(O)NR$^6$R$^7$, —C(O)—C(O)NR$^6$R$^7$, —C(O)OR$^6$, —C(O)—C(O)OR$^6$, —OC(O)R$^b$, —NR$^6$C(O)R$^b$, —NR$^6$S(O)$_2$R$^7$, —(CR$^8$R$^9$)$_n$C(O)R$^b$, —(CR$^8$R$^9$)$_n$C(O)OR$^6$, —(CR$^8$R$^9$)$_n$C(O)NR$^6$R$^7$, —(CR$^8$R$^9$)$_n$S(O)$_2$NR$^6$R$^7$, —(CR$^8$R$^9$)$_n$NR$^6$R$^7$, —(CR$^8$R$^9$)$_n$OR$^6$, —(CR$^8$R$^9$)$_n$S(O)$_m$R$^6$, —NR$^{10}$C(O)NR$^6$R$^7$, —NR$^{10}$S(O)$_2$NR$^6$R$^7$, —NR$^{10}$S(O)NR$^6$R$^7$, or $_{4-7}$heterocycloalkyl optionally substituted by $C_{1-6}$alkyl;

wherein each R$^6$, R$^7$, R$^8$, R$^9$, R$^{10}$, and R$^b$ is independently $C_{0-5}$ alkyl or $C_{3-6}$cycloalkyl; or NR$^6$R$^7$ defines a $_{4-7}$heterocycloalkyl optionally substituted by $C_{1-6}$alkyl;

m is 0-2; and each n is independently 0-2.

8. The compound or salt of claim 1, having the formula:

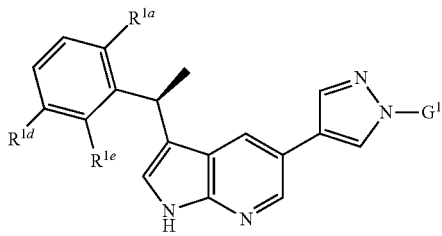

wherein $R^{1a}$ and $R^{1e}$ are both Cl;

$R^{1d}$ is F;

$G^1$ is $C_{1-6}$alkyl substituted by 0-2 substituents independently selected from —OH, —OR$^6$, —R$^6$, oxo, —NR$^6$R$^7$, —C(O)R$^b$, —C(O)NR$^6$R$^7$, —C(O)—C(O)NR$^6$R$^7$, —C(O)OR$^6$, —C(O)—C(O)OR$^6$, —OC(O)R$^b$, —NR$^6$C(O)R$^b$, —NR$^6$S(O)$_2$R$^7$, —(CR$^8$R$^9$)$_n$C(O)R$^b$, —(CR$^8$R$^9$)$_n$C(O)OR$^6$, —(CR$^8$R$^9$)$_n$C(O)NR$^6$R$^7$, —(CR$^9$R$^9$)$_n$S(O)$_2$NR$^6$R$^7$, —(CR$^8$R$^9$)$_n$NR$^6$R$^7$, —(CR$^8$R$^9$)$_n$OR$^6$, —(CR$^8$R$^9$)$_n$S(O)$_m$R$^6$, —NR$^{10}$C(O)NR$^6$R$^7$, —NR$^{10}$S(O)$_2$NR$^6$R$^7$, —NR$^{10}$S(O)NR$^6$R$^7$, or $_{4-7}$heterocycloalkyl optionally substituted by $C_{1-6}$alkyl;

wherein each R$^6$, R$^7$, R$^8$, R$^9$, R$^{10}$, and R$^b$ is independently $C_{0-3}$ alkyl or $C_{3-6}$cycloalkyl; or NR$^6$R$^7$ defines a $_{4-7}$heterocycloalkyl optionally substituted by $C_{1-6}$alkyl;

m is 0-2; and each n is independently 0-2.

9. The compound or salt of claim 1, having the formula:

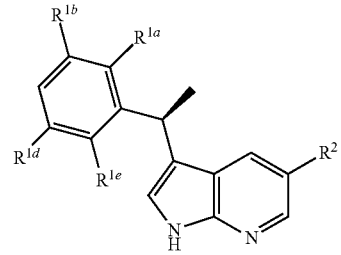

wherein $R^{1a}$ and $R^{1e}$ are each independently selected from halo, —CN, $C_{1-6}$alkyl, —CF$_3$, —OCF$_3$, or —OC$_{1-6}$alkyl;

$R^{1b}$ and $R^{1d}$ are each independently selected from H, halo, —CN, $C_{1-6}$alkyl, —CF$_3$, —OCF$_3$, or —OC$_{1-6}$alkyl;

$R^2$ is phenyl or pyridinyl, each substituted by $G^1$;

$G^1$ is $_{4-7}$heterocycloalkyl optionally substituted with halogen, —OH, —OCH$_3$, or $C_{1-3}$alkyl;

or $G^1$ is —C(O)NR$^6$R$^7$; and each R$^6$ and R$^7$ is independently $C_{0-3}$ alkyl or $C_{3-6}$cycloalkyl; or NR$^6$R$^7$ defines a $_{4-7}$heterocycloalkyl optionally substituted by $C_{1-6}$alkyl.

10. The compound or salt of claim 1, having the formula:

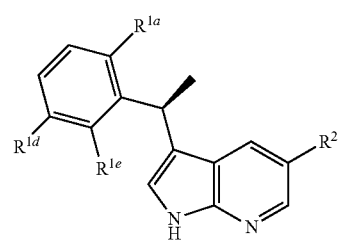

wherein $R^{1a}$ and $R^{1e}$ are both Cl;
$R^{1d}$ is F or methoxy;
$R^2$ is selected from

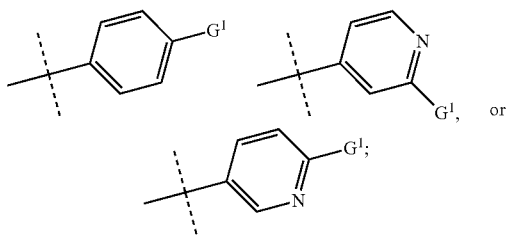

and $G^1$ is selected from piperazine, homopiperazine, morpholine, piperidine, azetidine, Or pyrrolidine, each optionally substituted with halogen, —OH, —OCH$_3$, or C$_{1-3}$alkyl or C$_{3-6}$cycloalkyl.

11. The compound or salt of claim 1, having the formula:

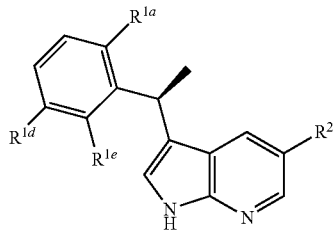

wherein $R^{1a}$ and $R^{1e}$ are both Cl;
$R^{1d}$ is F or methoxy;
$R^2$ is selected from

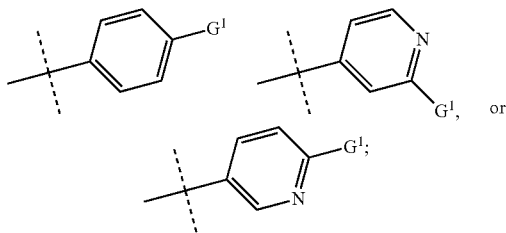

$G^1$ is NR$^6$R$^7$;
wherein each R$^6$ and R$^7$ is independently C$_{0-3}$ alkyl or C$_{3-6}$cycloalkyl; or NR$^6$R$^7$ defines a ring selected from piperazine, homopiperazine, morpholine, piperidine, azetidine, or pyrrolidine, each optionally substituted with halogen, —OH, —OCH$_3$, C$_{1-3}$alkyl, or C$_{3-6}$cycloalkyl.

12. The compound or salt of claim 1, having the formula:

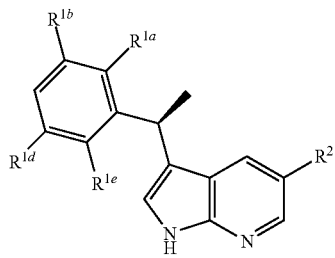

wherein $R^{1a}$ and $R^{1a}$ are each independently selected from halo, —CN, C$_{1-6}$alkyl, —CF$_3$, —OCF$_3$, or —OC$_{1-6}$alkyl;
$R^{1b}$ and $R^{1d}$ are each independently selected from H, halo, —CN, C$_{1-6}$alkyl, —CF$_3$, —OCF$_3$, or —OC$_{1-6}$alkyl;
$R^2$ is selected from

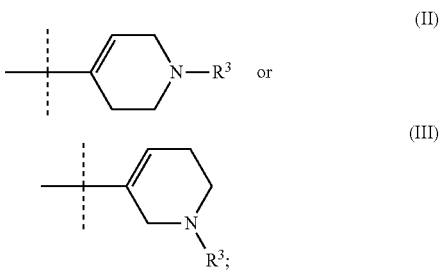

wherein R$^3$ is selected from —R$^4$, —C(O)R$^a$, R$^4$O—O$_{0-12}$alkylC(O)—, R$^4$R$^5$N—C$_{0-12}$alkylC(O)—, —CO$_2$R$^4$, —C(O)NR$^4$R$^5$, —S(O)$_m$R$^4$, —SO$_2$NR$^4$R$^5$, or —C(S)OR$^4$); each R$^a$, R$^4$, and R$^5$ is independently C$_{0-3}$alkyl or C$_{3-6}$cycloalkyl; or NR$^4$R$^5$ defines a $_{4-7}$heterocycloalkyl optionally substituted by C$_{1-6}$alkyl;
each m is independently 0-2.

13. The compound or salt of claim 1, which exhibits inhibition of c-Met in a cellular assay with an IC$_{50}$ of about 100 nM or less.

14. The compound or salt of claim 13, which exhibits inhibition of Ron in a cellular assay with an IC$_{50}$ of about 200 nM or less.

15. The compound or salt of claim 14, which is about 10-fold or more selective for c-Met over KDR.

16. The compound or salt of claim 1, the compound selected from one of:
4-{3-[1-(2,6-Dichloro-3-fluoropheny)ethyl]-1H-pyrrolo[2,3-b]pyridin-5-yl}-3,6-dihydro-2H-pyridine-1-carboxamide (ex.33),
4-(4-{3-[(1S)-(2,6-Dichloro-3-fluorophenyl)ethyl]-1H-pyrrolo[2,3-b]pyridin-5-yl}-pyrazol-1-yl)-piperidine-1-carbaldehyde (ex.71).
3-[(S)-1-(2,6-Dichloro-3-fluorophenyl)ethyl]-5-(1-piperidin-4-yl-1H-pyrazol-4-yl)-1H-pyrrolo[2,3-b]pyridine (ex.80),
trans-4-(4-{3-[(1S)-1-(2,6-dichloro-3-fluorophenyl)ethyl]-1H-pyrrolo[2,3-b]pyridin-5-yl}-1H-pyrazol-1-yl)cyclohexanol (ex.86),
cis-4-(4-{3-[(1S)-1-(2,6-dichloro-3-fluorophenyl)ethyl]-1H-pyrrolo[2,3-b]pyridin-5-yl}-1H-pyrazol-1-yl)cyclohexanol (ex.87), or
(2S)-3-(4-{3-[(1S)-1-(2,6-dichloro-3-fluorophenyl)ethyl]-1H-pyrrolor[2,3-b]pyridin-5-yl}-1H-pyrazol-1-yl)propane-1,2-diol (ex.90).

17. A pharmaceutical composition comprising the compound or salt of claim 1, formulated with or without one or more pharmaceutical carriers.

18. A method of treating gastric cancer comprising administering to a mammal in need thereof a therapeutically effective amount of a compound or salt of claim 1.

* * * * *